(12) United States Patent
Flock et al.

(10) Patent No.: US 10,779,810 B2
(45) Date of Patent: Sep. 22, 2020

(54) DEVICES AND METHODS FOR SURGICAL RETRACTION

(71) Applicant: Medos International Sarl, Le Locle (CH)

(72) Inventors: Judith Flock, Basel (CH); Joern Richter, Kandern (DE); Jan Klett, Aesch (CH); Daniel Thommen, Liestal (CH); Michael White, Liestal (CH); Stephane Gully, Rixheim (FR); Eric Buehlmann, Duxbury, MA (US); Veronique Christine Zollman, Gebenstorf (CH); William Kane, Newport Beach, CA (US); Sean Lilienfeld, Sharon, MA (US); Joseph Amaral, Cumberland, RI (US); John Canady, Iowa City, IA (US); Thomas Gamache, Westport, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 15/786,846

(22) Filed: Oct. 18, 2017

(65) Prior Publication Data

US 2018/0110503 A1  Apr. 26, 2018

Related U.S. Application Data

(63) Continuation-in-part of application No. 15/437,792, filed on Feb. 21, 2017, which is a continuation-in-part of application No. 15/254,877, filed on Sep. 1, 2016.
(Continued)

(51) Int. Cl.
*A61B 17/02* (2006.01)
*A61B 90/00* (2016.01)
(Continued)

(52) U.S. Cl.
CPC ........ *A61B 17/025* (2013.01); *A61B 1/00045* (2013.01); *A61B 1/00091* (2013.01);
(Continued)

(58) Field of Classification Search
CPC .... A61B 17/02; A61B 17/025; A61B 17/0218
See application file for complete search history.

(56) References Cited

U.S. PATENT DOCUMENTS

| 4,318,401 A | 3/1982 | Zimmerman |
| 4,573,448 A | 3/1986 | Kambin |

(Continued)

FOREIGN PATENT DOCUMENTS

| CN | 102727309 B | 11/2014 |
| DE | 94 15 039 U1 | 11/1994 |

(Continued)

OTHER PUBLICATIONS

Hott, J. S., et al., "A new table-fixed retractor for anterior odontoid screw fixation: technical note," J Neurosurg (Spine 3), 2003, v. 98, pp. 118-120.
(Continued)

*Primary Examiner* — Christopher J Beccia
(74) *Attorney, Agent, or Firm* — Nutter McClennen & Fish LLP

(57) ABSTRACT

Devices and methods for surgical retraction are described herein, e.g., for retracting nerve tissue, blood vessels, or other obstacles to create an unobstructed, safe surgical area. In some embodiments, a surgical access device can include an outer tube that defines a working channel through which a surgical procedure can be performed. A shield, blade, arm, or other structure can be manipulated with respect to the outer tube to retract an obstacle. For example, an inner blade can protrude from a distal end of the outer tube to retract obstacles disposed distal to the outer tube. The inner blade
(Continued)

can be movable between a radially-inward position and a radially-outward position. The radially-inward position can allow insertion of the blade to the depth of the obstacle to position the obstacle adjacent to and radially-outward from the blade. Subsequent movement of the blade to the radially-outward position can retract the obstacle in a radially-outward direction. The blade can be manipulated remotely, e.g., from a proximal end of the access device or a location disposed outside of the patient. The blade can be manipulated in various ways, such as by rotating the blade relative to the outer tube, translating the blade longitudinally relative to the outer tube, sliding an expander along the blade, driving a wedge between the blade and the outer tube, actuating a cam mechanism of the access device, and/or pivoting the blade relative to the outer tube.

14 Claims, 28 Drawing Sheets

Related U.S. Application Data

(60) Provisional application No. 62/468,475, filed on Mar. 8, 2017, provisional application No. 62/214,297, filed on Sep. 4, 2015.

(51) Int. Cl.

| | | |
|---|---|---|
| *A61B 90/50* | (2016.01) | |
| *A61B 90/57* | (2016.01) | |
| *A61B 1/00* | (2006.01) | |
| *A61B 1/012* | (2006.01) | |
| *A61B 1/018* | (2006.01) | |
| *A61B 1/05* | (2006.01) | |
| *A61B 1/055* | (2006.01) | |
| *A61B 1/07* | (2006.01) | |
| *A61B 1/12* | (2006.01) | |
| *A61B 1/233* | (2006.01) | |
| *A61B 1/267* | (2006.01) | |
| *A61B 1/313* | (2006.01) | |
| *A61B 1/317* | (2006.01) | |
| *A61B 1/32* | (2006.01) | |
| *A61B 5/04* | (2006.01) | |
| *A61B 5/06* | (2006.01) | |
| *A61B 5/00* | (2006.01) | |
| *A61B 17/00* | (2006.01) | |
| *A61B 17/32* | (2006.01) | |
| *A61B 17/34* | (2006.01) | |
| *A61B 17/60* | (2006.01) | |
| *A61B 17/70* | (2006.01) | |
| *A61B 18/18* | (2006.01) | |
| *A61F 2/44* | (2006.01) | |
| *A61F 2/46* | (2006.01) | |
| *A61B 34/20* | (2016.01) | |
| *A61B 34/00* | (2016.01) | |
| *A61B 90/30* | (2016.01) | |
| *A61B 17/16* | (2006.01) | |
| *A61B 17/17* | (2006.01) | |
| *A61B 18/00* | (2006.01) | |
| *A61B 17/56* | (2006.01) | |

(52) U.S. Cl.
CPC ...... *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/317* (2013.01); *A61B 1/3132* (2013.01); *A61B 1/3135* (2013.01); *A61B 1/32* (2013.01); *A61B 5/04001* (2013.01); *A61B 5/068* (2013.01); *A61B 5/407* (2013.01); *A61B 5/4041* (2013.01); *A61B 17/00234* (2013.01); *A61B 17/0218* (2013.01); *A61B 17/0293* (2013.01); *A61B 17/320068* (2013.01); *A61B 17/3421* (2013.01); *A61B 17/3423* (2013.01); *A61B 17/3462* (2013.01); *A61B 17/60* (2013.01); *A61B 17/708* (2013.01); *A61B 17/7032* (2013.01); *A61B 17/7074* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 17/0206* (2013.01); *A61B 17/1637* (2013.01); *A61B 17/1671* (2013.01); *A61B 17/1757* (2013.01); *A61B 17/3439* (2013.01); *A61B 17/70* (2013.01); *A61B 17/7083* (2013.01); *A61B 34/70* (2016.02); *A61B 90/30* (2016.02); *A61B 2017/0034* (2013.01); *A61B 2017/00261* (2013.01); *A61B 2017/00314* (2013.01); *A61B 2017/00345* (2013.01); *A61B 2017/00407* (2013.01); *A61B 2017/00477* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 2017/0256* (2013.01); *A61B 2017/0262* (2013.01); *A61B 2017/320075* (2017.08); *A61B 2017/3443* (2013.01); *A61B 2017/3445* (2013.01); *A61B 2017/3447* (2013.01); *A61B 2017/3454* (2013.01); *A61B 2017/3484* (2013.01); *A61B 2017/564* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 2090/034* (2016.02); *A61B 2090/036* (2016.02); *A61B 2090/08021* (2016.02); *A61B 2090/3983* (2016.02); *A61F 2002/4635* (2013.01)

(56) References Cited

U.S. PATENT DOCUMENTS

| | | |
|---|---|---|
| 4,646,738 A | 3/1987 | Trott |
| 4,678,459 A | 7/1987 | Onik et al. |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,615,690 A | 4/1997 | Giurtino et al. |
| 5,618,293 A | 4/1997 | Sample et al. |
| 5,662,300 A | 9/1997 | Michelson |

(56) References Cited

U.S. PATENT DOCUMENTS

| | | |
|---|---|---|
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,792,044 A | 8/1998 | Foley et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,520,495 B1 | 2/2003 | La Mendola |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,685,724 B1 | 2/2004 | Haluck |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,179,261 B2 | 2/2007 | Sicvol et al. |
| 7,182,731 B2 | 2/2007 | Nguyen et al. |
| 7,226,413 B2 | 6/2007 | McKinley |
| 7,341,556 B2 | 3/2008 | Shalman |
| 7,434,325 B2 | 10/2008 | Foley et al. |
| 7,491,168 B2 | 2/2009 | Raymond et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,079,952 B2 | 12/2011 | Fujimoto |
| 8,092,464 B2 | 1/2012 | McKay |
| 8,096,944 B2 | 1/2012 | Harrel |
| 8,202,216 B2 | 6/2012 | Melkent et al. |
| 8,236,006 B2 | 8/2012 | Hamada |
| 8,303,492 B2 | 11/2012 | Ito |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,419,625 B2 | 4/2013 | Ito |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,648,932 B2 | 2/2014 | Talbert et al. |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,888,689 B2 | 11/2014 | Poll et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,545 B2 | 1/2015 | To |
| 8,936,605 B2 | 1/2015 | Greenberg |
| 8,952,312 B2 | 2/2015 | Blanquart et al. |
| 8,961,404 B2 | 2/2015 | Ito |
| 8,972,714 B2 | 3/2015 | Talbert et al. |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,036 B2 | 6/2015 | Poll et al. |
| 9,050,037 B2 | 6/2015 | Poll et al. |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,123,602 B2 | 9/2015 | Blanquart |
| 9,131,948 B2 | 9/2015 | Fang |
| 9,144,374 B2 | 9/2015 | Maurice, Jr. |
| 9,153,609 B2 | 10/2015 | Blanquart |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,226,647 B2 | 1/2016 | Sugawara |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,462,234 B2 | 10/2016 | Blanquart et al. |
| 9,486,296 B2 | 11/2016 | Mire et al. |
| 9,492,194 B2 | 11/2016 | Morgenstern Lopez et al. |
| 9,509,917 B2 | 11/2016 | Blanquart et al. |
| 9,510,853 B2 | 12/2016 | Aljuri et al. |
| 9,516,239 B2 | 12/2016 | Blanquart et al. |
| 9,522,017 B2 | 12/2016 | Poll et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,622,650 B2 | 4/2017 | Blanquart |

(56) References Cited

U.S. PATENT DOCUMENTS

| | | | |
|---|---|---|---|
| 9,629,521 B2 | 4/2017 | Ratnakar | |
| 9,641,815 B2 | 5/2017 | Richardson et al. | |
| 9,655,605 B2 | 5/2017 | Serowski et al. | |
| 9,655,639 B2 | 5/2017 | Mark | |
| 9,668,643 B2 | 6/2017 | Kennedy, II et al. | |
| 9,675,235 B2 | 6/2017 | Lieponis | |
| 9,700,378 B2 | 7/2017 | Mowlai-Ashtiani | |
| 9,706,905 B2 | 7/2017 | Levy | |
| 2002/0022762 A1 | 2/2002 | Beane et al. | |
| 2002/0138020 A1 | 9/2002 | Pflueger | |
| 2003/0083555 A1 | 5/2003 | Hunt et al. | |
| 2003/0171744 A1 | 9/2003 | Leung et al. | |
| 2003/0191474 A1 | 10/2003 | Cragg et al. | |
| 2004/0122446 A1 | 6/2004 | Solar | |
| 2004/0127992 A1 | 7/2004 | Serhan et al. | |
| 2004/0143165 A1 | 7/2004 | Alleyne | |
| 2004/0158286 A1 | 8/2004 | Roux et al. | |
| 2005/0075644 A1 | 4/2005 | DiPoto et al. | |
| 2005/0085692 A1 | 4/2005 | Kiehn et al. | |
| 2005/0090848 A1 | 4/2005 | Adams | |
| 2005/0187570 A1 | 8/2005 | Nguyen et al. | |
| 2005/0256525 A1 | 11/2005 | Culbert et al. | |
| 2006/0041270 A1* | 2/2006 | Lenker | A61B 17/3439 |
| | | | 606/198 |
| 2006/0052671 A1 | 3/2006 | McCarthy | |
| 2006/0074445 A1 | 4/2006 | Gerber et al. | |
| 2006/0200186 A1 | 9/2006 | Marchek et al. | |
| 2006/0206118 A1 | 9/2006 | Kim et al. | |
| 2006/0264895 A1 | 11/2006 | Flanders | |
| 2007/0049794 A1 | 3/2007 | Glassenberg et al. | |
| 2007/0055259 A1 | 3/2007 | Norton et al. | |
| 2007/0129634 A1 | 6/2007 | Hickey et al. | |
| 2007/0149975 A1 | 6/2007 | Oliver et al. | |
| 2007/0203396 A1 | 8/2007 | McCutcheon et al. | |
| 2007/0213716 A1 | 9/2007 | Lenke et al. | |
| 2007/0225556 A1 | 9/2007 | Ortiz et al. | |
| 2007/0255100 A1 | 11/2007 | Barlow et al. | |
| 2007/0260113 A1 | 11/2007 | Otawara | |
| 2007/0260184 A1 | 11/2007 | Justis et al. | |
| 2008/0015621 A1 | 1/2008 | Emanuel | |
| 2008/0033251 A1 | 2/2008 | Araghi | |
| 2008/0064921 A1 | 3/2008 | Larkin et al. | |
| 2008/0064928 A1 | 3/2008 | Otawara | |
| 2008/0081951 A1 | 4/2008 | Frasier et al. | |
| 2008/0139879 A1 | 6/2008 | Olson et al. | |
| 2008/0147109 A1 | 6/2008 | Kambin et al. | |
| 2008/0183189 A1 | 7/2008 | Teichman et al. | |
| 2008/0188714 A1 | 8/2008 | McCaffrey | |
| 2008/0242930 A1 | 10/2008 | Hanypsiak et al. | |
| 2008/0260342 A1 | 10/2008 | Kuroiwa | |
| 2009/0018566 A1 | 1/2009 | Escudero et al. | |
| 2009/0024158 A1 | 1/2009 | Viker | |
| 2009/0062871 A1 | 3/2009 | Chin et al. | |
| 2009/0105543 A1 | 4/2009 | Miller et al. | |
| 2009/0149857 A1 | 6/2009 | Culbert et al. | |
| 2009/0156898 A1 | 6/2009 | Ichimura | |
| 2009/0187080 A1 | 7/2009 | Seex | |
| 2009/0240111 A1 | 9/2009 | Kessler et al. | |
| 2009/0287061 A1 | 11/2009 | Feigenbaum et al. | |
| 2009/0318765 A1 | 12/2009 | Torii | |
| 2010/0004651 A1 | 1/2010 | Biyani | |
| 2010/0022841 A1 | 1/2010 | Takahashi et al. | |
| 2010/0076476 A1 | 3/2010 | To et al. | |
| 2010/0114147 A1 | 5/2010 | Biyani | |
| 2010/0151161 A1 | 6/2010 | Da Rolo | |
| 2010/0161060 A1 | 6/2010 | Schaller et al. | |
| 2010/0256446 A1 | 10/2010 | Raju | |
| 2010/0280325 A1 | 11/2010 | Ibrahim et al. | |
| 2010/0284580 A1 | 11/2010 | OuYang et al. | |
| 2010/0286477 A1 | 11/2010 | OuYang et al. | |
| 2010/0312053 A1 | 12/2010 | Larsen | |
| 2010/0317928 A1 | 12/2010 | Subramaniam | |
| 2011/0028791 A1 | 2/2011 | Marino et al. | |
| 2011/0054507 A1 | 3/2011 | Batten et al. | |
| 2011/0056500 A1 | 3/2011 | Shin et al. | |
| 2011/0073594 A1 | 3/2011 | Bonn | |
| 2011/0098628 A1 | 4/2011 | Yeung et al. | |
| 2011/0106261 A1 | 5/2011 | Chin et al. | |
| 2011/0112588 A1 | 5/2011 | Linderman et al. | |
| 2011/0125158 A1 | 5/2011 | Diwan et al. | |
| 2011/0130634 A1 | 6/2011 | Solitario, Jr. et al. | |
| 2011/0201888 A1 | 8/2011 | Verner | |
| 2011/0230965 A1 | 9/2011 | Schell et al. | |
| 2011/0257478 A1 | 10/2011 | Kleiner et al. | |
| 2011/0295070 A1 | 12/2011 | Yasunaga | |
| 2011/0319941 A1 | 12/2011 | Bar et al. | |
| 2012/0016192 A1 | 1/2012 | Jansen et al. | |
| 2012/0029412 A1 | 2/2012 | Yeung et al. | |
| 2012/0095296 A1 | 4/2012 | Trieu et al. | |
| 2012/0101338 A1 | 4/2012 | O'Prey et al. | |
| 2012/0111682 A1 | 5/2012 | Andre | |
| 2012/0116170 A1 | 5/2012 | Vayser et al. | |
| 2012/0157788 A1 | 6/2012 | Serowski et al. | |
| 2012/0209273 A1 | 8/2012 | Zaretzka et al. | |
| 2012/0221007 A1 | 8/2012 | Batten et al. | |
| 2012/0232350 A1 | 9/2012 | Seex | |
| 2012/0232552 A1 | 9/2012 | Morgenstern Lopez et al. | |
| 2012/0298820 A1 | 11/2012 | Manolidis | |
| 2012/0316400 A1 | 12/2012 | Vijayanagar | |
| 2013/0103067 A1 | 4/2013 | Fabro et al. | |
| 2013/0103103 A1* | 4/2013 | Mire | A61B 1/32 |
| | | | 606/86 A |
| 2013/0150670 A1 | 6/2013 | O'Prey et al. | |
| 2013/0150674 A1 | 6/2013 | Haig et al. | |
| 2013/0172674 A1 | 7/2013 | Kennedy, II et al. | |
| 2013/0172676 A1 | 7/2013 | Levy et al. | |
| 2013/0211202 A1 | 8/2013 | Perez-Cruet et al. | |
| 2013/0282022 A1 | 10/2013 | Yousef | |
| 2013/0289399 A1 | 10/2013 | Choi et al. | |
| 2013/0303846 A1 | 11/2013 | Cybulski et al. | |
| 2013/0304106 A1 | 11/2013 | Breznock | |
| 2014/0025121 A1 | 1/2014 | Foley et al. | |
| 2014/0066940 A1 | 3/2014 | Fang et al. | |
| 2014/0074170 A1 | 3/2014 | Mertens et al. | |
| 2014/0088367 A1 | 3/2014 | DiMauro et al. | |
| 2014/0142584 A1 | 5/2014 | Sweeney | |
| 2014/0148647 A1 | 5/2014 | Okazaki | |
| 2014/0163319 A1 | 6/2014 | Blanquart et al. | |
| 2014/0180321 A1 | 6/2014 | Dias et al. | |
| 2014/0194697 A1 | 7/2014 | Seex | |
| 2014/0215736 A1 | 8/2014 | Gomez et al. | |
| 2014/0221749 A1 | 8/2014 | Grant et al. | |
| 2014/0257332 A1 | 9/2014 | Zastrozna | |
| 2014/0257489 A1 | 9/2014 | Warren et al. | |
| 2014/0275793 A1 | 9/2014 | Song | |
| 2014/0275799 A1 | 9/2014 | Schuele | |
| 2014/0276840 A1 | 9/2014 | Richter et al. | |
| 2014/0276916 A1 | 9/2014 | Ahluwalia et al. | |
| 2014/0277204 A1 | 9/2014 | Sandhu | |
| 2014/0285644 A1 | 9/2014 | Richardson et al. | |
| 2014/0318582 A1 | 10/2014 | Mowlai-Ashtiani | |
| 2014/0336764 A1 | 11/2014 | Masson et al. | |
| 2014/0357945 A1 | 12/2014 | Duckworth | |
| 2014/0378985 A1 | 12/2014 | Mafi | |
| 2015/0018623 A1 | 1/2015 | Friedrich et al. | |
| 2015/0065795 A1 | 3/2015 | Titus | |
| 2015/0073218 A1 | 3/2015 | Ito | |
| 2015/0112398 A1 | 4/2015 | Morgenstern Lopez et al. | |
| 2015/0133727 A1 | 5/2015 | Bacich et al. | |
| 2015/0164496 A1 | 6/2015 | Karpowicz et al. | |
| 2015/0216593 A1 | 8/2015 | Biyani | |
| 2015/0223671 A1 | 8/2015 | Sung et al. | |
| 2015/0223676 A1 | 8/2015 | Bayer et al. | |
| 2015/0230697 A1 | 8/2015 | Phee et al. | |
| 2015/0238073 A1 | 8/2015 | Charles et al. | |
| 2015/0272694 A1 | 10/2015 | Charles | |
| 2015/0313585 A1 | 11/2015 | Abidin et al. | |
| 2015/0335389 A1 | 11/2015 | Greenberg | |
| 2015/0342621 A1 | 12/2015 | Jackson, III | |
| 2015/0366552 A1 | 12/2015 | Sasaki et al. | |
| 2015/0374213 A1 | 12/2015 | Maurice, Jr. | |
| 2016/0015467 A1 | 1/2016 | Vayser et al. | |
| 2016/0030061 A1 | 2/2016 | Thommen et al. | |
| 2016/0066965 A1 | 3/2016 | Chegini et al. | |

(56) References Cited

U.S. PATENT DOCUMENTS

| | | |
|---|---|---|
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0345952 A1 | 12/2016 | Kucharzyk et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110506 A1 | 4/2018 | Thommen et al. |
| 2018/0153592 A1 | 6/2018 | Larson |
| 2018/0214016 A1 | 8/2018 | Thommen et al. |
| 2018/0333061 A1 | 11/2018 | Pracyk et al. |
| 2019/0209154 A1 | 7/2019 | Richter et al. |
| 2019/0216454 A1 | 7/2019 | Thommen et al. |

FOREIGN PATENT DOCUMENTS

| | | |
|---|---|---|
| DE | 299 16 026 U1 | 11/1999 |
| EP | 0 537 116 A1 | 4/1993 |
| EP | 0 807 415 A2 | 11/1997 |
| GB | 2481727 A | 1/2012 |
| JP | 05-207962 A | 8/1993 |
| JP | 08-278456 A | 10/1996 |
| WO | 96/29014 A1 | 9/1996 |
| WO | 01/56490 A1 | 8/2001 |
| WO | 01/89371 A1 | 11/2001 |
| WO | 02/02016 A1 | 1/2002 |
| WO | 2004/103430 A2 | 12/2004 |
| WO | 2007/059068 A1 | 5/2007 |
| WO | 2008/121162 A1 | 10/2008 |
| WO | 2009/033207 A1 | 3/2009 |
| WO | 2010138083 A1 | 12/2010 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2016/201292 A1 | 12/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/043554, dated Nov. 19, 2015 (8 pages).
International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
International Preliminary Report on Patentability issued for Application No. PCT/US216/050022, dated Mar. 15, 2018.
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al, "Retrospective analysis and modifications of retractor systems for anterior odontoid screw fixation," Neurosurg Focus 16 (1)Article 14, 2004, pp. 1-4.
Extended European Search Report for Application No. 16843037.9; dated Mar. 14, 2019 (8 pages).
International Search Report for Application No. PCT/IB18/57367, dated Jan. 29, 2019, (4 pages).
International Search Report and Written Opinion for Application No. PCT/US18/21466 dated Jul. 3, 2018 (8 pages).
International Search Report and Written Opinion for Application No. PCT/US18/21449, dated Aug. 27, 2018 (14 pages).
International Search Report and Written Opinion for Application No. PCT/US18/47136, dated Jan. 23, 2019 (11 pages).
International Search Report and Written Opinion for Application No. PCT/US18/21454, dated Jul. 3, 2018 (16 pages).

\* cited by examiner

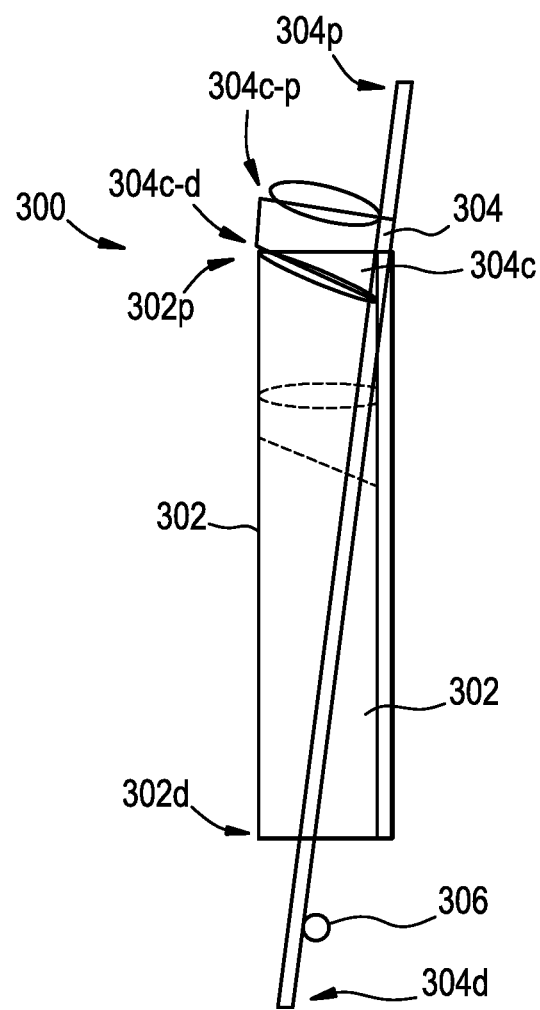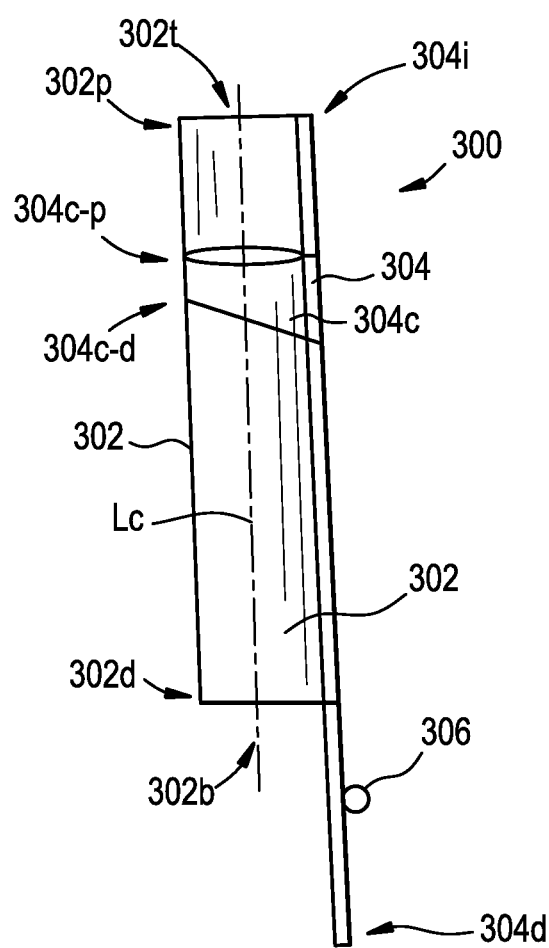
FIG. 4A
FIG. 4B

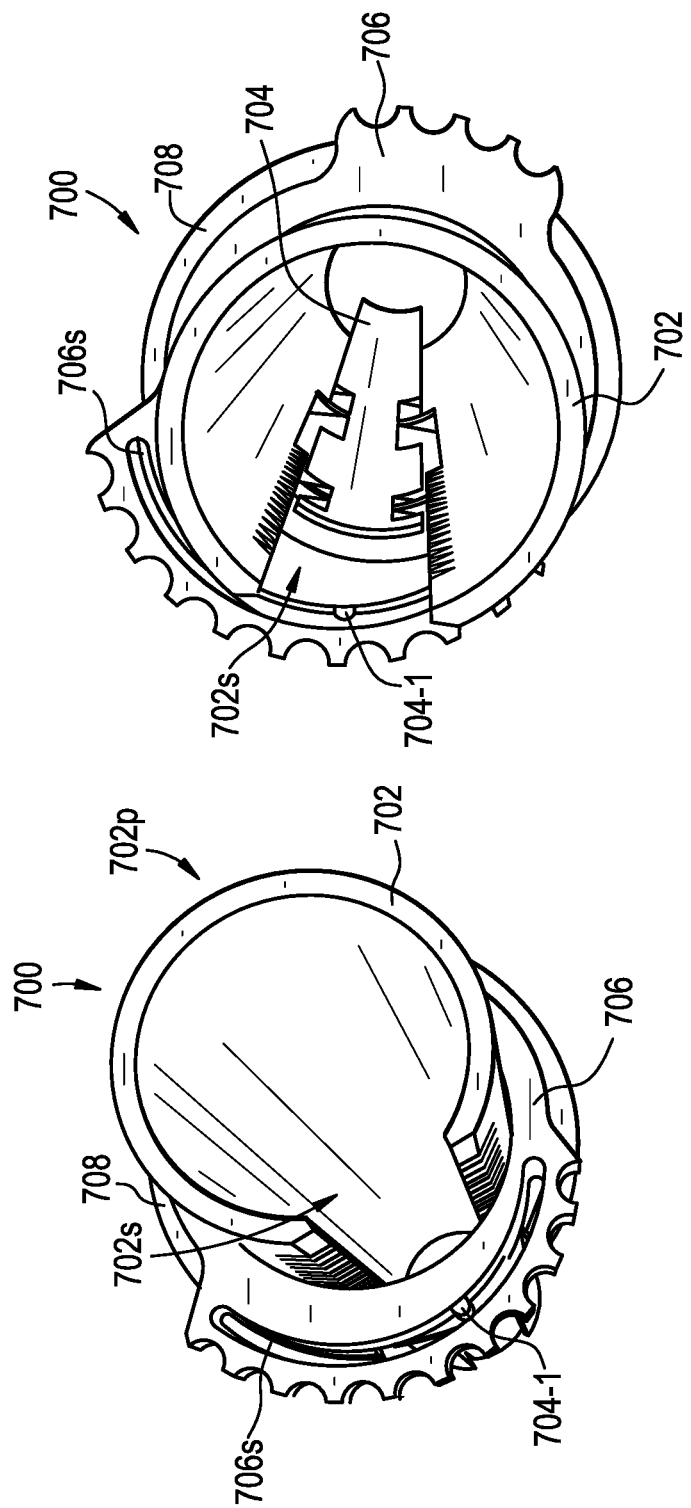

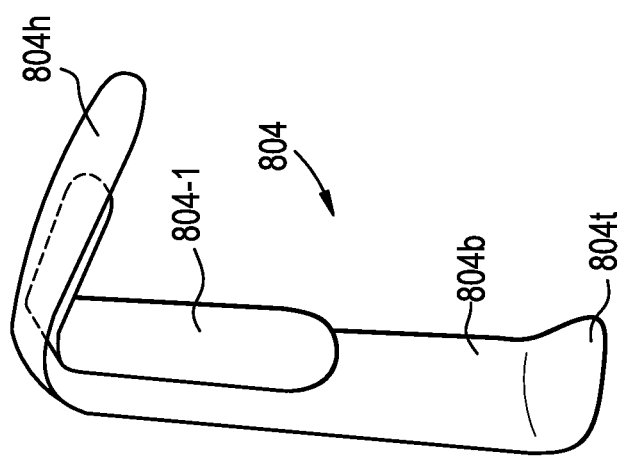
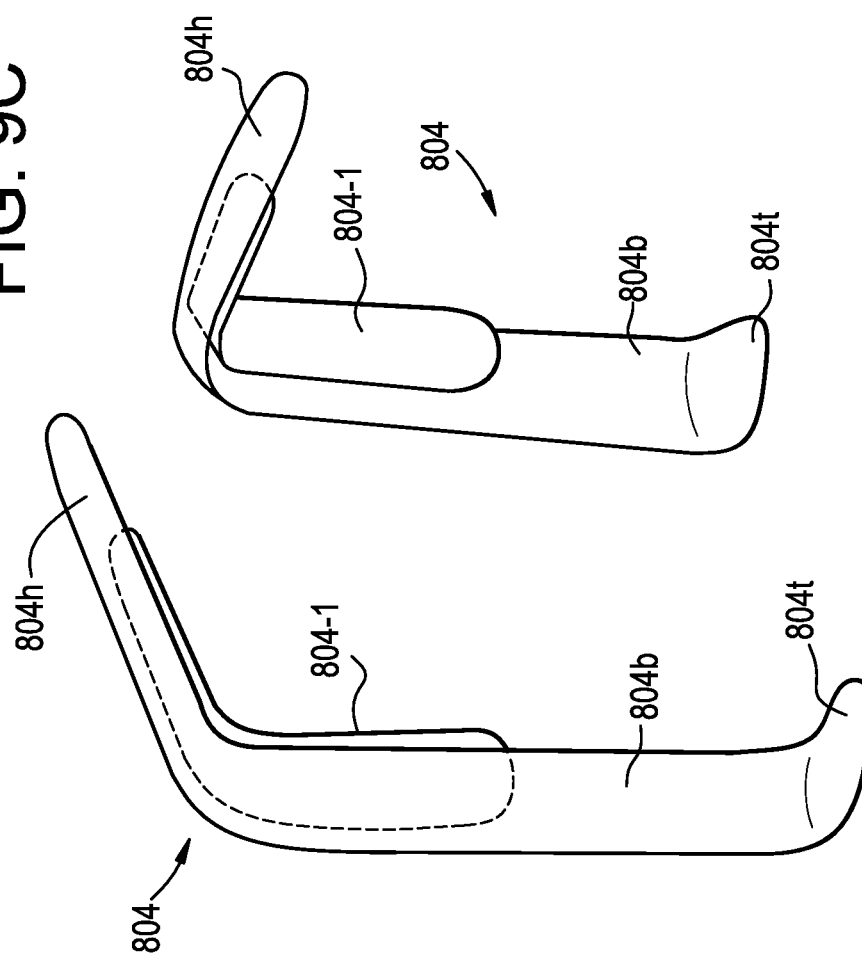
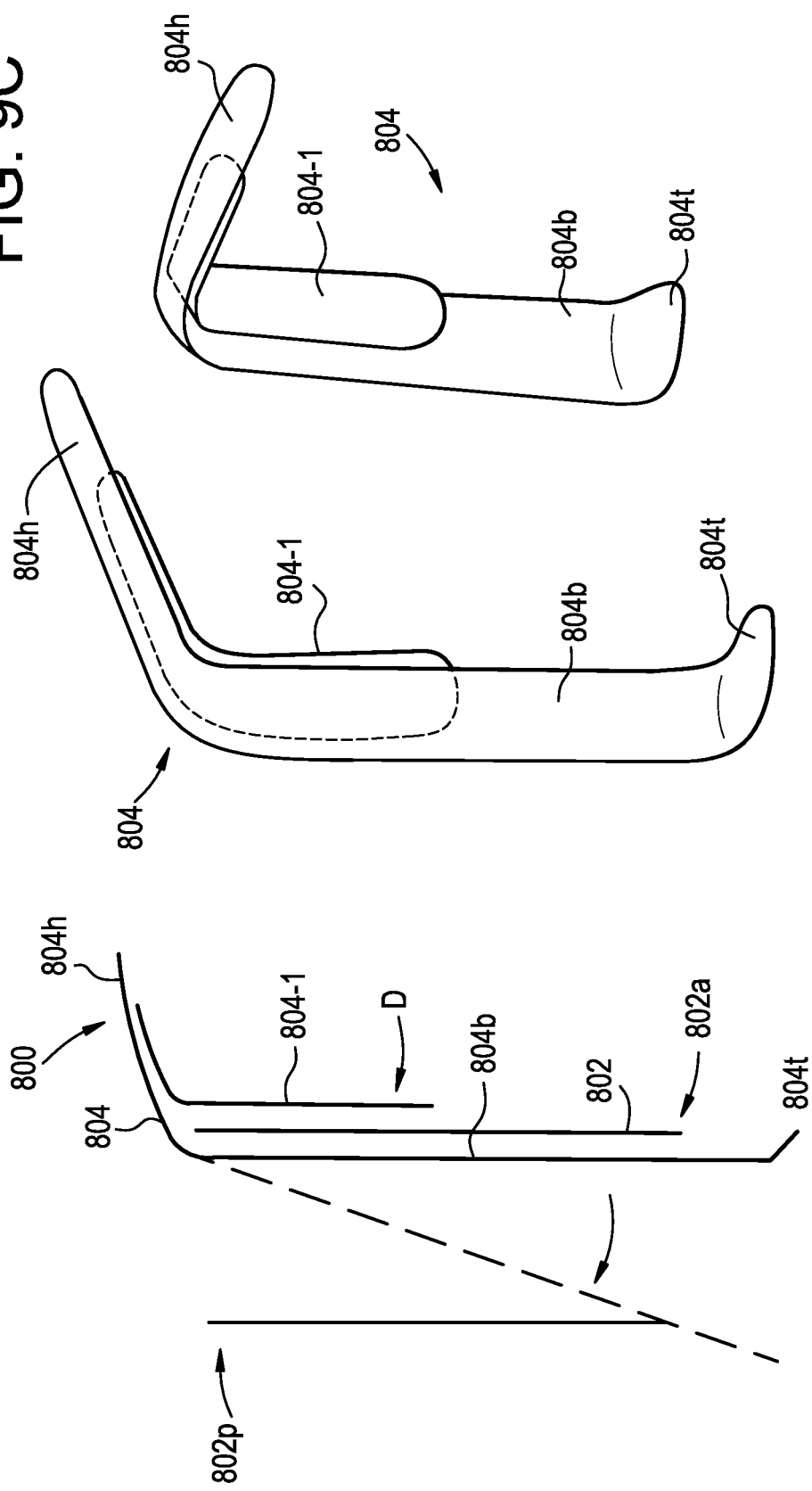

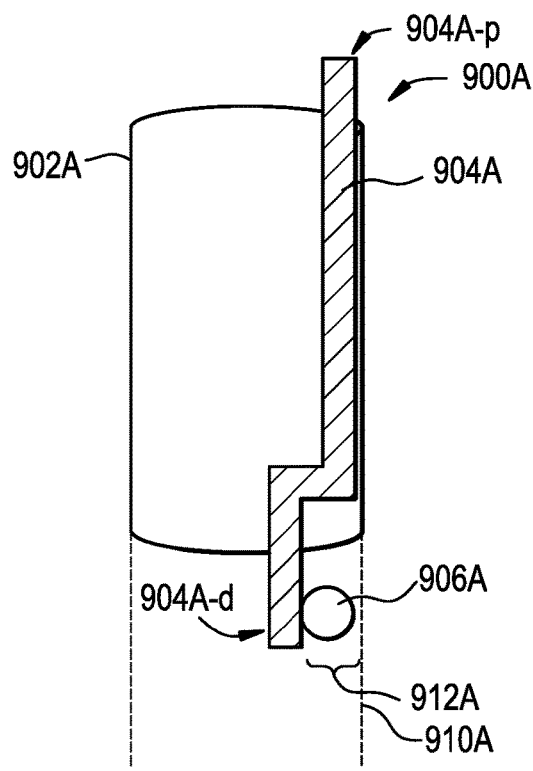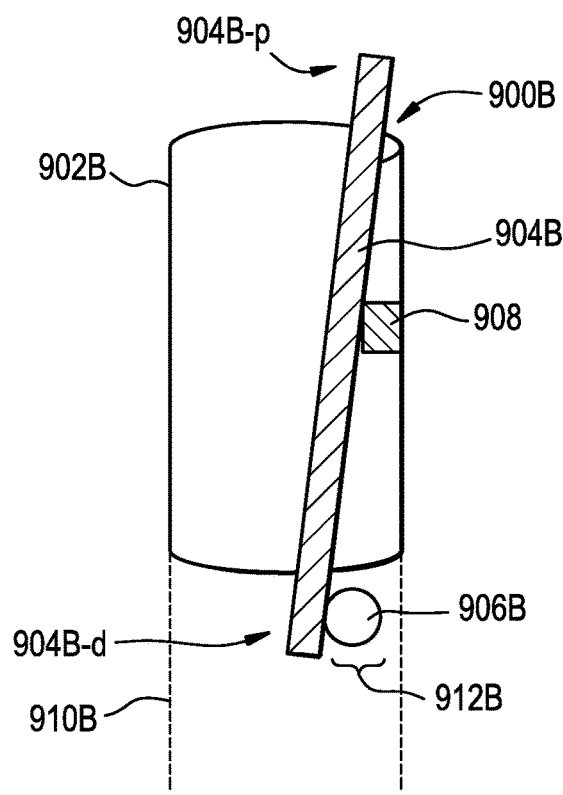

DEVICES AND METHODS FOR SURGICAL RETRACTION

CROSS-REFERENCE TO RELATED APPLICATIONS

The present application claims priority to U.S. Provisional Application No. 62/468,475 filed on Mar. 8, 2017, which is hereby incorporated by reference herein. The present application is also a continuation-in-part of U.S. application Ser. No. 15/437,792 filed on Feb. 21, 2017, which is a continuation-in-part of U.S. application Ser. No. 15/254,877 filed on Sep. 1, 2016, which claims priority to U.S. Provisional Application No. 62/214,297 filed on Sep. 4, 2015, each of which is hereby incorporated by reference herein.

FIELD

The present application relates to devices and methods for surgical retraction, e.g., for retracting nerves, blood vessels, or other structures to provide enhanced surgical access and safety.

BACKGROUND

Many surgical procedures involve accessing a working area within a patient via an access device such as a cannula, retractor, or the like. Surgical instruments, implants, or other objects can be passed through a working channel of the access device and into the working area of the patient. In some cases, nerve tissue, blood vessels, ducts, or other anatomical structures can be disposed in the path of the access device, can obstruct the working channel of the access device, or can require significant skill and dexterity to work around when performing surgery through the access device.

In minimally-invasive or microsurgical spinal surgery, for example, an access device can be used to provide access to the disc space. Depending on the positioning of the access device, a nerve, blood vessel, or other obstruction may lie across the path of the access device or a working channel thereof. It can be desirable to safely retract the obstruction, e.g., in a manner that is repeatable and consistent.

SUMMARY

Devices and methods for surgical retraction are described herein, e.g., for retracting nerve tissue, blood vessels, or other obstacles to create an unobstructed, safe surgical area. In some embodiments, a surgical access device can include an outer tube that defines a working channel through which a surgical procedure can be performed. A shield, blade, arm, or other structure can be manipulated with respect to the outer tube to retract an obstacle. For example, an inner blade can protrude from a distal end of the outer tube to retract obstacles disposed distal to the outer tube. The inner blade can be movable between a radially-inward position and a radially-outward position. The radially-inward position can allow insertion of the blade to the depth of the obstacle to position the obstacle adjacent to and radially-outward from the blade. Subsequent movement of the blade to the radially-outward position can retract the obstacle in a radially-outward direction. The blade can be manipulated remotely, e.g., from a proximal end of the access device or a location disposed outside of the patient. The blade can be manipulated in various ways, such as by rotating the blade relative to the outer tube, translating the blade longitudinally relative to the outer tube, sliding an expander along the blade, driving a wedge between the blade and the outer tube, actuating a cam mechanism of the access device, and/or pivoting the blade relative to the outer tube.

In some embodiments, surgical access devices can include an access tube and one or more obstacle retraction components configured to engage with each other and/or with the access tube. The access tube can have an opening formed therethrough for receiving, among other things, at least one of the one or more obstacle retraction components, or a portion of any of those components. The obstacle retraction components can include an obstacle shield configured to protrude through the opening of the access tube at the distal end of the access tube. A distal portion of the obstacle shield can be configured to apply a radially outward force on an obstacle. In some embodiments, radial movement of the obstacle can be achieved by inserting the surgical access device into the patient's anatomy, toward a surgical target area. While the obstacle shield is in a radially inward position, the access device can be advanced distally such that the obstacle is positioned adjacent to and radially-outward from the distal portion of the obstacle shield. The distal end of the obstacle shield can then be caused to move in a radially outward direction by a manipulation (e.g., rotation, push, pull, etc.) of the one or more obstacle retraction components, such that the obstacle is retracted in the radially outward direction. The radially outward position of the distal end of the obstacle shield can be maintained without further or continued manipulation of the one or more obstacle retraction components being needed, thereby facilitating hands-free retention of the retracted obstacle.

In some embodiments, an access device can include an outer tube having a distal end, a proximal end, and a working channel formed therethrough; and an inner shield disposed within the outer tube such that a distal end of the inner shield protrudes from a distal end of the outer tube, the inner shield being movable relative to the outer tube between a first position, in which the distal end of the inner shield is disposed in a radially-inward position, and a second position, in which the distal end of the inner shield is disposed in a radially-outward position; wherein the inner shield is movable between the first and second positions without rotating the inner shield relative to the outer tube about a longitudinal axis of the outer tube.

The inner shield can be configured to be maintained in the first or second positions without user input. The inner shield can be movable between the first and second positions by manipulating only a proximal end of the access device. The access device can include a hollow cylinder balloon or inflatable tube disposed in the working channel and configured to inflate and expand radially outward to retract the tissue in the radially outward direction.

In some embodiments, a surgical method can include inserting an access device into a patient; positioning an inner shield disposed through a working channel of the access device in a first position in which a distal end of the inner shield is moved radially-inward towards a central longitudinal axis of the working channel; with the inner shield in the first position, positioning an outer surface of the inner shield adjacent to tissue of the patient to be retracted, the outer surface protruding from a distal end of the working channel; without axially rotating the inner shield relative to the working channel, moving the inner shield to a second position in which the distal end of the shield is moved radially-outward away from the central longitudinal axis of the working channel, thereby retracting the tissue in a radially-outward direction.

The tissue of the patient can be selected from the group consisting of: nerves, blood vessels, ductile structures, dura, brain tissue, nerve roots, arteries, veins, pulmonary veins, ligaments, tendons, lymphatic vessels, organs, hollow structures, vocal cords, mucosa, tonsillar pillar, tongue base, and larynx. The method can include inserting an instrument through the working channel, the instrument being selected from the group consisting of: a drill guide, a suction instrument, a needle, a screw, a laser, a needle, a cautery device, and a scope. Inserting of the access device into the patient can include inserting the access device into the mandible, maxillary skeleton, larynx, or airway of the patient. Moving the inner shield can move tissue out of an access path extending to a vessel of the patient. The method can include inserting a catheter into the vessel via the working channel and the access path. The retracted tissue can include one or more of: a facial nerve during a parotid surgery, pulmonary vessels during a mediastinoscopy, and a laryngeal nerve during thyroid surgery. The distal end of the inner shield can be a blade for coring. The method can include inserting a screw, drill or other object through the access device, and the tissue of the patient can be a facial nerve, a nerve of the upper neck, a hypoglossal nerve, a lingual nerve, or a motor or sensory nerve.

In some embodiments, an access device can include an access tube having a distal end, a proximal end, and an access tube opening formed therethrough and configured to receive one or more obstacle retraction components; and one or more obstacle retraction components configured to apply a radially outward force on an obstacle to retract the obstacle in the radially outward direction, creating an obstacle free area, wherein the one or more obstacle retraction components includes at least an obstacle shield having a distal portion adjacent to a distal end, the distal portion adjacent to the distal end being configured to protrude through the opening of the access tube, wherein the radially outward force is applied by an outer surface of the distal portion of the obstacle shield, and wherein the radially outward direction is (i) measured relative to a longitudinal central axis of the access tube opening at the distal end of the access tube, and (ii) directed outward from the outer surface of the distal portion of the obstacle shield.

The one or more obstacle retraction components can be configured to be set to a static position in which the outer surface of the distal portion of the obstacle shield continuously applies the radially outward force on the obstacle. A proximal portion of the one or more obstacle retraction components can be manipulated to cause the application of the radially outward force on the obstacle, the manipulation including one or more of a rotation, distal pushing and proximal pulling of the one or more obstacle retraction components relative to the access tube.

In some embodiments, a method for providing a surgical safe area can include inserting an access device into an anatomy of a patient toward a surgical target area in the patient having nerve tissue therein, the access device comprising at least an access tube and one or more retraction components, the one or more retraction components including at least a shield; advancing the access device distally to or beyond the depth at which the nerve tissue is disposed within the patient, such that the nerve tissue is located outward from a distal portion of the shield adjacent to a distal end of the shield, the access device being advanced distally while the one or more retraction components are in a first position in which the distal end of the shield is disposed radially inward relative to its outermost radial position; causing the one or more retraction components to move from the first position to a second position in which the distal end of the shield is retracted in a radially outward direction relative to the radially inward position of the distal end of the shield in the first position; and setting the one or more retraction components in the second position such that the distal end of the shield is fixed in the retracted, radially outward direction for a continuous period of time, wherein the retraction of the distal end of the shield in a radially outward direction causes an outer surface of the distal portion of the shield to move the nerve tissue in the radially outward direction, wherein a surgical safe area includes at least an area, within the surgical target area, from which the nerve tissue is retracted.

The one or more retraction components can be set to the second position and the distal end of the shield can be fixed in the retracted, radially outward direction without further manipulation of the one or more retraction components during the continuous period of time. The one or more retraction components can be caused to be moved from the first position to the second position by applying one or more manipulations to the one or more retraction components relative to the access tube, the one or more manipulations including at least one of: a clockwise rotation, a counter-clockwise rotation, a distal pushing force, and a proximal pulling force. The method can include causing the one or more retraction components to be moved from the second position to the first position, such that (i) the distal end of the shield is moved in a radially inward direction, and (ii) the nerve tissue is allowed to move in the radially inward direction.

In some embodiments, an access device can include an access tube having an upper portion adjacent to a proximal end, a lower portion adjacent to a distal end, a curved elbow portion therebetween connecting the upper portion to the lower portion, and a working channel formed through the access tube from the distal end to the proximal end; and an inner blade disposed through the access tube of the access device, the inner blade being configured to apply a radially outward force on an obstacle to retract the obstacle in a radially outward direction to create an obstacle free area, wherein the inner blade includes: a first cylindrical portion having an outer circumference smaller than the circumference of the working channel at the proximal end of the access tube, such that the first cylindrical portion can slide within the working channel, a first blade portion connected to a distal end of the first cylindrical portion and extending longitudinally in a distal direction therefrom, and a second blade portion connected to the distal end of the first blade portion and extending longitudinally in a distal direction therefrom, the second blade portion having a distal end protruding through the distal end of the working channel.

The first blade portion and the second blade portion can be biased to a resting position in which the first blade portion and the second blade portion are at their outermost radial positions relative to a central longitudinal axis of the working channel. The curved elbow portion of the access tube can include an inside curve and an outside curve formed at diametrically opposed ends of the access tube, the inside curve having a shorter length than a length of the outside curve of the curved elbow portion. The curved elbow portion can be configured such that (i) the working channel at the upper portion is not coaxial with the working channel at the lower portion, and (ii) an inner surface of the access tube is not a continuous flat surface in a longitudinal direction from the proximal end to the distal end of the access tube. Rotating the inner blade in a first direction relative to the access tube can cause an outer surface of the first blade portion to contact the outside curve of the curved elbow, causing at least a portion of the first blade portion and at least the distal end of the second blade portion to move radially inward toward the central longitudinal axis of the working channel. Rotating the inner blade in a second direction opposite the first direction relative to the access tube can cause the outer surface of the first blade portion to contact the inside curve of the curved elbow, causing at least a portion of the first blade portion and at least the distal end of the second blade portion to move radially outward away from the central longitudinal axis of the working channel. The first blade portion can be longitudinally parallel to the inner surface of the access tube when the first blade portion is at its biased and outermost radial position.

In some embodiments, a surgical method can include inserting an access tube of an access device into a patient; positioning an inner blade through a working channel of the access tube in a first position in which: (i) a distal end of the inner blade is disposed radially inward toward a central longitudinal axis of the working channel; (ii) the distal end of the inner blade protrudes from a distal end of the working channel; (iii) an outer surface of the inner blade is disposed adjacent to tissue of the patient to be retracted, and (iv) the outer surface of a first blade portion of the inner blade is at least partially in contact with an outside curve of a curved elbow portion of the access tube, thereby causing a portion of an inner surface of the access tube to apply a radially inward force on the first blade portion; and rotating the inner blade relative to the access tube, from the first position to a second position in which the outer surface of the first blade portion of the inner blade is at least partially in contact with an inside curve of the curved elbow portion of the access tube, thereby causing: (a) the radially inward force applied on the first blade portion by the portion of the inner surface of the access tube to be reduced, (b) the distal end of the inner blade to retract radially outward away from the central longitudinal axis of the working channel, and (c) the tissue of the patient to be retracted in a radially outward direction.

In some embodiments, an access device can include an outer tube having a distal end, a proximal end, and a working channel formed therethrough; and an inner shield disposed through the outer tube such that a distal end of the inner shield protrudes from the distal end of the outer tube, wherein the inner shield is movable relative to the outer tube between a first position, in which a distal end of a blade of the inner shield is disposed in a radially inward position, and a second position, in which the distal end of the blade of the inner shield is disposed in a radially outward position, and wherein the inner shield is movable between the first position and the second position based on an amount of force applied upon a slotted cylinder of the inner shield by an inner surface of the outer tube, the force being configured to control the compression of the slotted cylinder about its circumference.

The blade of the inner shield can have a length larger than a length of the outer tube, the blade having at least a distal portion adjacent to the distal end of the blade, the distal portion of the blade being configured to retract an obstacle in a radially outward direction. The slotted cylinder: (i) can be attached to the blade, (ii) can be a cylindrical structure having a slot extending from a distal end to a proximal end of the slotted cylinder, and a slotted cylinder opening formed therethrough, (iii) can have an angled distal-facing surface such that a portion of the distal-facing surface of the slotted cylinder that contacts the blade forms an angle larger than 90 degrees with the blade, and (iv) can be formed of a resilient material that allows for its circumferential compression by the inner surface of the outer tube.

The length of a portion of the blade that extends distally from the distal-facing surface of the slotted cylinder can be larger than the length of the outer tube, such that the distal end of the blade protrudes through the outer tube opening at the distal end of the outer tube. A circumference of the slotted cylinder in the first position can be larger than the circumference of the opening of the outer tube at the proximal end of the outer tube. The circumference of the slotted cylinder in the second position can be smaller than the circumference of the opening of the outer tube. The blade can be made of a malleable material, such that the length of the handle portion can be adjusted to a desired size.

In some embodiments, a surgical method can include inserting an access tube of an access device into a patient; positioning an inner shield through a working channel of the access tube in a first position in which a distal portion of a slotted cylinder of the inner shield is inserted through the working channel of the access tube at a proximal end of the access tube, such that an outer surface of the slotted cylinder is not parallel to an inner surface of the access tube, thereby causing a distal end of the inner shield to be disposed radially inward toward a central longitudinal axis of the working channel and an outer surface of the inner shield to be disposed adjacent to tissue of the patient to be retracted; and moving the inner shield from the first position to the second position by distally sliding the inner shield through the working channel such that the slotted cylinder is inserted within the working channel, thereby causing: (i) the inner surface of the access tube to compress the slotted cylinder about its circumference, (ii) the distal end of the inner shield to retract radially outward away from the central longitudinal axis of the working channel, and (iii) the tissue of the patient to be retracted radially outward.

Compressing of the slotted cylinder about its circumference can cause (i) the outer surface of the slotted cylinder to contact the inner surface of the access tube and to be parallel thereto, and (ii) the distal end of the inner shield to retract radially outward. The method can include rotating the inner shield relative to the access tube while the inner shield is in the second position, such that a different portion of the tissue is retracted radially outward.

In some embodiments, an access device can include an outer tube having a distal end, a proximal end, and a working channel formed therethrough; a shield having a shield opening formed therethrough, and being configured to slide through the working channel, the shield including (a) a constant portion adjacent to a proximal end of the shield, and (b) an expandable portion adjacent to a distal end of the shield, the expandable portion including one or more arms extending distally at a radially inward angle, the arms being movable between a biased, first position in which a distal end of the arms is disposed in a radially inward direction, and a second position in which the distal end of the arms is moved in a radially outward direction; and an inner tube having an inner tube opening formed therethrough and being configured to slide within the shield opening, the inner tube comprising (a) a constant portion adjacent to a proximal end of the inner tube, and (b) an expander portion adjacent to a distal end of the inner tube and being distally angled in a radially inward direction at an angle larger than the radially inward angle of a distal end of the one or more arms.

The expander portion of the inner tube can be configured to slide within the shield opening at the expandable portion, thereby causing the arms to deflect from the first position to the second position. At least a portion of the expandable portion of the shield and at least a portion of the expander portion of the inner tube can protrude through the working channel at the distal end of the outer tube. One or more of the shield and the inner tube can be partial cylinders. The outer tube can include slots formed on an inner surface of the outer tube that are configured to receive the shield and the inner tube, thereby preventing the rotation of the shield and the inner tube relative to the outer tube when the shield and the inner tube are disposed within the working channel.

In some embodiments, a surgical method can include inserting an access tube of an access device into a patient; positioning a shield through a working channel of the access tube in a first position, in which arms of the shield protrude through a distal end of the access tube and are angled radially inward toward a central longitudinal axis of the working channel; and moving the shield from the first position to a second position, by distally advancing an inner tube through a shield opening formed between a proximal end and a distal end of the shield such that an outer surface of the distal end applies a radially outward force on the inner surface of the arms of the shield, thereby causing the arms of the shield to deflect radially outward.

The arms can gradually deflect radially outward in the radially outward direction as the expander portion is gradually advanced distally within the shield opening at the expandable portion of the middle tube.

In some embodiments, an access device can include an outer tube having a distal end, a proximal end, and a working channel formed therethrough; a shield including a longitudinal body and a flexible arm extending distally therefrom and protruding through a distal end of the working channel, the shield being movable between a first position, in which the flexible arm is disposed radially inward, and a second position, in which the flexible arm is disposed radially outward; and an expander including a longitudinal body slidably engaged with the shield in a longitudinal direction, the expander being configured to move the shield between the first and second positions by translating the expander longitudinally relative to the shield.

The shield can include a plurality of pins protruding from an outer surface of the longitudinal body of the shield. The shield can be removably fixed to the access tube by inserting the plurality of pins into respective keyholes of the outer tube and sliding the pins distally and proximally along corresponding slotted tracks of the outer tube into the removably fixed position.

In some embodiments, a surgical method can include inserting an access tube of an access device into a patient; positioning a shield through a working channel of the access tube in a first position, in which a flexible arm of the shield protrudes through a distal end of the access tube and is angled radially inward toward a central longitudinal axis of the working channel; and moving the shield from the first position to a second position, by distally advancing an expander through the working channel of the access tube, relative to the shield, such that the expander portion contacts at least a portion of the flexible arm of the shield, thereby causing the shield to move radially outward.

The flexible arm can gradually move toward the second position as an increasing length of the expander portion is in contact with the flexible arm of the shield by the distal advancement of the expander portion.

In some embodiments, an access device can include an outer tube having a distal end, a proximal end, and a working channel formed therethrough; a shield being configured to slide through the working channel and extending longitudinally such that a distal end of the shield protrudes through the working channel at the distal end of the outer tube, the shield having a longitudinal slot formed through an inner and outer surface of the shield and extending distally from a proximal end of the of the shield, wherein the shield is movable from a first position in which a distal end of the shield is disposed radially inward, and a second position in which the distal end of the arm is moved in a radially outward direction; and a wedge including a blade portion and a wedging tip formed at a distal end of the wedge, the wedge being positioned relative to the shield such that (i) a proximal end of the wedge is positioned at the inner surface of the shield, (ii) the blade portion penetrates through the longitudinal slot of the shield, and (iii) the wedging tip is positioned at the outer surface of the shield.

The wedging tip can have a width larger than the width of the longitudinal slot. The blade portion of the wedge can have a width smaller than the width of the longitudinal slot. The wedging tip can be slidably disposed between the obstacle shield and the access tube. The shield can be formed of a material that enables at least a portion of the obstacle shield at its distal end to move in a radially inward direction.

In some embodiments, a surgical method can include inserting an access tube of an access device into a patient; positioning a shield through a working channel of the access tube in a first position, in which a distal end of the shield protrudes through a distal end of the access tube and is angled radially inward toward a central longitudinal axis of the working channel; and moving the shield from the first position to a second position, by proximally retracting a wedge relative to the shield such that a distal end of the shield slides between the shield and the access tube, thereby causing a force to be applied on the outer surface of the shield and the distal end of the shield to move in a radially outward direction.

In some embodiments, an access device can include an outer tube having a distal end, a proximal end, a working channel formed therethrough, and a longitudinal slot extending distally from the proximal end, the longitudinal slot penetrating through an inner surface and an outer surface of the outer tube; a shield including a longitudinal body and a pin protruding from a proximal end of the shield, the shield being disposed through the longitudinal slot of the outer tube such that the proximal end of the shield is positioned external to the outer surface of the outer tube and the distal end of the shield is positioned internal to the inner surface of the outer tube; and a cam mechanism having a cam opening formed therethrough, through which the outer tube is disposed, the cam mechanism further including a circumferential slot formed through a proximal-facing surface and a distal-facing surface of the cam mechanism, the circumferential slot being configured to receive the pin of the shield and having an increasing radius relative to a center of the cam opening such that one end the shield is positioned further away from the center of the cam opening than the other end of the obstacle shield.

Rotation of the cam mechanism relative to the outer tube can cause the pin of the shield to slide along the circumferential slot of the cam mechanism. The circumferential slot can be formed around less than the entire circumference of the cam mechanism. The distal portion of the shield can move in a radially inward direction as the pin is driven in a radially outward direction by the circumferential slot of the cam mechanism. The shield can pivot about a portion of the outer tube along the longitudinal slot, causing the movement of the distal portion of the shield in the radially inward direction.

In some embodiments, a surgical method can include inserting an access tube of an access device into a patient; disposing a shield in a first position, in which a distal end of the shield is positioned radially inward toward a central longitudinal axis of a working channel of the access tube; and moving the shield from the first position to a second position, by rotating a cam mechanism relative to the outer tube such that a pin of the shield is driven along a circumferential slot of the cam mechanism, from a first end to a second end, the second end being positioned further from the center of the cam opening than the first end such that (i) the proximal end of the shield is moved in the radially outward direction, (ii) the distal end of the shield is moved in the radially inward direction, and (iii) the shield pivots about a longitudinal slot formed in the access tube.

The cam mechanism can be rotated counterclockwise to drive the pin of the shield from the first end to the second end of the circumferential slot. The cam mechanism can be rotated clockwise to drive the pin of the shield from the second end to the first end of the circumferential slot.

In some embodiments, an access device can include an outer tube having a distal end, a proximal end, and a working channel formed therethrough; and a shield being having a longitudinal body, a handle portion formed at a proximal end of the longitudinal body, the handle portion curving or bending away from the longitudinal body, and a finger portion connected to a distal-facing surface of the handle portion and extending distally, the finger portion being curved or bent based on the curvature or degree of bending of the handle, wherein the shield is movable between a first position, in which the shield is disposed in a radially outward position, and a second position, in which the shield is moved toward a central longitudinal axis of the working channel.

The finger portion can be connected to the inferior surface of the handle portion at a region of the handle away from a proximal end of the handle portion.

In some embodiments, a surgical method can include inserting an access tube of an access device into a patient; positioning a shield through a working channel of the access tube in a first position in which a distal force is applied on a proximal-facing surface of a handle portion of the shield, such that a distal end of a longitudinal body of the shield and a distal end of a finger portion of the shield are caused to move in a radially inward direction; and relaxing the distal force to move the shield from the first position to a second position in which the distal end of the shield is retracted in a radially outward direction relative to the radially inward position of the distal end of the shield in the first position.

Relaxing the distal force applied on the proximal-facing surface of the handle portion can cause the longitudinal body and the handle portion of the shield to be retracted to their biased position.

BRIEF DESCRIPTION OF DRAWINGS

This disclosure will be more fully understood from the following detailed description taken in conjunction with the accompanying drawings, in which:

FIG. 4A is a sectional side view of another exemplary embodiment of an obstacle retracting access device in a radially inward configuration;

FIG. 4B is a sectional side view of the access device of FIG. 4A in a radially outward configuration;

FIG. 8D is a perspective view of the proximal end of the access device of FIG. 8A;

FIG. 8E is another perspective view of the proximal end of the access device of FIG. 8A;

FIG. 9A is a sectional side view of another exemplary embodiment of an obstacle retracing access device;

FIG. 9B is a perspective view of an exemplary embodiment of a shield of the access device of FIG. 9A;

FIG. 9C is another perspective view of the shield of FIG. 9B;

FIG. 10A is a sectional side view of another exemplary embodiment of an obstacle retracing access device having an offset nerve shield; and FIG. 10B is a sectional side view of another exemplary embodiment of an obstacle retracing access device having an offset nerve shield.

DETAILED DESCRIPTION

Figure 1:
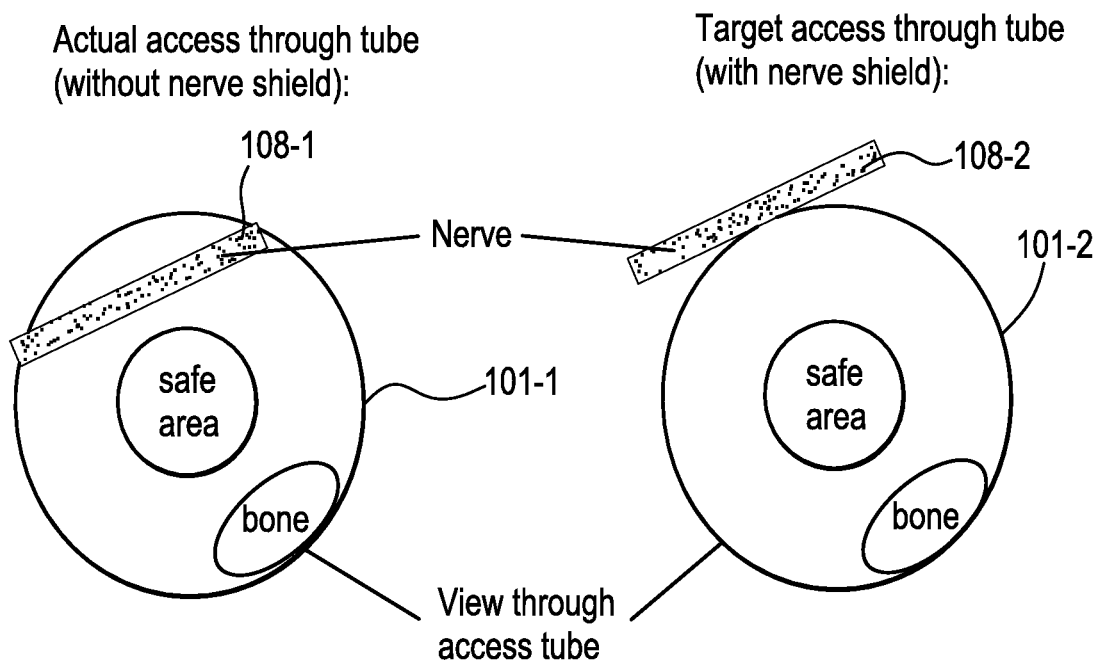
FIG. 1 is a diagram illustrating the retraction of nerve tissue from surgical safe areas.

Devices and methods for surgical retraction are described herein, e.g., for retracting nerve tissue, blood vessels, or other obstacles to create an unobstructed, safe surgical area. In some embodiments, a surgical access device can include an outer tube that defines a working channel through which a surgical procedure can be performed. A shield, blade, arm, or other structure can be manipulated with respect to the outer tube to retract an obstacle. For example, an inner blade can protrude from a distal end of the outer tube to retract obstacles disposed distal to the outer tube. The inner blade can be movable between a radially-inward position and a radially-outward position. The radially-inward position can allow insertion of the blade to the depth of the obstacle to position the obstacle adjacent to and radially-outward from the blade. Subsequent movement of the blade to the radially-outward position can retract the obstacle in a radially-outward direction. The blade can be manipulated remotely, e.g., from a proximal end of the access device or a location disposed outside of the patient. The blade can be manipulated in various ways, such as by rotating the blade relative to the outer tube, translating the blade longitudinally relative to the outer tube, sliding an expander along the blade, driving a wedge between the blade and the outer tube, actuating a cam mechanism of the access device, and/or pivoting the blade relative to the outer tube.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. Further, to the extent features or steps are described as being, for example, "first" or "second," such numerical ordering is generally arbitrary, and thus such numbering can be interchangeable.

The present disclosure includes some illustrations and descriptions that include prototypes or bench models. A person skilled in the art will recognize how to rely upon the present disclosure to integrate the techniques, devices, and methods provided for into a product, such as a consumer ready, warehouse-ready, or operating room ready surgical device.

A person skilled in the art will appreciate that the present disclosure has application in conventional endoscopic, minimally-invasive, and open surgical procedures as well application in robotic-assisted surgery.

Exemplary embodiments of the present disclosure provide access devices, and more specifically, access devices such as surgical access devices configured to retract obstacles such as nerve tissue to create safe surgical areas. An access device can include an access tube and one or more obstacle retraction components. For example, an access device can include an outer access tube and an inner shield or blade disposed within the access tube for retracting tissue. The one or more retraction components can be configured to engage with each other and/or with the access tube to cause radial movement of obstacles in an inward and/or outward direction relative to an opening or working channel of the access tube. The access tube opening can be formed through the body of the access tube, extending through the distal and proximal ends of the access tube, and can be configured to receive a retraction component. The retraction component can be or can include a shield or blade. The retraction component can have a sufficient length so as to protrude at least in part from the distal end of the access tube. The retraction component can be configured to apply a radially-directed force on the obstacle to be moved.

In exemplary embodiments of the present disclosure, radial movement of the obstacle to create a safe area is achieved by inserting the access device into a patient in the direction of a target surgical area. While the retraction component of the access device is in a position in which the distal end of the retraction component is disposed radially inward, the access device is advanced distally such that the distal end of the retraction component is positioned (1) at or beyond the depth of the obstacle to be moved, and (2) radially-inward from the obstacle. The retraction component is then manipulated to move the distal end of the retraction component in a radially outward direction. The radially outward movement of the distal end of the retraction component causes an outer surface of the retraction component to apply a radially outward force on the obstacle, moving it away from a central longitudinal axis of the access tube or a working channel thereof. The surgical safe area, which can be concentric with the opening of the access tube, is thereby expanded such that its outside border or circumference corresponds to the radially outward position of the distal end of the retraction component and/or the obstacle. Operating within an expanded surgical safe area is thus enabled. Moreover, the position of the retraction component can be fixed such that the obstacle can be maintained in a retracted position without requiring further manipulation thereof, e.g., in a "hands free" manner.

It should be understood that the access tubes and retraction components described herein can have any shape, dimension and/or or other characteristics. Moreover, the shape, dimension and/or other characteristics of the access tubes and retraction components can vary within a single access tube or component. For instance, the diameter of an access tube at a proximal end can be different than the diameter of the access tube at a distal end, such that the access tube narrows from one end to the other. It should also be understood that while cylindrical access tubes having round openings are generally described herein, the access tubes can have square, triangular, oval, elliptical, or any other shaped openings. Access tubes can include cannulas, multi-blade or slotted retractors, and the like. The shape, dimension and/or other characteristics of the access tubes and retraction components can vary based on the shape, dimension and/or characteristics of other of the access tubes and retraction components with which they engage. For instance, a retraction component can have a curved body corresponding to the curvature of the access tube, such that when the retraction component is disposed within the access tube and in contact with an inner surface of the access tube, the retraction component can make intimate contact with the inner surface.

As shown in FIG. 1, an access device with one or more retraction components, e.g., an inner shield, can be used to retract a nerve away from a safe area, thereby enlarging the safe area or providing safer access to the safe area. Area 101-1 and 101-2 represent a surgical working area in a patient's body, as viewed from a top-down or outside-in perspective through an access tube inserted into the patient's body. Working area 101-1 is the area having a nerve running therethrough while working area 101-2 is the area having the same nerve 108-1 and 108-2 retracted therefrom. As can be seen in connection with working area 101-2, with the nerve 108-2 retracted radially outward or away from the safe area or working area, it is possible to access the original safe area with fewer obstructions or to enlarge the safe area to a have a larger diameter (e.g., as large as the working area projected by the opening of the access tube). Whereas, on the other hand, working within the safe area of working area 101-1 having the nerve running therethrough increases the risk of damaging the nerve 108-1 due to its proximity to the safe area.

First Embodiment

FIGS. 2A to 2H (collectively referred to as "FIG. 2") illustrate one exemplary embodiment of a surgical access device 200 configured to radially move nerve tissue and other obstacles, to provide enhanced surgical access. Described in connection with FIGS. 2A to 2H are examples of the surgical access device 200 having multiple retraction components, e.g., multiple blades 204. On the other hand, described in connection with FIGS. 3A to 3H (collectively referred to as "FIG. 3") are examples of the surgical access device 200 including only a single retraction component, e.g., a single blade 204. It should be understood that descriptions of embodiments in which the surgical access device includes a single blade can similarly be applied to and/or function with surgical access devices having multiple blades, and that the access device can include any number of blades.

In some embodiments, the surgical access device 200 is used during surgery to move nerve tissue radially outward, in order to protect or shield the nerve tissue and allow a safe surgical area within the patient's body to be safely accessed or enlarged.

As shown in FIGS. 2 and 3, the surgical access device 200 can include an outer access tube 202 and one or more inner blades 204 (also referred to herein as "inner shield"). The access tube can include a body having a cylindrical exterior surface and a non-cylindrical interior surface. The access tube can extend between proximal and distal ends 202p, 202d. The access tube can include an opening or hole formed therethrough, through its proximal end 202p its distal end 202d, to define a working channel. The access tube 202 can have a closed circumference or perimeter. The access tube 202 can have an inner surface 202i and an outer surface 202o. The inner surface 202i can define the opening or working channel through the access tube 202, extending through proximal end 202p and the distal end 202d. It should be understood that portions of the body of the access tube 202, including its inner and outer surfaces 202i and 202o, can also be referred to as its walls.

As can be seen in, for example, FIGS. 2B, 2E, 2F and 2H, the access tube 202 can include two cylindrical or tubular portions: an upper portion 202-1 extending distally from the proximal end 202p, and a lower portion 202-2 extending proximally from the distal end 202d, which are joined by an elbow or elbow portion 202-3. Although they are independently referred to as three portions 202-1, 202-2 and 202-3, the access tube 202 can be a single, cohesive or monolithic unit. In other words, the access tube 202 can be manufactured as a single access tube. Though, in some embodiments, the portions 202-1, 202-2 and 202-3 can be provided separately (e.g., distinctly manufactured) and later combined, joined, attached, welded, or the like into the access tube 202.

Portions 202-1 and 202-2 can each have respective proximal and distal ends 202-1p and 202-1d, and 202-2p and 202-2d. The portions 202-1 and 202-2 can be connected to each other at or via the elbow 202-3. The distal end 202-1d of the upper portion 202-1 can connect to a proximal end 202-3p of the elbow, and the proximal end 202-2p of the lower portion 202-2 can connect to a distal end 202-3d of the elbow 202-3. An elbow on the access tube 202 refers to a portion at which the outer surface 202o and/or the inner surface 202i of the access tube 202 does not form a continuous flat or cylindrical surface along its length (e.g., along a longitudinal or proximal-distal direction), resembling the shape of a bent human elbow. That is, the upper and lower portions 202-1 and 202-2 of the access tube 202 can be non-coaxial with one another. A central longitudinal axis of the portion of the working channel defined in the upper portion 202-1 of the access tube 202 can extend at an oblique angle with respect to a central longitudinal axis of the portion of the working channel defined in the lower portion 202-2. The working channel of the access tube 202 can thereby define an inside curve $C_i$ and an outside curve $C_o$.

The inside and outside curves $C_i$ and $C_o$ can be positioned at the same or substantially similar lengthwise positions of the access tube 202. The inside and outside curves $C_i$ and $C_o$ can be positioned at diametrically opposed sides of the access tube 202. The inside and outside curves $C_i$ and $C_o$ can be curved such that they are convex and concave, respectively. The length and degree of curvature of the inside and outside curves $C_i$ and $C_o$ can vary as deemed optimal or necessary. The inside curve $C_i$ can have a length and/or degree of curvature that is smaller than the length and/or degree of curvature of the outside curve $C_o$. As described in further detail below, the inside and outside curves $C_i$ and $C_o$ can be formed such that, when an inner blade is in a position in which its proximal end is disposed along the inner surface of the inside curve $C_i$, its remaining length is disposed in contact or proximate to the inner surface of the access tube 202, such that a distal end of the blade is disposed in a radially-outward position. On the other hand, when the inner blade is in another position in which its proximal end is disposed along the inner surface of the outside curve $C_o$, its remaining length is disposed away from the inner surface of the access tube, such that a distal end of the blade is disposed in a radially-inward position.

Figure 2A:
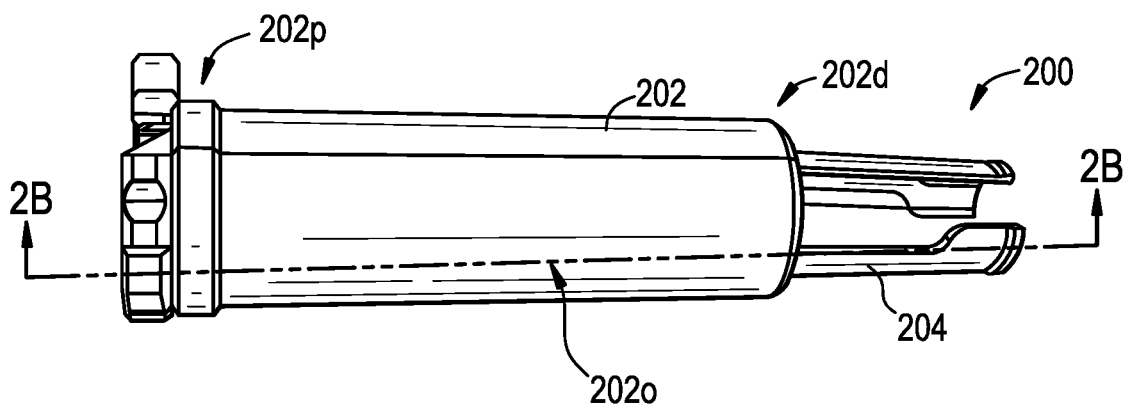
FIG. 2A is a side view of one exemplary embodiment of an obstacle retracting access device.
Figure 2B:
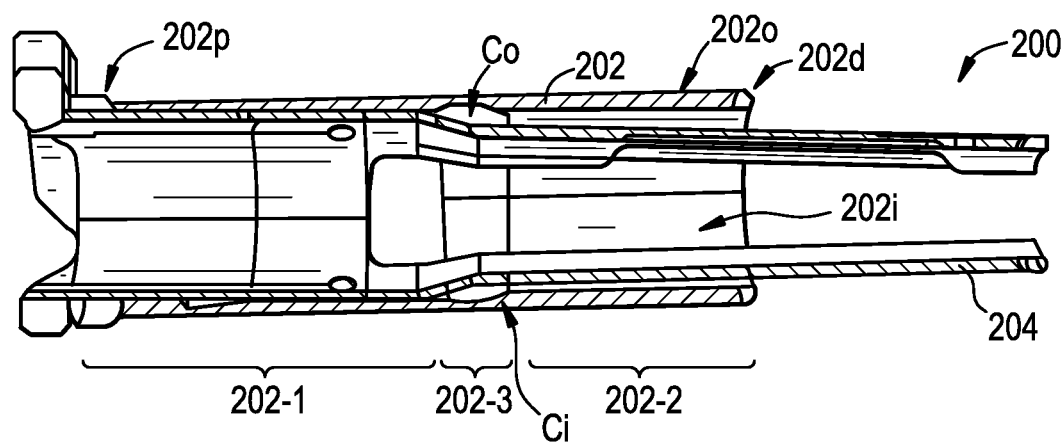
FIG. 2B is cross-sectional side view of the access device of FIG. 2A taken along the line A-A.
Figure 2C:
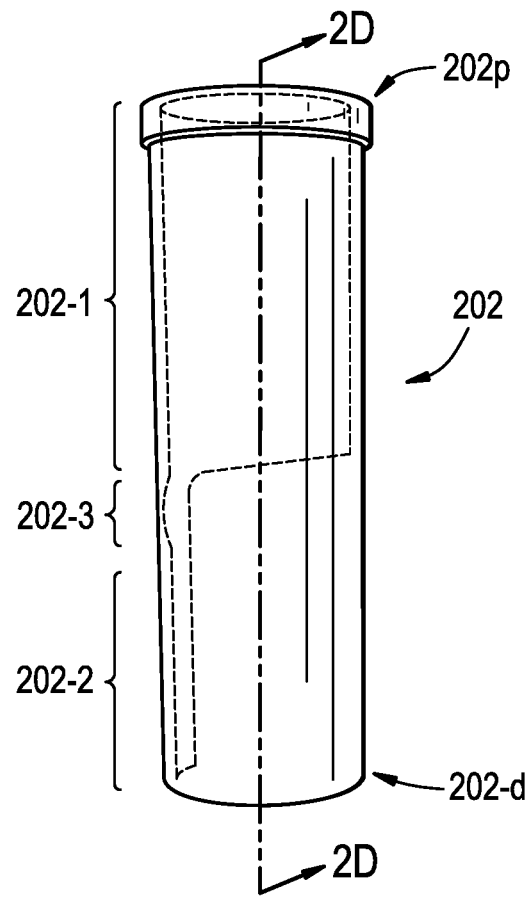
FIG. 2C is a side view of an exemplary embodiment of an access tube of the access device of FIG. 2A.
Figure 2D:
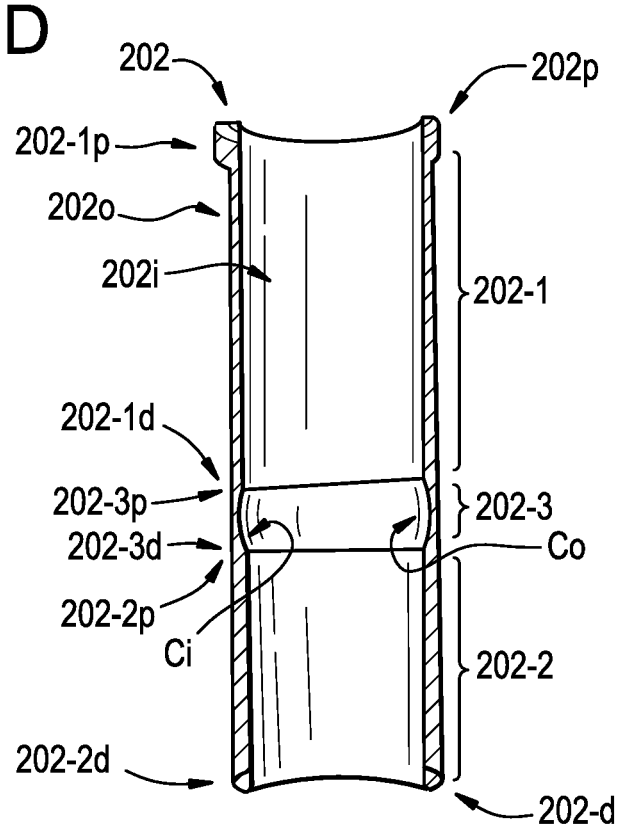
FIG. 2D is a cross-sectional side view of the access tube of FIG. 2C taken along the line B-B.
Figure 2E:
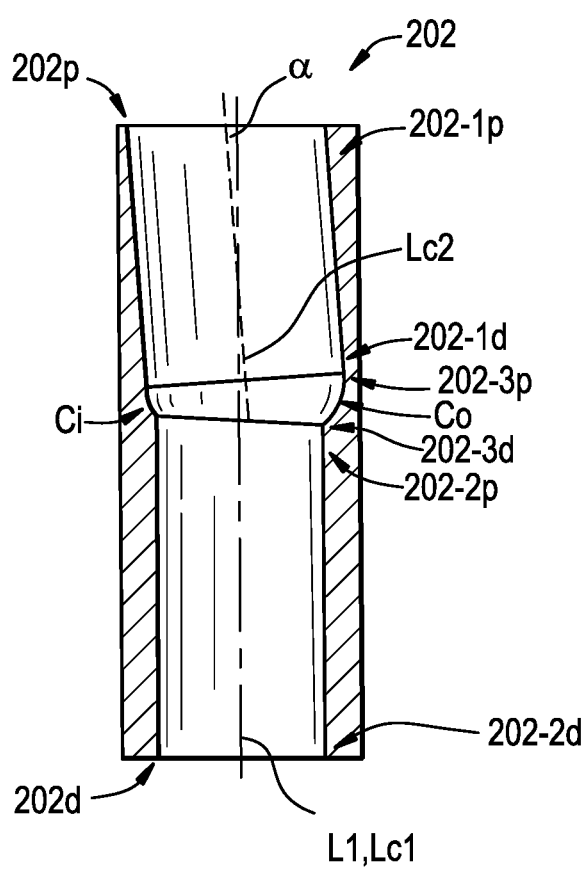
FIG. 2E is a sectional side view of an exemplary embodiment of an access tube of the access device of FIG. 2A.
Figure 2F:
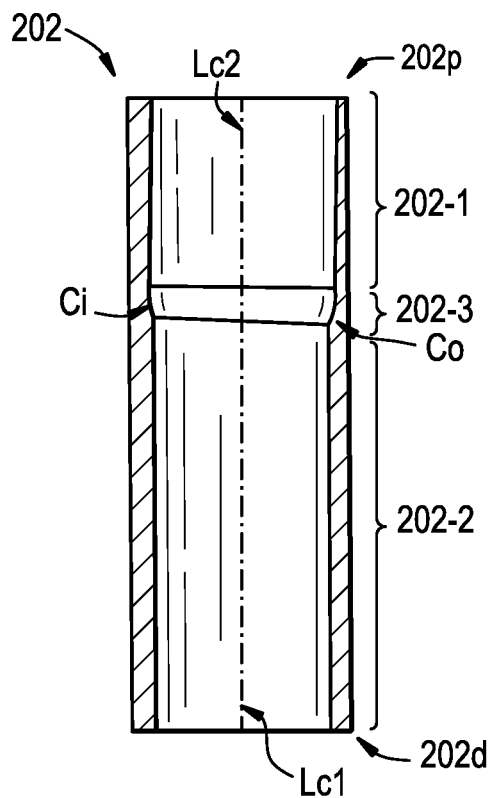
FIG. 2F is a sectional side view of an exemplary embodiment of an access tube of the access device of FIG. 2A.
Figure 2G:
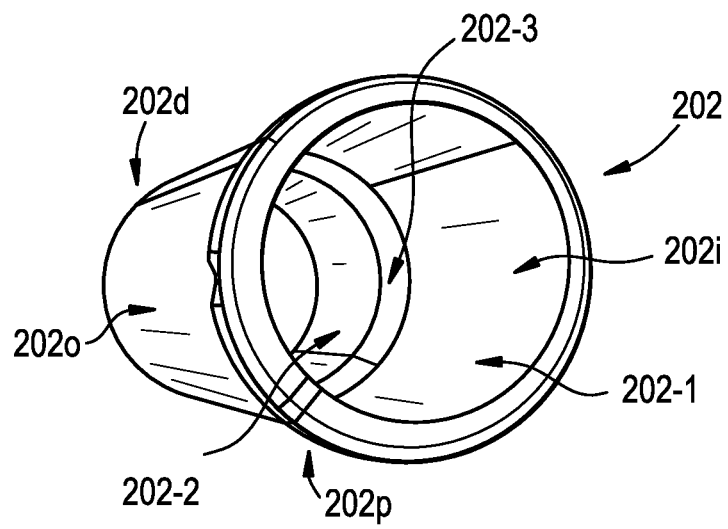
FIG. 2G is a perspective view of an exemplary embodiment of an access tube of the access device of FIG. 2A.
Figure 2H:
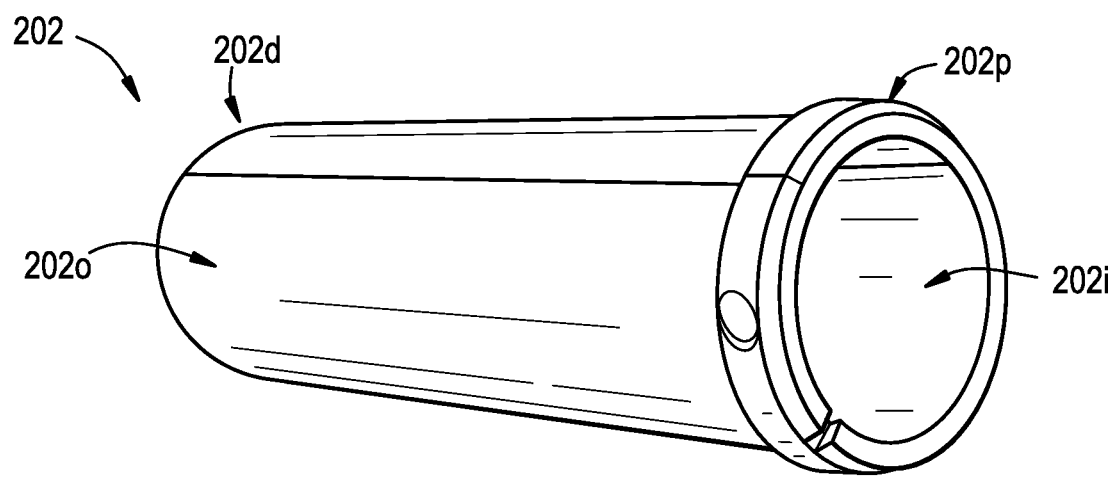
FIG. 2H is another perspective view of the access tube of FIG. 2G.

As shown, the upper portion 202-1 can be angled relative to the lower portion 202-2. More specifically, as illustrated in FIG. 2E, the access tube 202 can have a longitudinal axis $L_1$ that is the same as the central longitudinal axis $L_{C1}$ of the lower portion 202-2 running in a distal-proximal direction along the center of the opening formed through the lower portion 202-2. The upper portion 202-1 can have a central longitudinal axis $L_{C2}$ running in a distal-proximal direction along the center of the opening formed through the upper portion 202-1. The upper portion 202-1 can be angled such that an angle at formed by the central longitudinal axes $L_{C1}$ and $L_{C2}$ is not equal to 180 degrees. In some embodiments, the angle at is an oblique angle or an angle greater than 0 degrees. FIG. 2F also illustrates the angling of the upper and lower portions 202-1 and 202-2 relative to the central longitudinal axes $L_{C1}$ and $L_{C2}$ of the lower portion 202-2 and the upper portion 202-1, respectively. As described in further detail below, such angling of the upper and/or lower portions 202-1 and 202-2 can enable an inner blade 204 to be activated (e.g., deflected, bent, deformed, moved, etc.) in order to retract or radially move nerve tissue or other obstacles.

The access tube 202 and/or its upper and lower portions 202-1 and 202-2, can have openings of various diameters, for instance, as deemed necessary or optimal to access certain target regions in a patient's body, enable the insertion of various instruments or devices therethrough, and so forth. The diameter of the openings of the upper and lower portions 202-1 and 202-2 can be different from each other. For example, the opening of the upper portion 202-1 can have a larger diameter than the opening of the lower portion 202-2.

Figure 3A:
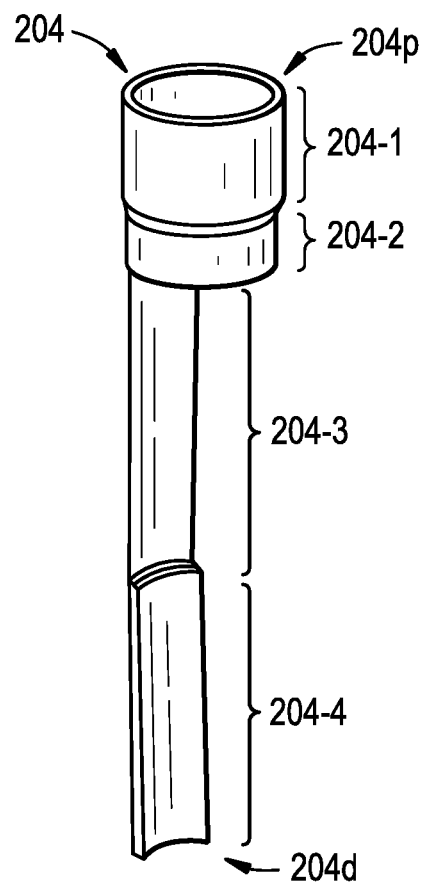
FIG. 3A is a side view of an exemplary embodiment of an inner blade of the access device of FIG. 2A.

The opening formed through the access tube 202 can be configured to receive an inner blade 204 that is used to radially move or retract nerve tissue or the like at or proximal to its distal end. More specifically, as illustrated, the inner blade 204 can include a proximal end 204p and a distal end 204d. As shown in FIG. 3A, the inner blade 204 can include the following portions, which are listed in their order from the proximal end 204p to the distal end 204d: a first cylindrical portion 204-1, a second cylindrical portion 204-2 connected to the first cylindrical portion 204-1, a first blade portion 204-3 and second blade portion 204-4 connected to the first blade portion 204-3. It should be understood that, although they are independently described, the portions 204-1 to 204-4 can be sections of a single, cohesive or monolithic inner blade 204.

The first cylindrical portion 204-1 can extend distally from the proximal end 204p of the inner blade 204, and the second cylindrical portion 204-2 can extend distally from the first cylindrical portion 204-1. The first and second cylindrical portions 204-1 and 204-2 can have a shape matching or similar to that of the access tube 202. That is, the degree of curvature of the first and/or second cylindrical portions 204-1 and 204-2 can be the same or substantially similar to that of the access tube 202. In some embodiments, the first and second cylindrical portions 204-1 and 204-2 can be coaxial with one another. The first cylindrical portion 204-1 can have a diameter and/or circumference formed by its outer surface that is larger than the diameter and/or circumference formed by the outer surface of the second cylindrical portion 204-2. The diameter and/or circumference formed by the outer surface of the second cylindrical portion 204-2 can be the same or substantially similar to the diameter and/or circumference formed by inner surfaces (e.g., openings) of the upper and/or lower portions 202-1 and 202-2 of the surgical access device 202, such that when the second cylindrical portion 204-2 is inserted therein, the outer surface of the second cylindrical portion 204-2 makes continuous contact (or is placed substantially closely in contact) with the inner surface of the upper and/or lower portions 202-1 and 202-2.

Because of the differences in diameter and/or circumference formed by the outer surfaces of the first and second cylindrical portions 204-1 and 204-2, a lip can be formed at an area where the first cylindrical portion 204-1 meets the second cylindrical portion 204-2. The lip can be configured to prevent distal movement of the inner blade 204 therebeyond, such that the second cylindrical portion 204-2 can be inserted and slid within the opening of the surgical access device while the first cylindrical portion 204-1 is prevented from such insertion within the opening of the access tube 202. In other words, the lip can engage with the distal end of the access tube 202 and prevent distal movement of the inner blade 204 relative to the access tube 202. The lip can be formed such that it is perpendicular with the outer surface of the inner blade 204 (e.g., forming a 90 degree angle) or angled a sufficiently small degree (e.g., more than 90 degrees and less than 180 degrees) such that the lip can indeed prevent insertion of the first cylindrical portion 204-1 within the opening of the access tube 202.

The proximal end of the first blade portion 204-3 can be formed on or attached to the distal end of the second cylindrical portion 204-2. The first blade portion 204-3 can extend longitudinally toward the distal end of the inner blade 204. The surface of the first blade portion 204-3 can be curved or arc-shaped, and can have a degree of curvature matching or substantially similar to that of the second cylindrical portion 204-2 and/or the upper portion 202-1 of the access tube 202. The length of the curve of the first blade portion 204-3, e.g., the width of the first blade portion, can vary and can be determined based on various factors including the size of the nerve tissue or other obstacle to be moved. The first blade portion 204-3 can have a surface that forms a partial circle or cylinder, similar to the cylindrical portions 204-1 and 204-2.

The length of the first blade portion 204-3 can vary and can be determined based on various factors, including the intended use, target area to be inserted, target nerve tissue or obstacle to be moved, and so forth. The length of the first blade portion 204-3 can be selected such that, when the inner blade 204 is fully inserted into the opening of the access tube 202, the distal end of the first blade portion reaches or approximates the distal end of the lower portion 202-2, and/or protrudes therefrom. When the first blade portion 204-3 is slid or disposed within the upper portion 202-1 of the access tube 202, the outside surface of the first blade portion 204-3 is in contact with or substantially proximate to the inside surface of the upper portion 202-1.

The proximal end of the second blade portion 204-4 can be formed on or attached to the distal end of the first blade portion 204-3. The second blade portion 204-4 can be curved or can have an arc-shape with a degree of curvature matching, based on, or substantially similar to that of the second cylindrical portion 204-2, the lower portion 202-2, and/or the first blade portion 204-3. The thickness of the body of the second blade portion 204-4, as measured by the material between the inner and outer surfaces thereof, can be larger than the thickness of the first blade portion 204-3. The length of the second blade portion 204-4 can be based on various factors described above. The length of the second blade portion 204-4 can be sufficiently long to protrude from the distal end of the access tube 202 and/or reach nerve tissue or other obstacles to be retracted or moved.

The second blade portion 204-4 can extend longitudinally at an angle different than that of the first blade portion 204-3. That is, as described above, the first blade portion 204-3 can extend parallel to the longitudinal direction of the inner surface of the upper portion 202-1 of the access tube 202, such that the outer surface of the first blade portion 204-3 is in contact with or is substantially proximate to the inner surface of the upper portion 202-1. The area where the first blade portion 204-3 meets the second blade portion 204-4 can form an oblique angle.

The blade 204 or a portion thereof can be or can include a spring arm. For instance, the blade 204 or a portion thereof can be formed from a flexible and resilient material such that the first and second blade portions 204-3 and 204-4 are biased to a default, resting position. The resting position can be one in which the second blade portion 204-4 is disposed in a radially outward position. As described in further detail below, operating or engaging with the inner blade 204 when disposed within the opening of the surgical access tube 202 can cause the inner surface of the upper and/or lower portions 202-1 and 202-2 to apply force (e.g., a radially inward force) against the bias of the blade 204 to cause the first blade portion and/or the second blade portion 204-3 and 204-4 to move radially inward. When this force is removed or reduced, the first blade portion 204-3 and/or the second blade portion 204-4 can return towards their resting, radially-outward position.

Use of the surgical access device 200 to move nerve tissue and/or other obstacles during surgery is now described in further detail. To use the surgical access device 200, the inner blade 204 can be inserted into the access tube 202, through the opening formed through the upper and lower portions 202-1 and 202-2. It should be understood that the inner blade 204 can be inserted prior to the upper and lower portions 202-1 and 202-2 being inserted into a patient's body and positioned at the target area, or can later be inserted once the upper and lower portions 202-1 and 202-2 have been properly arranged at the target surgical area.

Figure 3B:
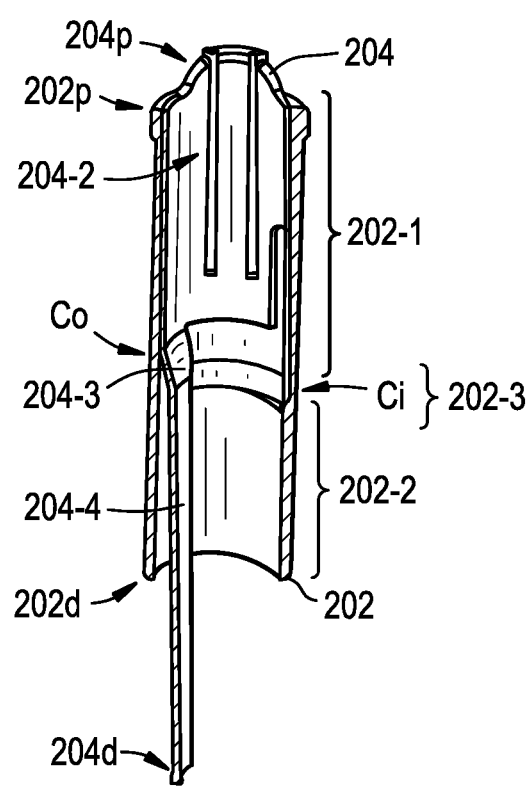
FIG. 3B is a cross-sectional view of an exemplary embodiment of an inner blade and an access tube of the access device of FIG. 2A.
Figure 3C:
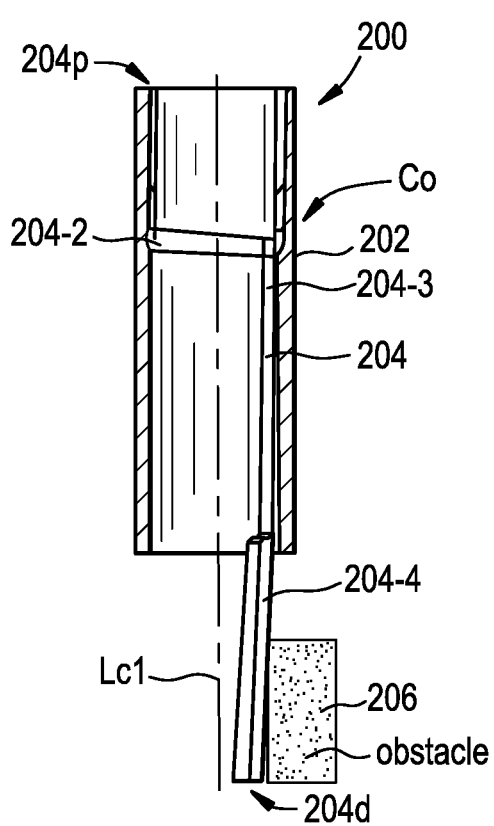
FIG. 3C is a sectional side view of the access device of FIG. 2A with an inner blade thereof in a radially inward position.

The inner blade 204 can be inserted through the opening of the upper and lower portions 202-1 and 202-2 such that the first and second blade portions 204-3 and 204-4 are in a first position or configuration. In a first position or configuration, the inner blade 204 and/or its first and second blade portions 204-3 and 204-4 are aligned with, or disposed on or along or in contact with the outer curve $C_o$ of the elbow 202-3 of the access tube 202, as shown in FIG. 3C. In this first position, the inner surfaces of the upper and/or lower portions 202-1 and 202-2 (and/or the elbow 202-3) apply a radially inward force against the outer surfaces of the first and/or second blade portions 204-3 and 204-4, such that the distal end of the second blade portion 204-4 is caused to flex or move radially inward, toward the central longitudinal axis $L_{C1}$ of the lower portion 202-2. The radially inward force applied against the outer surfaces of the first and/or second blade portions when in the first position can be due to the angling of the inner surface of the first and second portions 202-1 and 202-2 described above. The radially inward disposition of the distal end of the second blade portion 204-4 can enable the access tube 202 and/or its inner blade 204 to be more safely moved distally toward a target surgical area where a nerve tissue or other obstacle 206 is positioned, e.g., during initial positioning of the access device. The access tube 202 and/or the inner blade 204 can be positioned such that, in the first position of the inner blade, the nerve tissue 206 or other obstacle is disposed radially outward from the outer surface of the second blade portion 204-4.

Figure 3D:
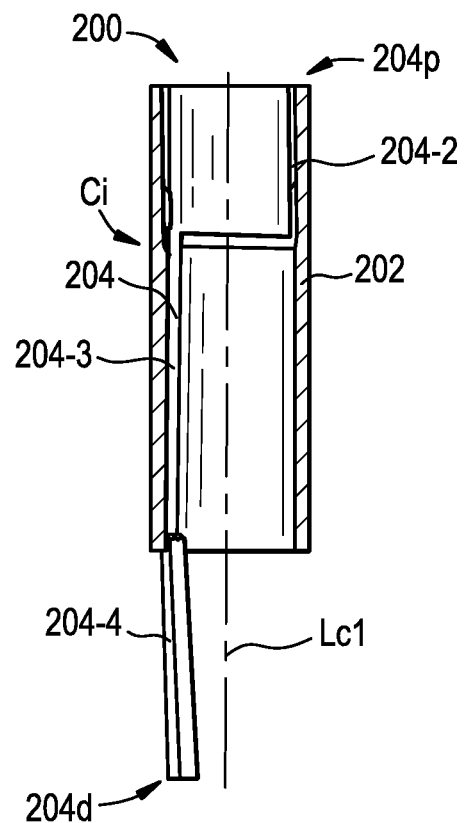
FIG. 3D is a sectional side view of the access device of FIG. 2A with an inner blade thereof in a radially outward position.

Once the distal end of the blade 204 is longitudinally aligned with the nerve tissue 206 or other obstacle, the access device 200 can be actuated in order to retract (e.g., move radially outward) the nerve tissue 206, as shown in FIG. 3D. To do so, the inner blade 204 can be rotated relative to the access tube 202, e.g., about the axis $L_{C2}$, to a second position. Such rotation can cause the inner blade and/or its first and second blade portions 204-3 and 204-4 to be aligned with, or disposed on or along or in contact with the inner curve $C_i$ of the elbow 202-3 of the access tube 202. The access tube 202 and/or the inner blade 204 can be configured such that they can be rotated clockwise and/or counterclockwise with respect to one another.

When aligned with the inner curve $C_i$, the blade 204 can be allowed to return towards its resting state, thereby moving the distal end of the blade and, by extension, a nerve or other obstacle in contact with an outer surface thereof, in a radially outward direction. The angling of the upper and lower portions 202-1 and 202-2, the shape of the elbow 202-3, and/or the angling of the portions of the inner blade 204, can be configured to cause the force from the inner surface of the upper and lower portions 202-1 and 202-2, and/or of the elbow 202-3, to be reduced or eliminated when the inner blade 204 is in the second position or configuration, such that the first and second blade portions 204-3 and 204-4 return to their biased positions and away from the central longitudinal axis $L_{C1}$, as shown in FIG. 3D. In their biased positions, the first and/or second blade portions 204-3 and 204-4 move radially outward, such that the nerve tissue 206 positioned adjacent to the second blade portion 204-4 is retracted in a radially outward direction, thereby positioning the nerve tissue in a safer location, shielded by the second blade portion 204-4 and/or away from the central longitudinal axis $L_{C2}$ of the lower portion 202-2. As can be seen in FIG. 3D relative to FIG. 3C, the distal end of the second blade portion 204-4 can be positioned at a further distance from the central longitudinal axis $L_{C1}$ when the blade is rotated to the second position.

The access device can include locking features for selectively maintaining the blade 204 in the first configuration, the second configuration, or any of a variety of intermediate configurations. For example, as shown in FIG. 3B, the proximal end of the blade 204 can include a cantilevered spring arm configured to flex or bend radially inward or outward relative to the main portion of the blade. The spring arm can be biased radially outward. The spring arm can be selectively positioned within a slot or groove formed in the access tube 202 to lock rotation of the blade 204 relative to the access tube. The access tube 202 can include slots aligned with the inner and outer curves of the elbow. Accordingly, when the blade is positioned in the first configuration, the spring arm can click into a groove of the access tube 202 to prevent rotation of the blade relative to the access tube and thereby maintain the blade in the first configuration. When the blade is positioned in the second configuration, the spring arm can click into another groove of the access tube 202 to prevent rotation of the blade relative to the access tube and thereby maintain the blade in the second configuration. When it is desired to change the configuration of the access device, the user can bend the spring arm radially inward to disengage the spring arm from the groove, thereby restoring free rotational movement of the blade relative to the access tube. The spring arm can be formed from a resilient material. The spring arm can include an actuator button to facilitate radial movement of the spring arm by the user.

Rotating the inner blade 204 relative to the access tube 202 can be done in various ways. For example, the first cylindrical portion 204-1 can be rotated relative to the upper portion 202-1, and/or vice versa.

Figure 3E:
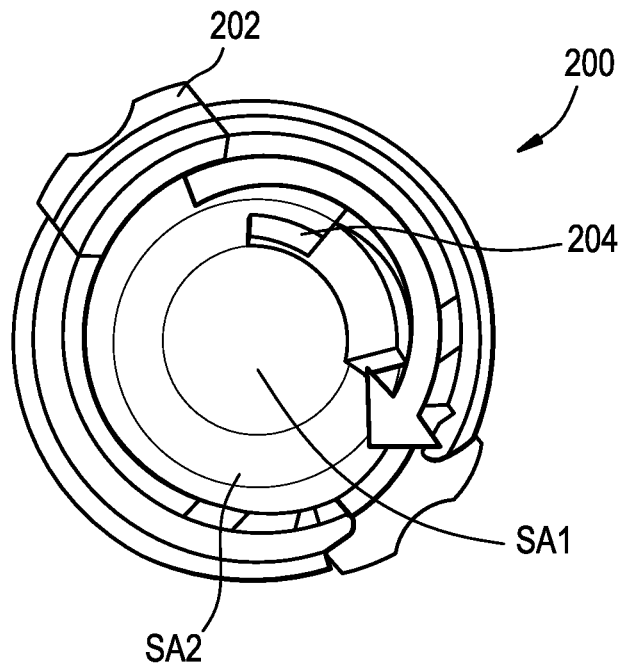
FIG. 3E is a top view of an exemplary embodiment of an access device in a radially inward configuration.

FIGS. 3E to 3H illustrate the rotation of the inner blade 204 to increase the size of the "safe area" in which to operate. The safe area refers to an area that is free or optimally clear of nerve tissue or other obstacles. In some embodiments, the safe area is a circular region extending radially inward from the inner surface of the distal end of the second blade portion 204-3. When the access tube 202 and the inner blade 204 are inserted into a target surgical region in a patient, and the inner blade 204 is positioned in a first configuration in which it is radially inwardly deflected due to its position on the elbow 204-3, as shown in FIG. 3E, a safe area SA1 is created by the distal end of the second blade portion 204-3.

Figure 3F:
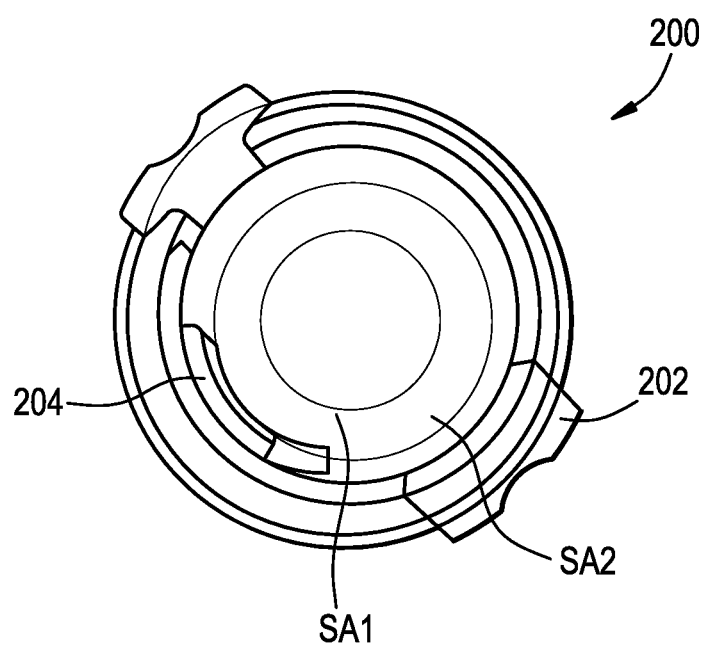
FIG. 3F is a top view of the access device of FIG. 3E in a radially outward configuration.

In turn, as shown in FIG. 3E, the inner blade 204 can be rotated relative to the access tube 202 such that it is moved to the other, outer curve of the elbow 202-3 of the access tube 202. That is, when the inner blade 204 is rotated into the second position or configuration, resilient material properties of the blade 204 can cause it to move radially outward, as shown in FIG. 3F. This can cause nerve tissue 206 or other obstacles in contact with the blade 204 to move radially outward, enlarging the safe area to be the size of safe area SA2. That is, the safe area SA2 can become a circular region having a larger diameter that the safe area SA1, and not having nerve tissue or other obstacles running therethrough. This larger safe area SA2 can enable access to a target surgical region in the patient with less risk of contacting or damaging the nerve tissue 206.

Figure 3G:
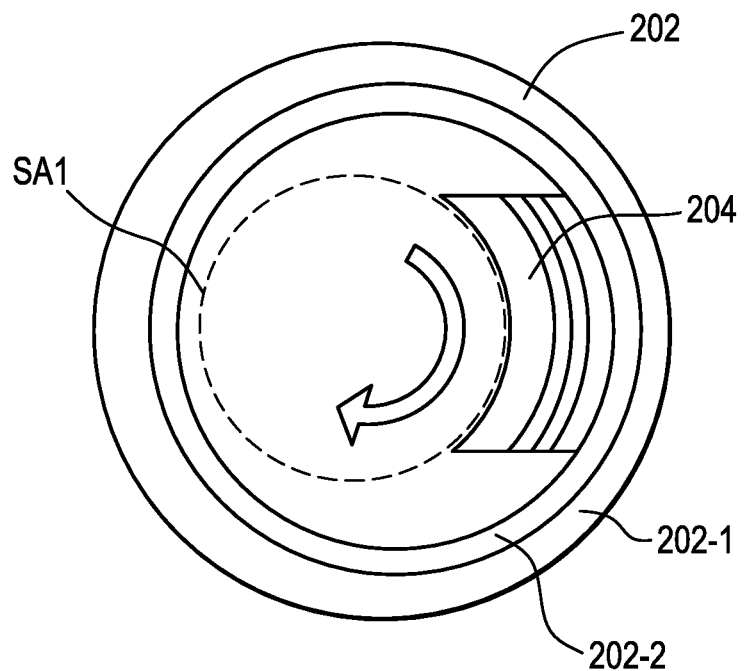
FIG. 3G is a top view of an exemplary embodiment of an access device in a radially inward configuration.
Figure 3H:
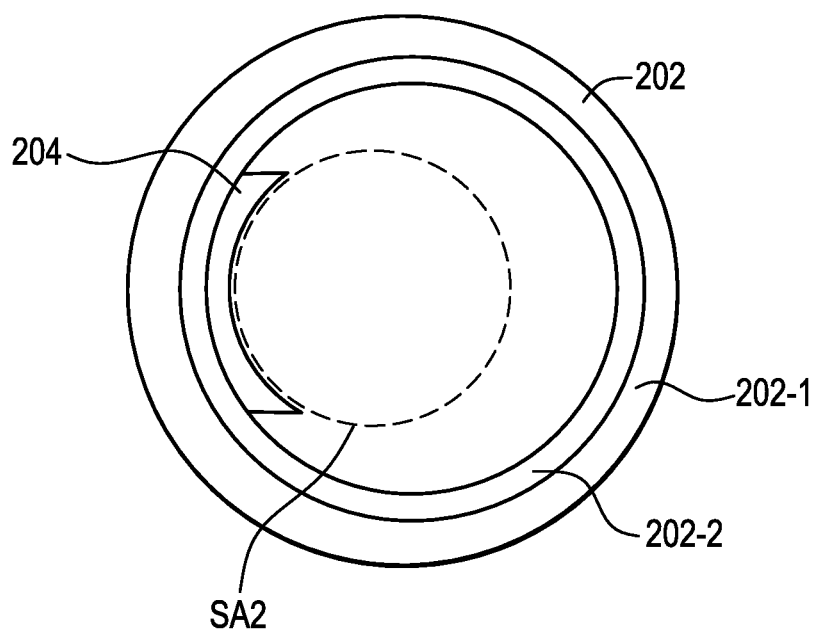
FIG. 3H is a top view of the access device of FIG. 3G in a radially outward configuration.

As shown in FIGS. 3G and 3H, the position and diameter of the safe areas SA1 and SA2 can be adjusted as needed during operation. That is, in some embodiments, the safe areas SA1 and/or SA2 are not concentric with the opening of the lower portion 202-2 of the access tube 202. When the inner blade 204 is in a first position (FIG. 3G), the force against the inner blade in a radially inward direction can cause the circular region defined by the distal end of the second blade portion 204-4 to be positioned non-coaxially with the opening of the second portion 202-2 of the access tube 202. Likewise, when the inner blade 204 is in a second position (FIG. 3H), the biasing of the inner blade 204 in a radially outward direction can cause the circular region defined by the distal end of the second blade portion 204-4 to be positioned further outward, in a non-coaxial manner relative to the opening of the second portion 202-2 of the access tube 202. Rotating both the access tube 202 and the inner blade 204 together can maintain the position or configuration of the inner blade 204 (e.g., first configuration, second configuration) relative to the elbow 202-3 of the access tube 202, while moving or rotating the safe area relative to the central axis $L_{C1}$ of the opening of the lower portion 202-2.

The diameter of the safe area can be adjusted based on the configuration of the access tube 202. That is, in some embodiments, the area comprising the body of the surgical access device between then inner and outer curves $C_i$ and $C_o$ of the elbow 202-3 can gradually change therebetween. Accordingly, the degree to which the blade is rotated relative to the access tube can control the degree to which the obstacle is retracted radially outward. For example, rotating the inner blade 204 to or from the inner and outer curves $C_i$ and $C_o$ (e.g., to and from a first position and a second position) can cause the first and second blade portions 204-3 and 204-4 of the inner blade 204 to gradually deflect radially inward or outward as described above. This gradual deflection can cause the safe area to gradually shrink and expand, or the obstacle to gradually be retracted or returned. Thus, the degree of retraction can be adjusted as needed by positioning the inner blade 204 at a position between the curves Ci and Co in which the nerve tissue 206 is sufficiently retracted. Such reduced retraction of the nerve tissue 206 can allow for the creation of a safe area sufficiently large to safely and effectively operate, while reducing the amount of movement and/or stretching of the nerve tissue 206 and thus the potential for it tearing, having reduced blood flow, or otherwise being negatively impacted.

Second Embodiment

FIGS. 4A to 4H illustrate another exemplary embodiment of a surgical access device 300. As shown, the surgical access device 300 can include an access tube 302 configured to receive an inner shield or blade 304 that can be used to radially move nerve tissue 306 and/or other obstacles. Although illustrated as a cylinder, the access tube 302 can have inner or outer surfaces that form a rectangle, triangle, oval, elliptical, or other transverse cross-sectional shape. The access tube can have a proximal end 302p and a distal end 302d. A hole or opening is formed therethrough, to and from the proximal end 302p and the distal end 302d, to define a working channel through the device 300. The hole or opening can be defined by the body of the access tube 302, which can have an outer surface 302o and an inner surface 302i.

The length of the access tube 302 and the diameter of its opening or working channel can vary. For instance, the length of the access tube 302 can depend on the depth of a target area to be operated on within a patient's body, as measured from a point of incision in the patient's skin. The diameter of the opening of the access tube 302 can depend on the types of instruments or other objects anticipated to move therethrough during the surgical procedure. The diameter of the opening of the access tube 302 can remain constant throughout the length of the access tube 302, from the distal end 302d to the proximal end 302p, or the access tube 302 can have different diameters at multiple points along its length (e.g., at the distal end 302d and the proximal end 302p.)

Figure 4C:
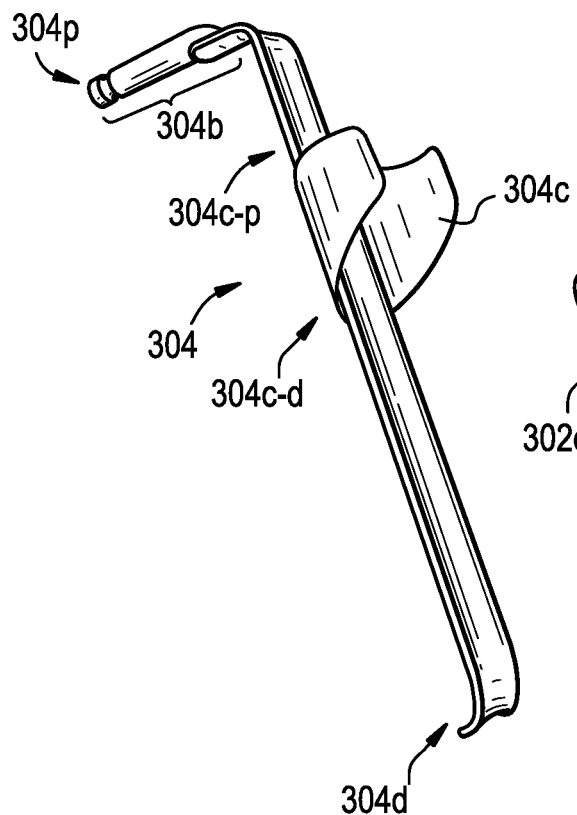
FIG. 4C is a perspective view of an exemplary embodiment of a shield of the access device of FIG. 4A.
Figure 4D:
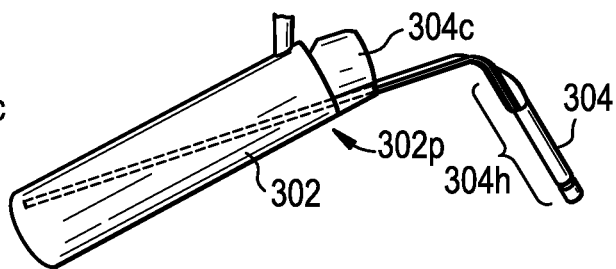
FIG. 4D is a sectional side view of another exemplary embodiment of an obstacle retracting access device in a radially inward configuration.
Figure 4E:
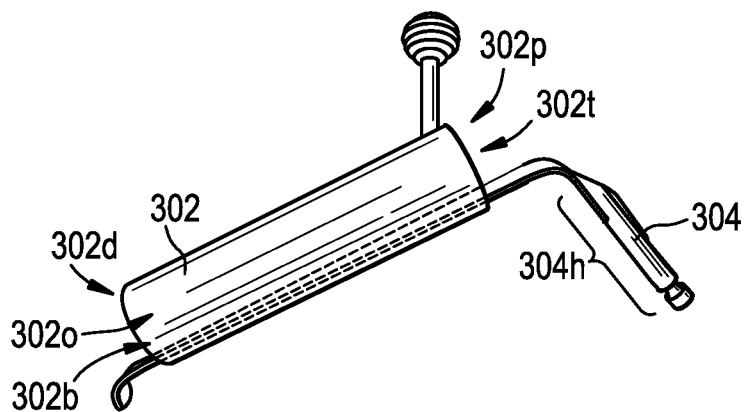
FIG. 4E is a sectional side view of the access device of FIG. 4D in a radially outward configuration.
Figure 4F:
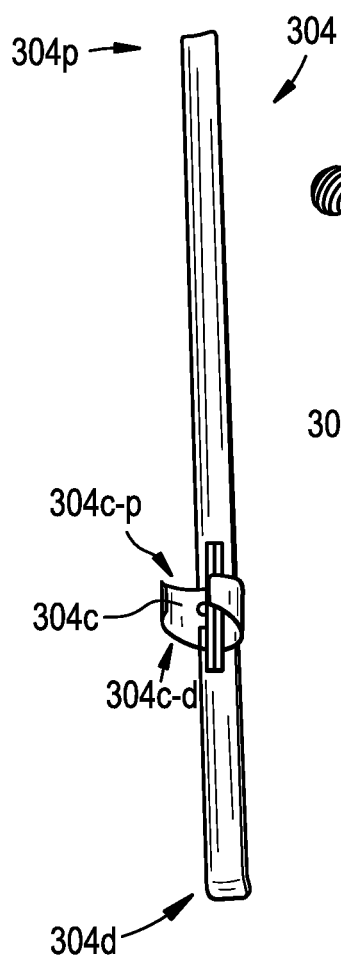
FIG. 4F is a perspective view of an exemplary embodiment of a shield.
Figure 4G:
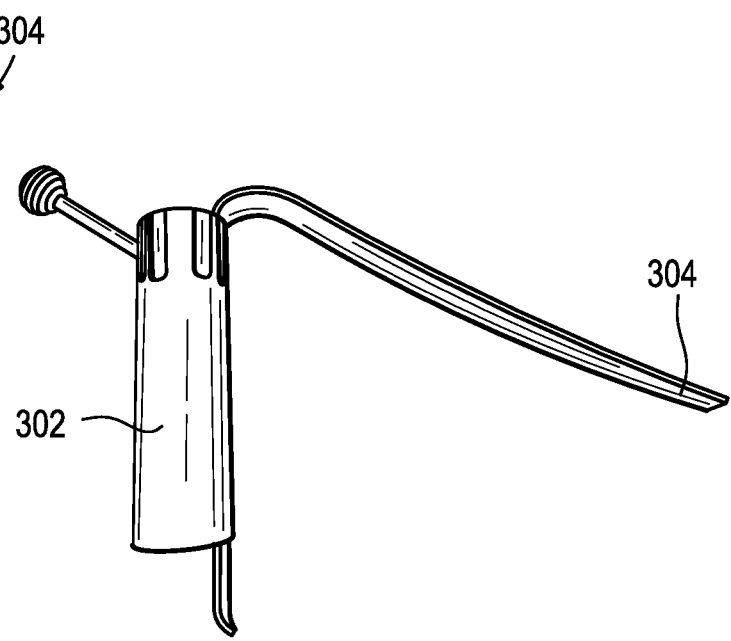
FIG. 4G is a side view of an exemplary embodiment of an obstacle retracting access device.
Figure 4H:
FIG. 4H is a top view of the access device of FIG. 4G.

As shown in FIGS. 4B and 4E, the access tube 302 can include a top surface 302t at the proximal end 302p, and a bottom surface 302b at the distal end 302d. The top surface 302t and the bottom surface 302b can be flat or angled. A flat surface means that the surface (e.g., top surface 302t) forms a 90 degree angle and/or is perpendicular to the walls of the body of the access tube 302. An angled surface means that the surface forms an angle other than a 90 degree angle with the rest of the walls of the body of the access tube 302. In some embodiments, the top surface 302t is flat, such that an angled cylindrical portion 304c (described in further detail below) of the blade 304 is more easily received by the opening of the access tube 302 at the proximal end 302p.

As illustrated in FIGS. 4A to 4H, the blade or shield 304 can be or can include a long blade or rod having a distal end 304d and a proximal end 304p. The blade 304 can include an angled cylindrical portion 304c, which as described below can be configured to cause movement of the distal end 304d of the blade 304 in radially inward and outward directions. Although the length of the blade 304 can vary based on various factors including the length of the access tube 302 and the intended use of the blade (e.g., depth of the nerve tissue 306 or other obstacle to be moved), the blade 304 can be at least longer than the access tube 304, in order to allow the blade 304 to protrude above the top surface 302t of the access tube 302 and/or below the bottom surface 302b. The blade 304 can be long enough such that the distal end 304d or a portion proximate to the distal end 304d can reach the nerve tissue 306 or other obstacle to be moved.

The width of the blade 304 can vary as needed and deemed optimal for various operations. Moreover, the shape of the body of the blade 304 can be curved or non-curved, as shown at least in FIGS. 4C and 4F. For instance, in a configuration in which the blade 304 has a curved body, the curvature of the blade 304 can match or substantially resemble the curvature of the access tube 302, such that when the blade 304 is in a position in which it is placed adjacent to or in contact with the inner surface 302i of the access tube 302, the entire outer surface of the blade or a substantial part thereof (e.g., 40%, 50%, 60%, 70%, 80%, 90%) makes contact with the inner surface 302i of the access tube 302. The shape and width of the blade can vary along its length. In some embodiments, a region adjacent to the distal end 304d of the blade 304 can be wider than the rest of the blade, for instance, to create a larger safe area in which to operate and/or to increase the amount of contact between the blade 304 and the nerve tissue 306 or other obstacle to be moved. In some embodiments, a region adjacent to the distal end 304d of the blade 304 can be curved while the rest of the blade can be non-curved. The curved portion of the blade 304 can minimize the contact of its edges with the nerve tissue 306 or other obstacle, thereby preventing severing or otherwise damaging the nerve tissue 306 or other obstacle.

The blade 304 can include a handle portion 304h that extends from the cylindrical portion 304c to the proximal end 304p. The handle portion 304h can have the same or a different shape (e.g., curvature) or width than the rest of the blade. For instance, the shape of the handle portion 304h can be configured to provide easier gripping. Likewise, the length of the handle portion 304h can vary as needed for various surgeries. The length of the handle portion 304h can be at least long enough that when the blade 304 is inserted and moved distally into the access tube 302 into a position in which the distal end 304h is at its most radially outward disposition, the handle portion 304h still protrudes above the top surface 302t of the access tube 302 such that it can be maneuvered by its operator.

Attached to the blade 304 can be the cylindrical portion 304c having an opening formed therethrough, to and from a distal end 304c-d and a proximal end 304c-p. The cylindrical portion 304c can connect the handle portion 304h to the rest of the blade 304. The cylindrical portion 304c can be a slotted or partial cylinder, meaning that it does not necessarily have a connected body around its circumference. In other words, the cylindrical portion 304c can include a slot or gap extending from its proximal end 304c-p to its distal end 304c-d. The gap or slot can be angled in various ways. As explained in further detail below, the slot in the cylindrical portion 304c can allow the cylindrical portion 304c to radially expand and contract, enabling it to be inserted, move and change positions within the access tube 302, thereby causing radial movement of the distal end of the blade 304.

The cylindrical portion 304c can have various shapes and lengths, e.g., based on the shape and length of the access tube 302. The length of the cylindrical portion 304c can be less than the length of the access tube 302. The shape of the cylindrical portion 304c can be the same as that of the access tube 302. Likewise, the opening formed through the cylindrical portion 304c can have various shapes and sizes, as deemed optimal or necessary for various surgical procedures. The circumference of the cylindrical portion 304c in a default and/or uncompressed state (e.g., prior to being inserted into the access tube 302) can be smaller than or equal to the circumference of the opening of the access tube 302 at its proximal end 302p, such that the distal end 304c-d of the cylindrical portion 304c can be inserted therein.

As illustrated, the distal end 304c-d of the cylindrical portion 304c can be angled or slash cut, meaning that at least a part of the body of the cylindrical portion 304c does not form a 90 degree angle with the outer side surface of the cylindrical portion 304c at its distal end 304c-d. In some embodiments, the angling or slash cut configuration of the distal end 304c-d of the cylindrical portion 304c means that the length of the cylindrical portion 304c, as measured from its proximal end 304c-p, is greater at one side relative to the length at a diametrically opposed end. As explained below in further detail, the angling or slash cut of the cylindrical portion 304c can enable the blade 304 to be more easily guided into the opening at the proximal end 302p of the access tube 302 and can encourage movement of the distal end of the blade as the blade is inserted further into the access tube. In some embodiments, the length of the blade 304 measured from its distal end 304d to the distal end 304c-d of the cylindrical portion 304c is less than the length of the blade 304 measured from its proximal end 304p to the proximal end 304c-p of the cylindrical portion 304c.

The access tube 302, the blade 304, and/or any of its parts or components can be made of various materials. The cylindrical portion 304c and/or the blade 304 can be made of a resilient, flexible or malleable material that allows for compression thereof. For instance, the cylindrical portion 304c can be made of a material that provides spring-like qualities, such as allowing the cylindrical portion 304c to compress and decompress as force is applied thereto (e.g., by the inner surface 302i of the access tube 302) and/or as force is applied to the distal end 304d of the blade 304 (e.g., by the tension of the nerve 306 or other obstacle).

As shown in FIGS. 4C to 4H, the blade 304 can be formed of a malleable or flexible material that allows the blade 304 to be bent to a desired length—e.g., to provide optimal amount of protrusion of the distal end of the blade 304, and/or to optimally function with access tubes of various lengths. A portion of the blade 304 that is bent at its proximal end can be used as a handle of the blade, to control its rotation and/or distal and proximal movement. In some embodiments, the malleable or flexible characteristic of the blade 304 allows portions of the blade 304 that extend outside of the access tube 302 to be bent away from a working channel of the access tube 302, either at its proximal or distal ends. For instance, a portion of the blade 304 that protrudes from the proximal end 302p of the access tube 302 (e.g., when the blade 304 is inserted to the desired depth within the access tube 302 and moved to a radially-outward position) can be bent away from the working channel formed by the proximal end of the access tube 302, to provide clear access to the working channel and/or such that it forms a handle portion or the like. This can facilitate use of the blade 304 with any of a variety of access tubes having any of a variety of lengths, without extra length of the blade protruding upwards and interfering with the surgery.

Operation of the surgical access device 300 to move nerve tissue and/or other obstacles during surgery is now described in further detail. The access tube 302 and the blade 304 can be first engaged by inserting the distal end 304d of the blade 304 into the opening formed at the proximal end 302p of the access tube 302. The blade 304 can be distally moved along the opening of the access tube 302.

FIGS. 4A and 4D illustrate a first position in which the cylindrical portion 304c of the blade 304 begins to engage (e.g., move distally within the access tube 302) with the access tube 302. As can be seen, in the first position, the blade 304 can be disposed at an oblique angle with respect to a central longitudinal axis of the working channel of the access tube, such that it is not in contact with and/or parallel to the inner surface 302i of the access tube 302. In the first position, the distal end of the blade 304 can be aimed toward the center of the opening, such that the blade 304 is directed at or crosses the central longitudinal axis $L_c$ (shown in FIG. 4B) of the access tube 302 at a point along the length of the opening of the access tube 302, and such that the proximal end 304p and the distal end 304d are on opposite sides of the central longitudinal axis $L_c$. In the first position, the access tube 302 can be disposed such that the outer surface of the distal end 304d of the blade is positioned radially inward from and/or adjacent to the nerve tissue 306 (e.g., in a position opposite the direction in which the nerve tissue 306 is to be retracted). Moreover, in the first position, the walls forming the outside surface of the cylindrical portion 304c can be non-parallel to the opening or inner surface of the access tube 302. In the first position, the distal end of the 304d can cross beyond the central longitudinal axis $L_c$, toward or to the opposite (e.g., diametrically opposite) inner surface of the access tube 302. While in such cases the distal end of the 304d can be deemed to be disposed outwardly relative to the central longitudinal axis $L_c$, it should be understood that its configuration is nonetheless referred to herein as an "inward configuration" due to its inward disposition or movement relative to its outward configuration and/or the tissue or obstacle to be retracted.

Once the tip at the distal end of the blade 304 has been positioned in front of the nerve tissue 306, the cylindrical portion 304c can be advanced or slid distally within the opening of the access tube 302 (as illustrated by the dashed lines in FIG. 4A). As the blade 304 is moved further distally into the access tube 302, the cylindrical portion 304c can contract radially and/or the outer walls or surface of the cylindrical portion 304c can move parallel to or in contact with the inner walls or surface 302i of the access tube 302. As the cylindrical portion 304c moves, the blade 304 is also moved toward a parallel position with the inner walls 302i of the access tube 302. Resilient material properties of the cylindrical portion 304c can bias the blade towards the inner sidewall of the access tube 302 as the cylindrical portion is inserted distally into the access tube. In this second position of the blade 304, illustrated in FIGS. 4B and 4E, a portion of the blade 304 can be adjacent to and/or in contact with the inner walls 302i of the access tube 302. This can cause the distal end 304d of the blade 304 to radially retract the nerve tissue 306 or other obstacle. That is, the tip of the blade 304 at its distal end 304d can cross the central longitudinal axis $L_c$, such that, in the second position, the distal end 304d and the proximal end 304p of the blade 304 are on the same side of the central longitudinal axis $L_c$. In the second position, the distal end 304d is referred to herein as being disposed at or in an outward configuration.

As the blade 304 transitions from the first position illustrated in FIGS. 4A and 4D into the second position illustrated in FIGS. 4B and 4E, the nerve tissue 306 or other obstacle can be moved radially outward, creating a larger safe area in which to operate.

The spring force of the material used to form the inner blade and/or the cylindrical portion can be selected to tailor the amount of radial force applied to the nerve or other obstacle. This way, the blade can retract the nerve but if the nerve is resisting, the blade can give a little, allowing the nerve to push the blade inward against the spring force, helping to prevent too much force from being exerted on the nerve.

As noted above, the distal end of the spring cylinder can be angled or slash-cut, which can (1) provide a lead-in to ease insertion of the inner blade into the outer access tube, and (2) allow the inner blade to be inserted in the initially angled position without moving outward until the inner blade is pushed further into the outer tube.

It should be understood that the blade 304 can be rotated relative to the access tube 302 to any desired position that provides an optimal or desired safe area in which to operate.

Third Embodiment

FIGS. 5A to 5F illustrate another exemplary embodiment of a surgical access device 400 with flexible arms or blades. The surgical access device 400 can include an outer tube 402, a middle tube 404, and an inner tube 406. In use, the outer tube 402 can be inserted into a patient to define a working channel. The middle tube 404 can be inserted through the outer tube with one or more movable arms of the middle tube disposed in a radially-inward position. The arms can project distally beyond the distal end of the outer tube 402 to position outer surfaces of the arms adjacent to a nerve or other obstacle to be retracted. Finally, the inner tube 406 can be inserted through the middle tube 404 to push the one or more arms radially outward, thereby retracting the nerve or other obstacle. The middle and inner tubes 404, 406 can be less than full tubes, e.g., half tubes, quarter tubes, etc., such that the one or more arms extend around less than the entire circumference of the outer tube 402. Instruments, implants, and other objects can be inserted through the inner tube 406, past the retracted obstacle.

The outer tube 402 can be configured to receive the middle tube 404 and the middle tube 404 can be configured to receive the inner tube 406. It should be understood that although the outer, middle and inner tubes 402, 404 and 406 are illustrated as having circular transverse cross-sections, other shapes can be used.

The outer tube 402 can be a cylinder having a hole or opening formed therethrough, extending through a proximal end 402p and a distal end 402d. The hole or opening of the outer tube 402 can be defined by the body of the outer tube 402, which can have an outer surface and an inner surface facing the opening. The hole or opening of the outer tube 402, and/or the circumference of the outer tube 402 can be of any size deemed necessary or optimal for various surgical procedures. The opening of the outer tube 402 can have a diameter at least as large as the diameter formed by the outer surface of the middle tube 404, such that the middle tube 404 can be slid therein or therethrough. The outer tube 402 can have a diameter that is consistent throughout the length of the tube—e.g., that is the same at the distal end 402d as it is on the proximal end 402p—or can have a diameter that changes throughout the length of the tube. For instance, the outer tube 402 can gradually narrow from the proximal end 402p to the distal end 402d. The outer tube 402 can have any length that is deemed optimal or necessary for various surgical procedures, for instance, to reach a target surgical area. In some embodiments, the length of the outer tube 402 is less that is smaller than the length of the middle tube 404.

Figure 5A:
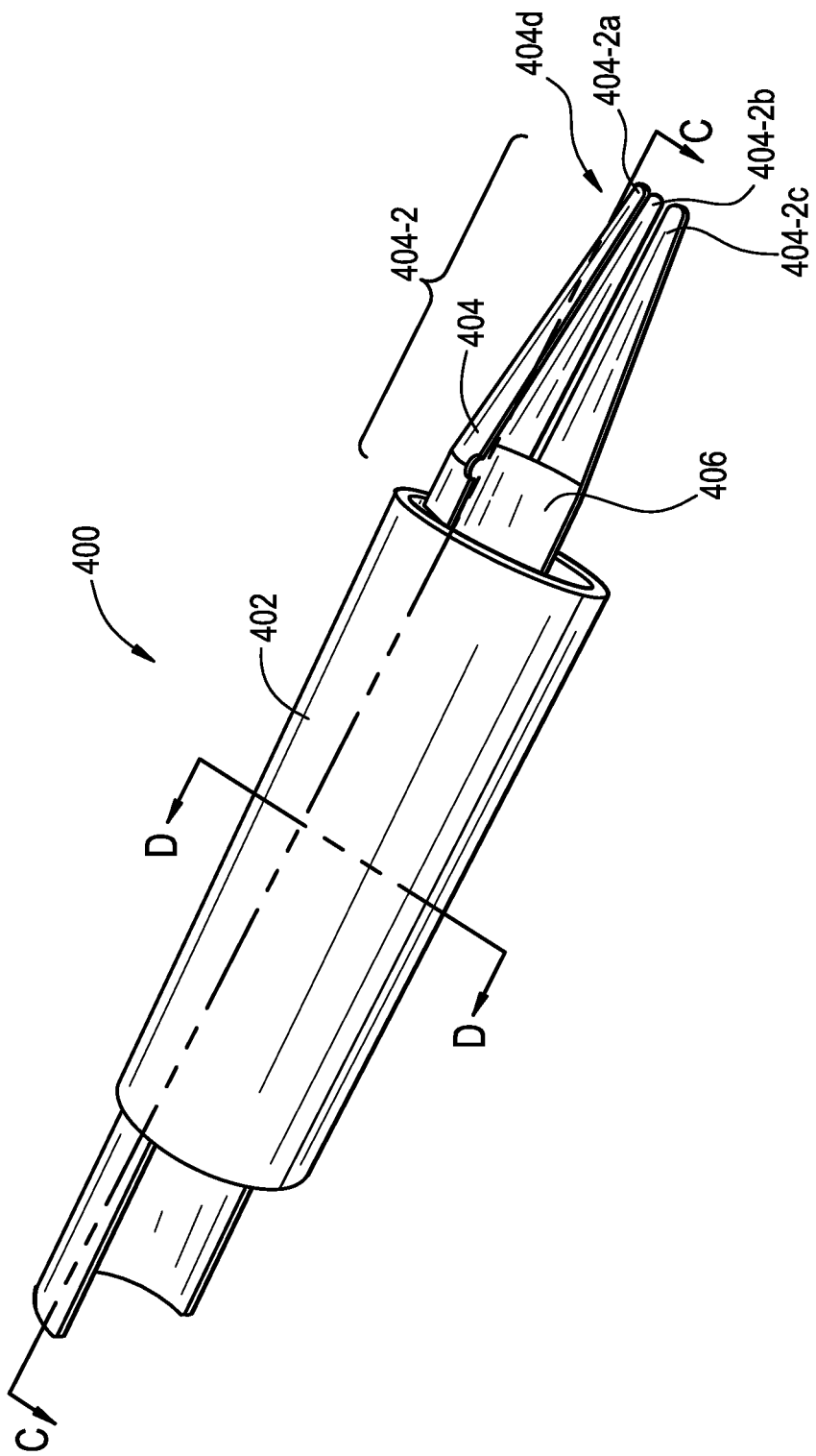
FIG. 5A is a perspective view of another exemplary embodiment of an obstacle retracting access device.
Figure 5B:
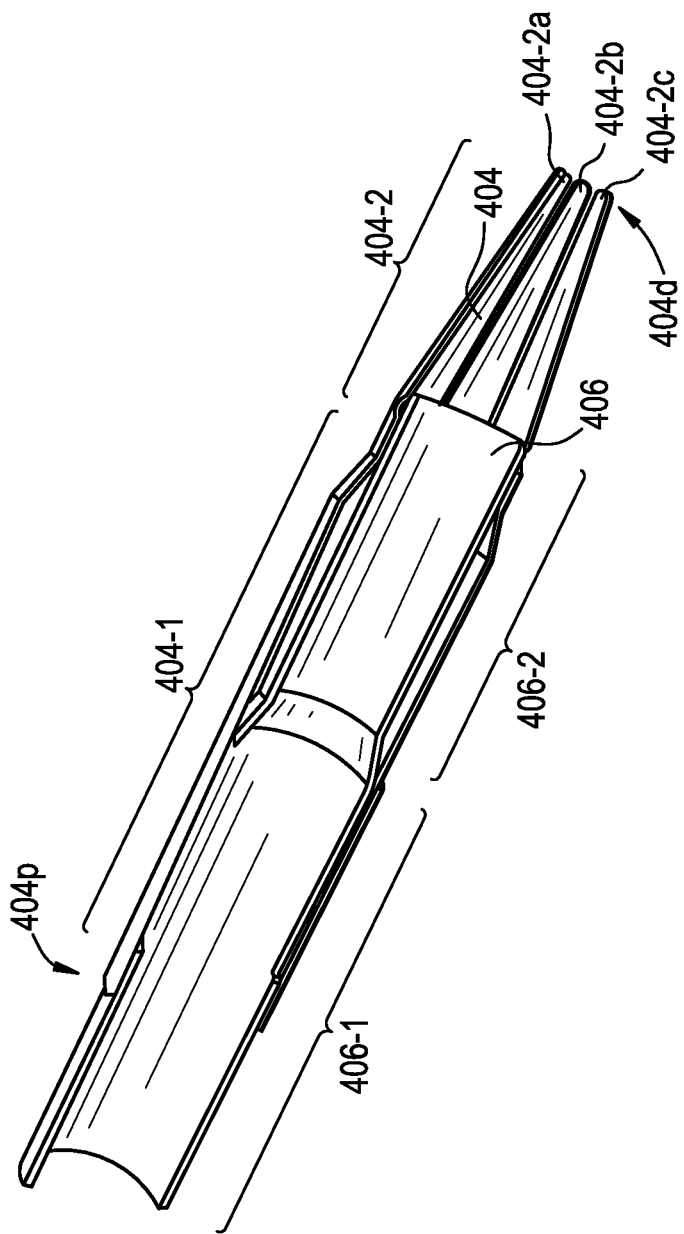
FIG. 5B is a sectional perspective view of the access device of FIG. 5A taken along the line C-C.
Figure 5C:
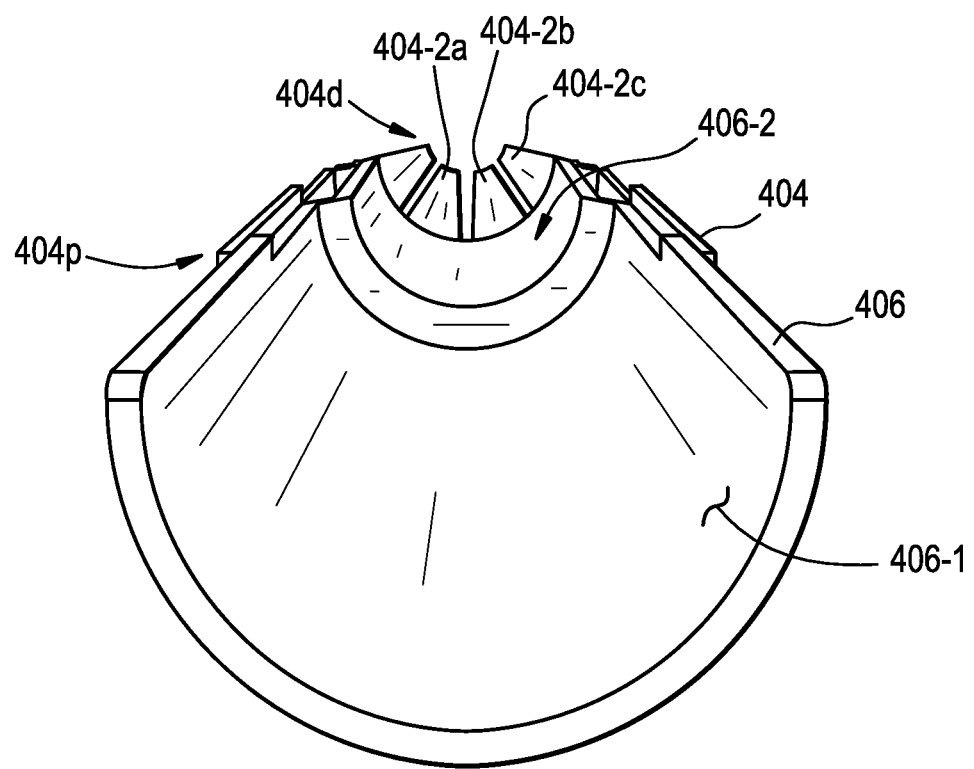
FIG. 5C is a sectional perspective view of the access device of FIG. 5A taken along the line D-D.
Figure 5D:
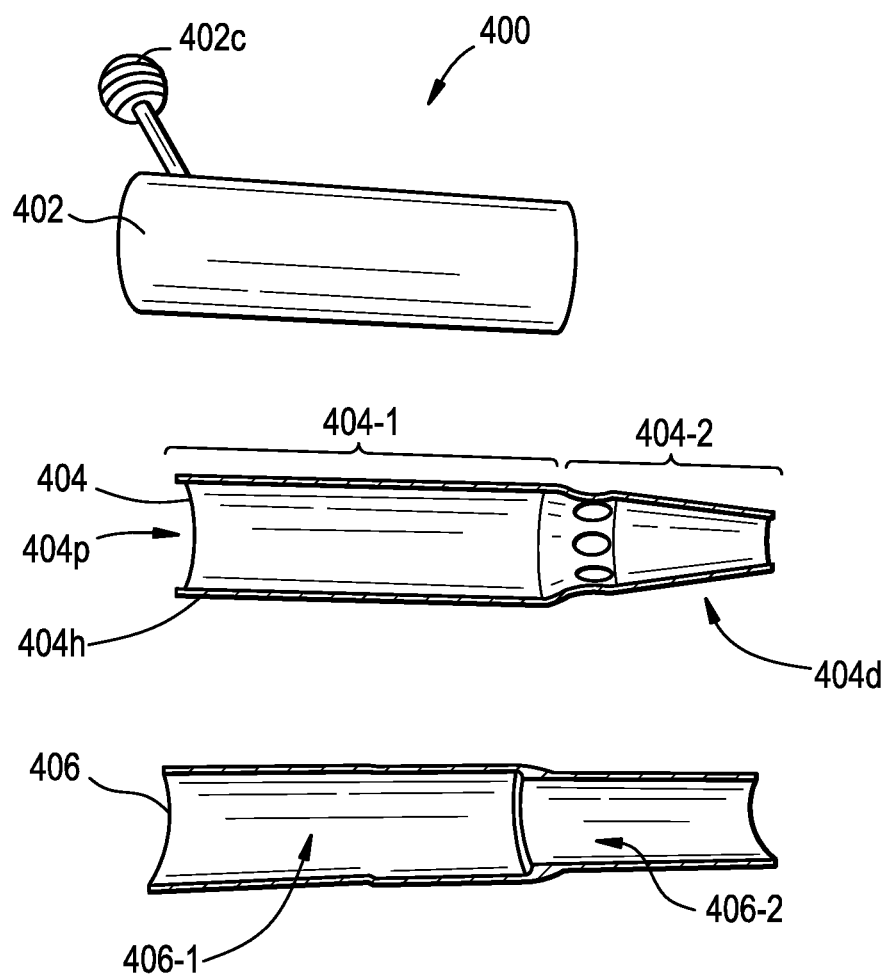
FIG. 5D is a side view of the access device of FIG. 5A, unassembled.

As shown in FIG. 5D, the outer tube 402 can include a connector or mating feature 402c, which can allow the surgical access device 400 and/or the outer tube 402 to be attached to another object, e.g., to support the access device 400 in a fixed position and/or orientation relative to a support. Exemplary supports include contralateral pedicle anchors, snake arm type connectors, surgical tables, and so forth. The connector 402c can be used as a handle, for example, to stabilize or manipulate the outer tube 402 and/or the surgical access device 400.

The middle tube 404 can be a cylinder having a hole or opening formed therethrough, extending through a proximal end 404p to a distal end 404d. The hole or opening of the middle tube 404 can be defined by the body of the middle tube 404, which can have an outer surface and an inner surface facing the opening. The shape, length and other features of the middle tube 404 can vary as deemed necessary or optimal for various surgeries and to function with the outer tube 402 and the inner tube 406. For instance, the diameter of the middle tube 404 can be slightly smaller than that of the outer tube 402, such that the middle tube 404 can slide or move within the opening of the outer tube 402. In some cases, their diameters can be substantially similar to provide some contact and/or friction therebetween. The middle tube 404 can be longer than the length of the outer tube 402, such that when the middle tube 402 is inserted fully into the outer tube 402, the distal end 404d of the middle tube 404 protrudes through the opening at the distal end of the outer tube 402.

Figures 5E, 5H:
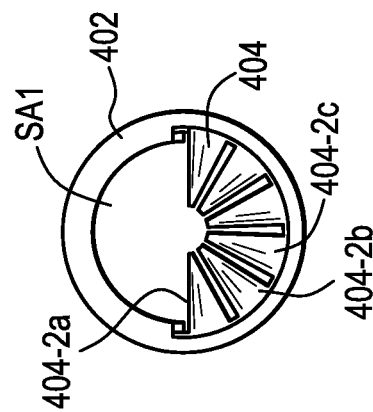
FIG. 5E is a side view of the distal end of the access device of FIG. 5D having an inserted middle tube in a radially inward configuration.
FIG. 5H is a side view of the distal end of the access device of FIG. 5D having inserted middle and inner tubes.
Figures 5F, 5I:
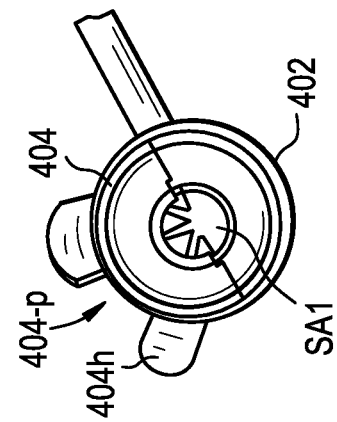
FIG. 5F is a top view of the access device of FIG. 5E.
FIG. 5I is a top view of the access device of FIG. 5H.

As shown in FIGS. 5D, 5F, and 5I, the middle tube 404 can have a handle 404h formed on its proximal end 404p. The handle 404h can be a tab or any other protrusion extending outwardly from the outer surface of the middle tube 404. The handle 404h can protrude from the middle tube 404 a distance at least sufficient to limit distal advancement of the middle tube 404 into the opening of the outer tube 402. That is, the handle 404h, which can be provided on the proximal end 404p, can engage the body of the outer tube 402 at its proximal end 402p when the middle tube 404 has been fully inserted into the outer tube 402. As explained in further detail below, the handle 404h can be used to move or rotate the middle tube 404 to a desired position, and/or to align the middle tube 404 with other tubes (e.g., inner tube 406).

As shown in FIGS. 5B and 5D, the middle tube 404 can include a first, constant or static portion 404-1 and a second, expandable or movable portion 404-2. The opening formed through the first, constant portion 404-1 can be consistent throughout its length. The expandable portion 404-2 can include one or more flexible arms, such as illustrated arms 404-2a, 404-2b, etc. that are connected to the constant portion 404-2 and separated by longitudinal slots therebetween. The expandable portion 404-2 can be referred to as a flower or flower-like design, in which the arms are analogous to the petals of the flower. The arms can have distal ends or tips that are curved, bent or angled in a radially inward direction to prevent or reduce the likelihood of severing tissue at the target region where the distal end of the surgical access device 400 is placed.

Each of the arms can extend from the distal end of the constant portion 404-1 towards the distal end of the expandable portion 404-2. The arms can be configured such that they are flexible and/or resilient to allow for biased radial deflection thereof. For instance, the arms can have a resting state in which they are angled obliquely relative to a central longitudinal axis of the middle tube, such that the arms angle radially-inward in a proximal-to-distal direction. In other words, the arms can be angled inwardly toward the central longitudinal axis of the distal end of the expandable portion 404-2. Insertion of the inner tube into the middle tube can push the arms away from their resting position, deflecting the arms radially outward away from the central longitudinal axis. The arms can thus have a closed configuration, such as that shown in FIGS. 5A, 5B, 5C, 5D, and 5E to 5G, in which the arms are angled inwardly toward the central longitudinal axis of the distal end of the expandable portion 404-2. At the distal end of the expandable portion 404-2, the distal end of the arms can contact one another or can be separated such that they form a smaller opening at the distal end 404d of the middle tube 404. The arms can also have an open configuration, such as that shown in FIGS. 5H to 5J, in which the distal end of each of the arms can be deflected radially outward, pivoting relative to a region at which the constant portion 404-1 meets the expandable portion 404-2 (e.g., where the arms begin to be formed or extend from). Deflecting the arms radially outward is described in further detail below.

The expandable portion 404-2 of the middle tube 404 can have any number of arms. The width and length of the arms can vary as needed or deemed optimal. The gap or slot separating the arms can be wider than the arms themselves. Wider arms can provide additional contact with the nerve tissue or other obstacle to be moved or retracted by the arms. The most proximal end of the slots separating the arms can include a circle or other shape different than and/or larger than that of the slots, to provide more efficient and effective expansion of the arms. As explained in further detail below, the expandable portion 404-2 of the middle tube 404 can be expanded by the insertion of the inner tube 406 into the opening formed through the middle tube 404.

The inner tube 406 can be a cylinder having a hole or opening formed therethrough, extending from a proximal end 406p to a distal end 406d. The hole or opening of the inner tube 406 can be defined by the body of the middle tube 406, which can have an outer surface and an inner surface facing the opening. The shape, length and other features of the inner tube 406 can vary as deemed necessary or optimal for various surgeries and to function with the outer tube 402 and the middle tube 404. For instance, the diameter of the inner tube 406 can be slightly smaller than that of the middle tube 404, such that the inner tube 406 can slide or move within the opening of the middle tube 404. Their diameters can be similar to each other such that contact and/or friction therebetween can be achieved. The inner tube 406 can be longer than the outer tube 402. The inner tube 406 can have a length that is equal to or substantially the same as the length of the middle tube 404. Such a configuration of the lengths of the inner tube 406 and the middle tube 404 can allow the inner tube 406 to engage with and/or be in contact with all or a substantial portion of the inner surface of the middle tube 404 when the inner tube 406 is inserted fully through the middle tube 404.

As shown in FIG. 5I, the inner tube 406 can have a handle 406h formed on its proximal end 406p. The handle 406h can be a tab or any other protrusion extending outwardly from the outer surface of the inner tube 406. The handle 406h can protrude from the inner tube 406 a distance at least sufficient to prevent the further distal advancement of the inner tube 406 into the opening of the middle tube 404. That is, the handle 406h, which can be provided on the proximal end 406p, can engage with the body of the middle tube 404 and/or the outer tube 402 at its proximal end 406p when the inner tube 406 has been fully inserted into the middle tube 404. Moreover, as explained in further detail below, the handle 406h can be used to move or rotate the inner tube 406 to a desired position, and/or to align the inner tube 406 with other tubes (e.g., middle tube 404).

The inner tube 406 can include a first, proximal portion 406-1 and a second, distal or expander portion 406-2. The proximal portion 406-1 can be a cylinder that has a constant (or substantially constant) diameter throughout its length and a continuous (e.g., non-gapped) body. The expander portion 406-2 can be a cylinder that has a constant (or substantially constant) diameter throughout its length and a continuous (non-gapped) body. The expander portion can have a diameter that tapers or narrows longitudinally in a distal direction. The expander portion 406-2 can have a smaller diameter than the constant portion 406-2, but larger than at least the distal end (e.g., tip) of the expandable portion 404-2 of the middle tube 404. This configuration can allow the outer surface of the expander portion 406-2 to cause the arms of the expandable portion 404-2 to deflect in a radially outward direction due to the force or pressure applied to their inner surfaces.

The middle tube 404 and/or the inner tube 406 can be partial or slotted cylinders, meaning that the body defining the tubes 404 and 406 can be less than full circles or cylinders. For instance, as shown in FIG. 5A, the middle tube 404 and the inner tube 406 can have bodies or walls that form a half cylinder, though they can be any other partial percentage of a cylinder (e.g., 40%, 60%, 70%). Often in surgical procedures, nerve tissue or other obstacles do not have to be retracted in all directions along the full circumference of a circle as would be achieved by fully-closed cylinder embodiments of the middle tube 404 and inner tube 406. Thus, a partial cylinder can allow for directional retraction of tissue or other obstacles, e.g., such that an obstacle can be retracted without moving or retracting other surrounding tissue. Manufacturing of partial cylinder tubes 404 and 406 can reduce material and costs.

Figures 5G, 5J:
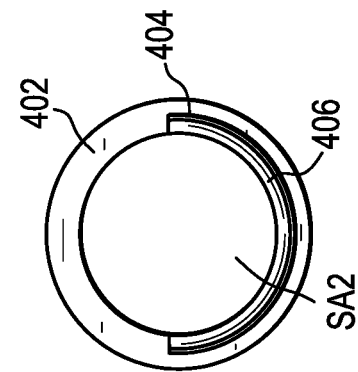
FIG. 5G is a diagram illustrating the top view of the access device of FIG. 5F.
FIG. 5J is a diagram illustrating the top view of the access device of FIG. 5I.

The handles 404h and 406h can be manufactured at the same position along the circumference of the tubes at their proximal ends 404p and 406p, such that aligning the handles 404h and 406h one above the other causes the rest of the tubes 404 and 406 to be aligned. This can be particularly advantageous in embodiments in which the middle tube 404 and the inner tube 406 are partial cylinders. The handles can include slots and protrusions or other mechanisms to lock their positions relative to one another and/or relative to the outer tube 402, e.g., to prevent their rotation during a surgical procedure. For instance, as shown in FIGS. 5G and 5J, the opening of the outer tube 402 can have a diameter that is larger along part of its circumference that is equal to the circumference of the partial cylinder of the middle tube 404 and the inner tube 406. In other words, a part of the inner surface of the outer tube 402 can form a longitudinal slot in which the middle tube 404 can be inserted. The area of the inner surface of the outer tube 402 at which the size of the opening changes can form inwardly protruding walls that prevent the rotation of the middle tube 404 relative to the outer tube 402.

In embodiments in which the middle tube 404 and/or the inner tube 406 are partial cylinders, the distal end 404d of the middle tube 404 can be positioned, prior to retraction of the nerve tissue or other obstacle, such that the outer surfaces of the arms of the middle tube 404 are adjacent to (e.g., radially inward from and rotationally aligned with) the nerve tissue to be moved. This way, the radially outward movement of the arms can cause the tissue to be outwardly retracted.

Operation of the surgical access device 400 (including partial cylinder middle and inner tubes 404 and 406) to retract nerve tissue or other obstacles during surgery is now described in further detail. Initially, the outer tube 402 can be inserted via an incision in the patient's body toward a target area of interest. The distal end 404d of the middle tube 404 can be inserted through the opening formed at the proximal end 402p of the outer tube 402. As shown in FIG. 5E, the middle tube 404 can be advanced distally toward the target area, to a depth at least as deep or deeper than the nerve tissue or other obstacle to be retracted. As shown in FIG. 5E, the distal advancement of the middle tube 404 can cause the arms to protrude through the opening at the distal end of the outer tube 402. In some embodiments, further distal movement of the middle tube 404 relative to the outer tube 402 can be prevented by the engagement of the handle 404h with the proximal end of the outer tube 402. Thus, the middle tube 404 can be designed and/or manufactured to have a length at least sufficient to reach the nerve tissue or other obstacle to be retracted. The outer tube 402 and the middle tube 404 can be assembled outside of the patient's body and inserted into the patient's body when they are already assembled, or can be assembled in situ.

As shown in FIGS. 5G and 5J, the middle tube 404 (and the inner tube 406) can be slid into the opening of the outer tube 402 along a slot formed in the inner surface of the outer tube 402. The slot formed in the inner surface of the outer tube 402 can have the same width (e.g., circumference) as that of the middle tube 404. Such a configuration can prevent the rotation of the middle tube 404 relative to the outer tube 402. In such embodiments, the outer tube 402 (and thus the middle tube 404 inserted therein) can be rotated in order to align the middle tube 404 at an optimal position relative to the nerve tissue or other obstacle to be retracted. That is, the outer tube 402 can be rotated until the outer surfaces of the arms of the expandable portion 404-2 of the middle tube 404 are adjacent to the nerve tissue or other obstacle to be retracted. As shown in FIGS. 5F and 5G, a safe area SA1 for operation can be created at the region in radially inward from the arms of the middle tube 404.

In some embodiments, the outer tube 402 does not have a longitudinal slot along its inner surface in which to insert the middle tube 404, thereby allowing rotation of the middle tube 404 relative to the outer tube 402. In such embodiments, the middle tube 404 can be rotated or otherwise manipulated (e.g., pulled proximally, pushed distally) using, for example, the handle 404h, until the outer surfaces of the arms of the expandable portion 404-2 of the middle tube 404 are adjacent to the nerve tissue or other obstacle to be retracted.

The distal end 406d of the inner tube 406 can be inserted into the opening formed at the proximal end 404p of the middle tube 404. As described above in connection with the middle tube 404, and as can be seen in FIG. 5J, the inner tube 406 can be inserted along a longitudinal slot formed by the inner surface of the outer tube 402. As shown, in such embodiments, the middle tube 404 and the inner tube 406 can be circumferentially aligned without their rotation relative to each other needing to be adjusted. On the other hand, in embodiments in which a longitudinal slot is not formed by the inner surface of the outer tube 402, prior to distally advancing the distal end 406d of the inner tube 406 into the expandable portion 404-2 of the middle tube 404, the inner tube 406 can be rotated into alignment with the middle tube 404. This can be achieved, for instance, by aligning the handles 404h and 406h of the middle and inner tubes 404 and 406. This can ensure that the expander portion 406-2 can contact and expand all of the arms of the middle tube 404 upon insertion. FIGS. 5E, 5F, and 5G illustrate aligned middle and inner tubes 404 and 406.

The inner tube 406 can be advanced distally through the opening of the middle tube 404, as shown in FIG. 5H, causing the distal end 406d of the inner tube 406 to protrude through the opening at the distal end of the outer tube 402. The larger diameter of the expander portion of the inner tube 406-2 can cause the arms of the expandable portion 404-2 to deflect outwardly as the distal end of the inner tube 406 slides therethrough, thereby retracting a nerve or other obstacle. The degree to which the obstacle is retracted can be controlled by the degree to which the inner tube is advanced distally relative to the middle tube. The outer surface of the expander portion 406-2 can apply a radially outward force on the arms of the expandable portion 404-2, causing their outward movement. As a result, the nerve tissue or other object positioned radially outward of the arms can be caused to retract or move outwardly as the arms are deflected.

Figure 6A:
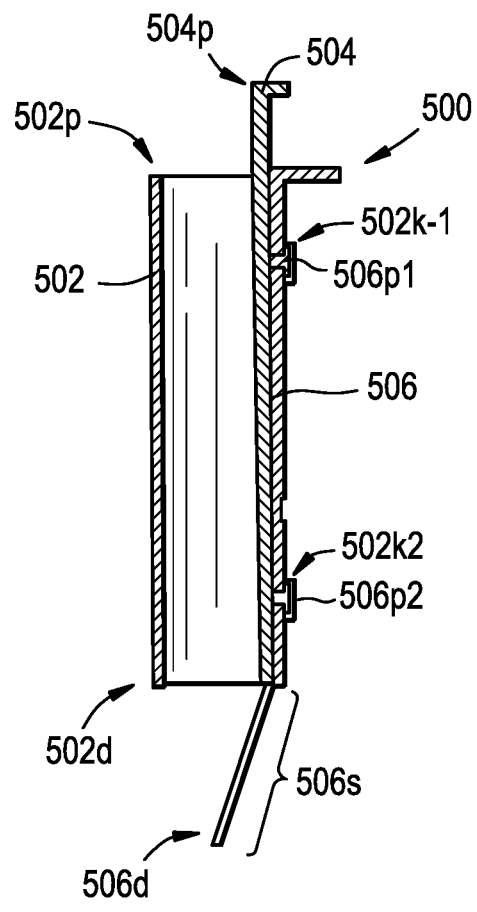
FIG. 6A is a sectional side view of another exemplary embodiment of an obstacle retracting access device.
Figure 6B:
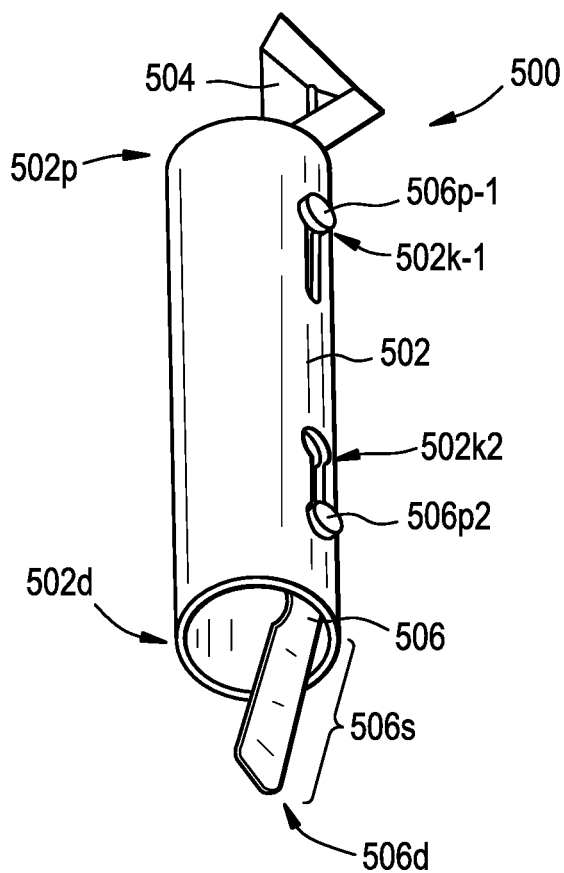
FIG. 6B is a perspective view of the access device of FIG. 6A.

FIGS. 6A and 6B illustrate another example of a surgical access device 500. The access device 500 can include one or more movable arms to retract nerve tissue or other obstacles. As illustrated, the surgical access device 500 can include an access tube 502, an expander 504, and a shield or blade 506. The access tube 502, expander 504, and shield 506 can function similar to the outer tube 402, inner tube 406, and middle tube 404 described above, in that distal advancement of the expander 504 can cause the distal end of the shield 506 to deflect radially outward and retract nerve tissue or other obstacles.

The access tube 502 can be a cylinder having an opening formed therethrough, from a proximal end 502p to a distal end 502d. The access tube 502 can have any shape or dimensions as described above, and/or as is optimal or necessary for various surgical procedures. The access tube 502 can have a length that is less than the length of the expander 504 and the shield 506. The access tube 502 can have keyholes and slotted tracks 502k1 and 502k2 that are configured to receive and limit or prevent the distal and/or proximal movement of the shield 506. The keyholes can be formed such that the slotted tracks extend distally from the keyhole portion.

The shield 506 can be attached (e.g., removably attached) to the access tube 502 using protrusions 506p1 and 506p2 (e.g., pins) formed on the outer surface of the shield 506. The protrusions 506p1 and 506p2 can be of any shape and size that can fit into the keyholes 502k1 and 502k2 and can slide along their slotted tracks. The shield 506 can be a long flat or curved blade that includes an angled arm or shielding portion 506s formed at its distal end 506d. The shield 506 can have the same or different widths along its body, as deemed optimal or necessary to engage with various nerve tissues or other obstacles in various surgical procedures.

The shielding portion 506s can be angled, in a proximal-to-distal direction, toward a longitudinal central axis of the access tube 502. That is, the shielding portion 506s can form an oblique angle with respect to the rest of the shield 506. The shielding portion 506s and/or the area at which the shielding portion 506s connects to the rest of the shield 506 can be formed of a flexible and resilient material that allows the shielding portion 506s to move radially inward and outward. The shielding portion 506s can be biased radially inward by resilient material properties of the shield. The shielding portion 506s can be angled such that the distal end thereof reaches and/or crosses the central longitudinal axis of the surgical access device 500.

The proximal end 506p of the shield 506 can include a handle that extends outwardly from the rest of the shield 506. The handle of the shield 506 can protrude at least a distance that causes the handle to engage with the proximal end of the access tube 502. The handle of the shield 506 can be used to retract and advance, proximally and distally, the shield 506.

The expander 504 can be attached and/or connected to the shield 506, such that the shield 506 can guide the longitudinal position of the expander 504. Such a configuration can allow the expander 504 to be moved distally and proximally within the opening of the access tube 502. For instance, the expander 504 can have a longitudinal recess or slot with a width that is as large as that of the shield 506. In this way, the recess or slot of the expander 504 can be connected to the shield 506 by receiving the shield 506 therein. The recess or slot of the expander 504 can be open-ended at the distal end of the expander 504, such that the expander 504 can distally advance at least to the distal end of the shield 506.

The expander 504 can include a handle or similar outward protrusion at its proximal end 504p. The handle of the expander 504 can be used to proximally and distally move the expander 504, and/or to prevent its movement beyond the proximal end of the shield 506.

Operation of the surgical access device 500 is now described in further detail. In some embodiments, the shield 506 can be provided pre-assembled (e.g., disposed within the keyholes 502k1 and 502k2) with the access tube 502 and the expander 504. Initially, the expander 504 can be disposed in a retracted position in which the distal end of the expander 504 is spaced longitudinally from the angled arm of the shield 506. In the retracted position, the distal end of the shield 506, including at least the distal end of the shielding portion 506s) can protrude through the opening at the distal end of the access tube 502. Likewise, in the retracted position, the expander 504 can be slidably engaged with the shield 506. The expander 504, in the retracted position, is not in contact with and/or engaged with the shielding portion 506s of the shield 506. Thus, the shielding portion 506s can be disposed radially inward toward the central longitudinal axis of the surgical access device 500, as shown in FIGS. 6A and 6B, under the bias of the resilient material properties of the shield.

The surgical access device 500 can be inserted into the patient's body toward a target surgical area. The surgical access device 500 can be advanced into the patient's body until at least the depth of the nerve tissue or other obstacle to be retracted. The surgical access device can be moved side to side and/or rotated to a position in which the outer side of the shielding portion 506s of the shield 506 is adjacent to the nerve tissue or other obstacle to be retracted. This way, when the shielding portion 506s is moved radially outward, the nerve tissue or other obstacle is similarly retracted.

Once the shielding portion 506s has been optimally positioned relative to the nerve tissue or other obstacle to be retracted, the expander 504 can be distally advanced or slid through the opening of the access tube 502. The expander 504 can be distally advanced using its handle. The expander 504 can slide distally as guided by the shielding portion 506. As the expander 504 slides distally, its outer surface can contact the inner surface of the shielding portion 506. As the distal end of the expander 504 engages with the shielding portion 506s, the shielding portion 506s can be deflected radially outward, e.g., to align with a straight or non-angled body of the expander 504, such that the shielding portion 506s is displaced outwardly. As the shielding portion 506s deflects outwardly, nerve tissue or other obstacles disposed radially outward therefrom can be caused to similarly move in a radially outward direction. Retracting the expander 504 in a proximal direction away from the distal end 506d of the shield 506 can allow the shielding portion 506s to return towards its resting state in a radially inward direction.

Fourth Embodiment

FIGS. 7A to 7F illustrate another exemplary embodiment of a surgical access device 600. As shown, the surgical access device 600 can include an access tube 602, a shield 604, and a wedge 606. The access tube 602 can include a hole or opening formed therethrough from a distal end 602d to a proximal end 604p. The hole or opening of the access tube 602 can be defined by a cylindrical body of the access tube, including an inner surface facing the opening, and an outer surface. The diameter of the opening formed through the access tube 602 can remain constant throughout its length or can vary along its length, for example, gradually narrowing from its proximal end 602p to its distal end 602d. The length of the access tube 602 can vary as deemed optimal or necessary for various surgeries. The access tube 602 can be configured to receive the shield 604 and the wedge 606 through its opening. In use, the wedge 606 can be translated longitudinally relative to the outer tube 602 and the shield 604 to move the distal end of the shield between a radially inward position and a radially outward position. Proximal translation of the wedge can drive the wedge between the shield 604 and the outer tube 602 to urge the distal end of the shield radially inward. Distal translation of the wedge can provide clearance to allow the distal end of the shield to move radially outward, e.g., under the bias of resilient material properties of the shield. The access device 600 can be inserted with the shield in the radially inward position, and the wedge can then be actuated to move the shield to the radially outward position and thereby retract nerve tissue or other obstacles disposed adjacent to the shield.

The shield 604 can include three portions arranged lengthwise from a proximal end 604p to a distal end 604d: a ring 604-1, a cylindrical portion 604-2 and a shield portion 604-3. The ring 604-1, positioned at the proximal end 604p of the shield 604 can have a larger external circumference, defined by the outer surface of its body. The circumference of the ring 604-1 can be large enough so that distal movement of the shield 604 through the opening of the access tube 604 can be limited by the distal end (e.g., underside) of the ring 604-1. The ring 604-1 can include a hole formed therethrough, as defined by the inner surface of its body. The diameter of the opening of the ring 604-1 can be constant throughout its length, and/or can be at least as large as the opening formed through the access tube 602. In some embodiments, the outer surface of the ring 604-2 can have a ribbed or gear-like structure that facilitates its gripping, in order to provide easier manipulation thereof, for example, to rotate the shield 604 relative to the access tube 602.

The distal end of the ring 604-1 can be connected to the cylindrical portion 604-2. The cylindrical portion 604-2 can be a partial or slotted cylinder, in which a longitudinal slot prevents the portion 604-2 from having a body having a fully-closed circumference. In such configurations, as shown for example in FIGS. 7B and 7C, the shield portion 604-3 can extend into said slot formed in the partial-cylinder cylindrical portion 604-2.

The cylindrical portion 604-2 can include an opening formed therethrough from its proximal end to its distal end. Although the diameter of the opening can vary as deemed optimal or necessary, in some embodiments, the diameter of the opening can be the same as or substantially similar to the diameter of the opening formed through the ring portion 604-1. The cylindrical portion 604-2 can be configured to slide within the opening of the access tube 602. To this end, the outer surface of the cylindrical portion 604-2 can have a circumference that is no larger than the circumference of the opening of the access tube 602, as defined by its inner walls.

The cylindrical portion 604-2 can be connected to the shield portion 604-3. The proximal end of the shield portion 604-3 can be connected to the distal end of the cylindrical portion 604-2, or elsewhere along the longitudinal slot of a partial-cylinder cylindrical portion. The shield portion 604-3 can be a long blade that, when inserted through the opening of the access tube 602, can be at least long enough to protrude through the opening at the distal end of the access tube 602. The shield portion 604-3 can be of any width deemed optimal or necessary to retract various types of nerve tissue or other obstacles. The shield portion 604-3 can be of multiple widths along its body. The shield portion 604-3 can have a flat body, or can have a curved body along its width with a degree of curvature that matches or is substantially similar to the degree of curvature of the inner surface of the access tube 602. The shield portion 604-3 can have a longitudinally straight (e.g., parallel to the inner surface of the access tube 602), curved, or angled body. At least a portion of the outer surface of the shield portion 604-3 can be in contact with the inner surface of the access tube 602 when the wedge 606 is not engaged (e.g., not disposed between the shield portion 604-3 and the access tube 602).

The shield portion 604-3 can be made of a flexible and resilient material or can be connected to the cylindrical portion 604-2 in a manner that allows the distal end of the shield portion 604-3 to move radially inward towards or across a central longitudinal axis of the surgical access device 600, as explained in further detail below. For instance, the shield portion 604-3 can be caused to move radially inward by proximally retracting the wedge 606 while disposed between the access tube 602 and the shield portion 604-3. The material or connection of the shield portion 604-3 can be such that when radially inward pressure on the shield portion 604-3 is removed, the shield portion can automatically retract or move in a radially outward direction.

The shield portion can include a longitudinal slot 604-3s formed along and penetrating through its body (e.g., through its inner surface to its outer surface). The longitudinal slot 604-3s can be configured to receive the wedge 606 therethrough such that a proximal end of the wedge 606 is positioned interior to the shield portion 604-3 and the distal end of the wedge 606 is positioned between the shield portion 604-3 and the access tube 602 (e.g., radially outward from the shield portion 604-3 and radially inward from the inner surface of the access tube 602).

The wedge 606 can be or can include a long blade or rod 606-2 and a wedging tip 606-1 connected to or formed at the distal end of the wedge 606. The wedge 606 can include a handle 606-3, which can be a tab or other external protrusion connected to or formed at the proximal end of the wedge 606. As described in further detail below, the blade 606-2 and the wedging tip 606-1 can be configured such that the wedging tip 606-1 slides proximally and distally within a space defined between the outer surface of the shield portion 604-3 and the inner surface of the access tube 602.

Figure 7A:
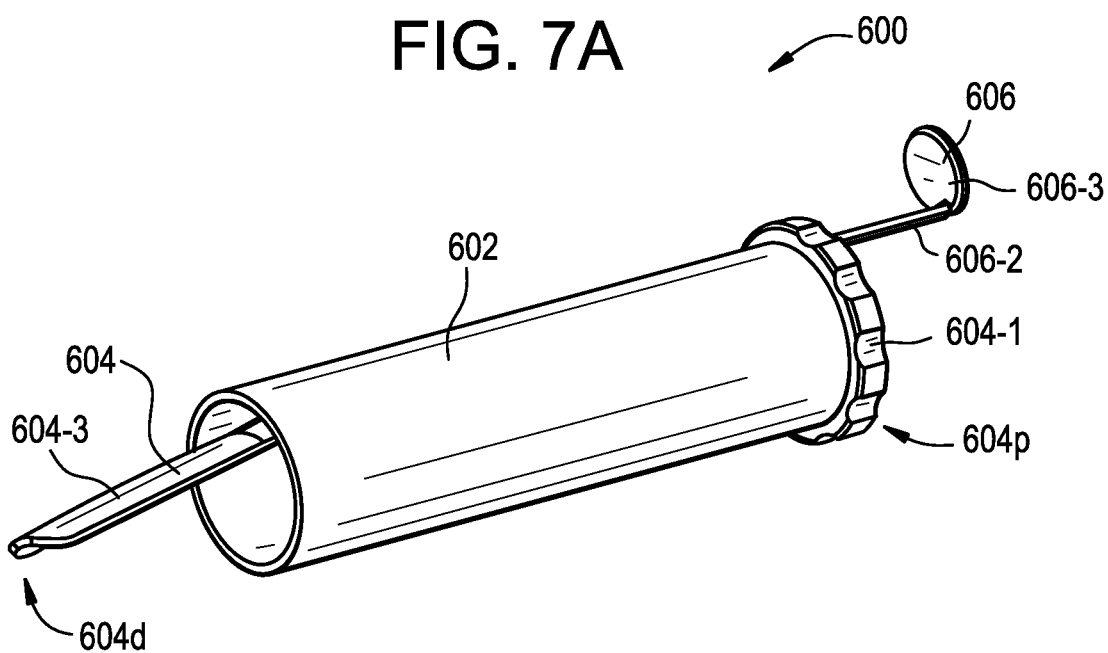
FIG. 7A is a perspective view of another exemplary embodiment of an obstacle retracting access device.
Figure 7B:
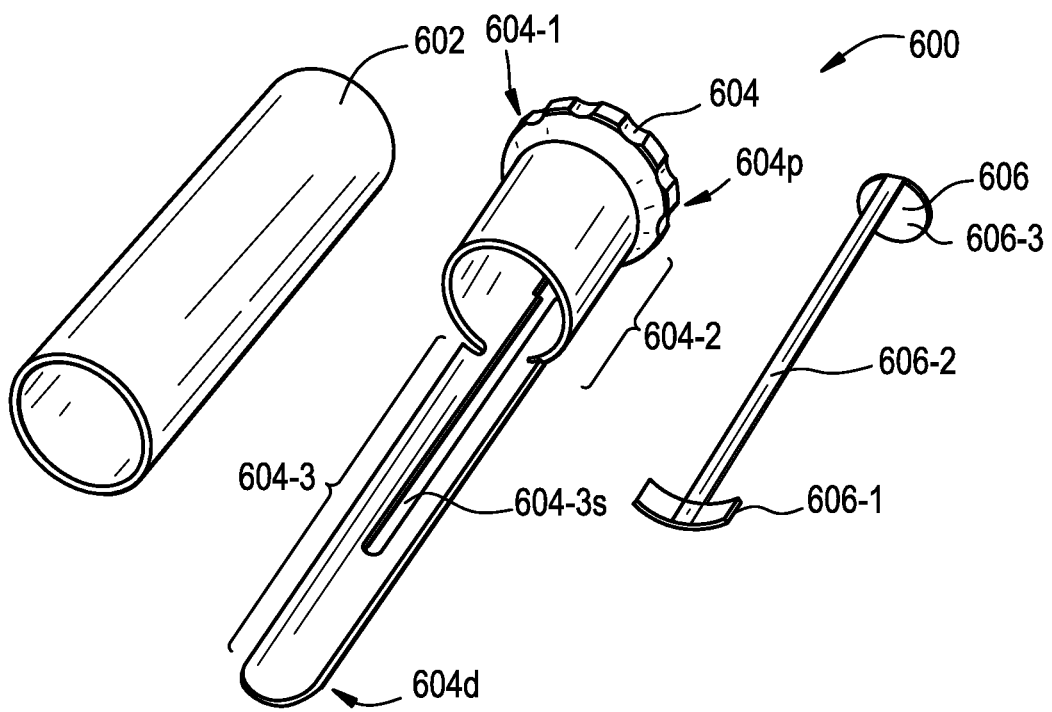
FIG. 7B is a perspective view of the access device of FIG. 7A, unassembled.
Figure 7C:
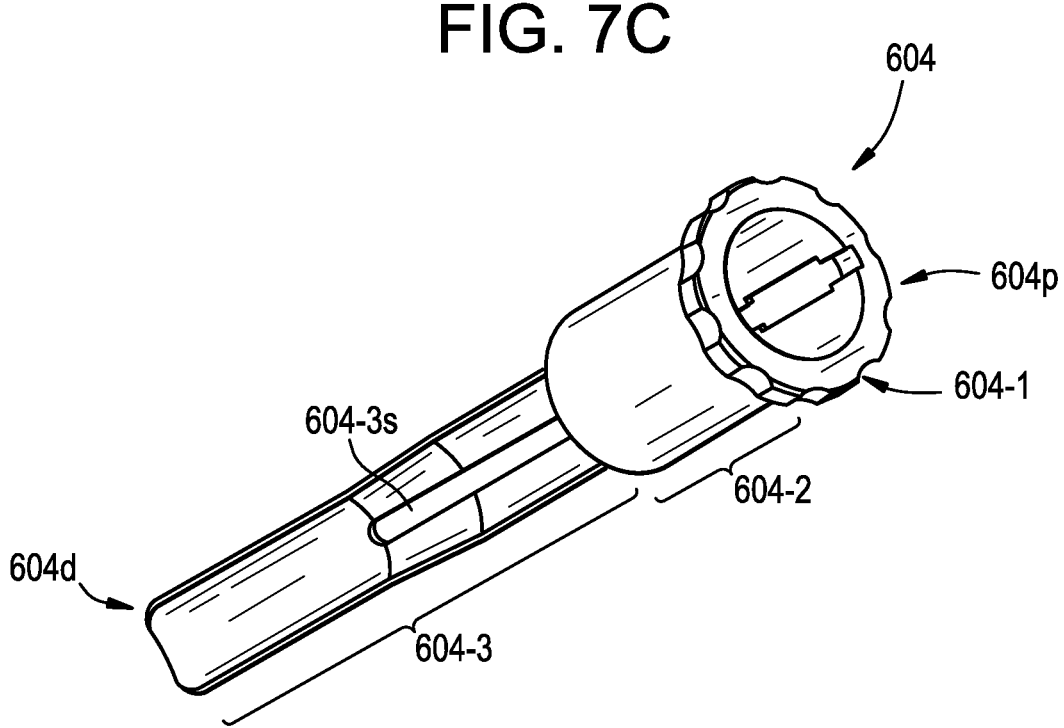
FIG. 7C is a perspective view of an exemplary embodiment of a shield of the access device of FIG. 7A.
Figure 7D:
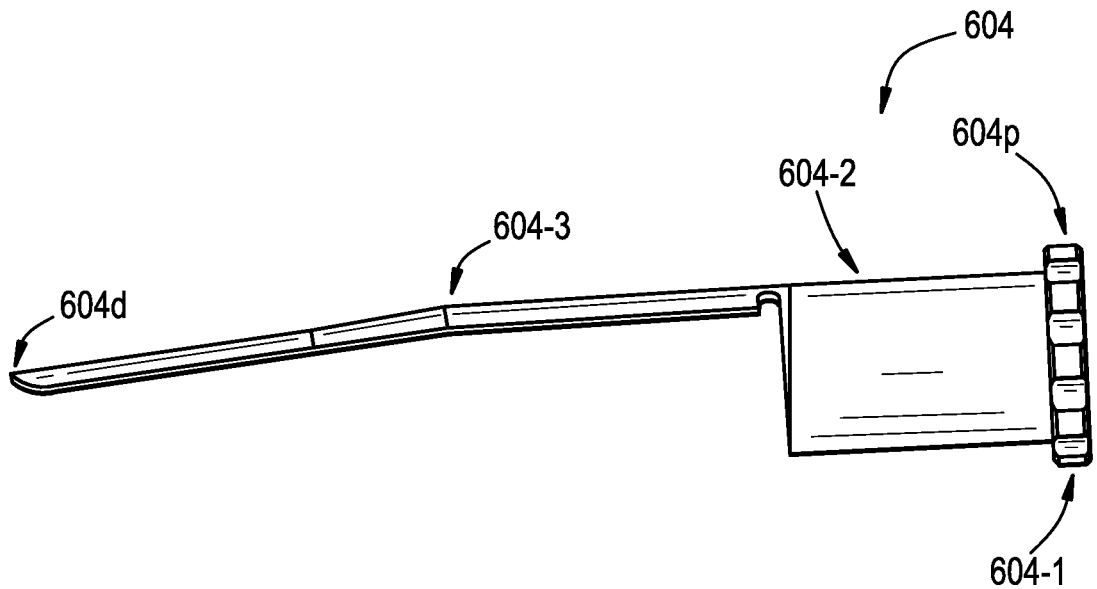
FIG. 7D is a side view of the shield of FIG. 7C.

The blade 606-2 can have any length, for example based on the length of the shield 604 or its shield portion 604-3. The blade 606-2 can have a width that is smaller than the width of the longitudinal slot 604-3s formed in the shield portion 604-3, such that the blade 606-2 can be inserted and slid proximally and distally therethrough. The wedging tip 606-1 can be formed at the distal end of the blade 606-2, and can have a width that is larger than the width of the longitudinal slot 604-3s, such that when the wedging tip 606-1 is placed in its wedging position in which its outer surface is facing the inner surface of the access tube 602, the wedging tip 606-1 does not slide within the longitudinal slot (e.g., because of its width) but rather it slides in contact with the outer surface of the shield portion 604-3 at least at areas adjacent to the longitudinal slot 604-3s. In other words, while the blade 606-2 is positioned such that it penetrates through the longitudinal slot 604-3s, the wedging tip can be disposed radially outward from the shield portion 604-3s. For example, as shown in FIG. 7B, the wedging tip 606-1 can have a winged configuration that protrudes in both directions laterally relative to the blade 606-2.

Operation of the surgical access device 600 to move or retract nerve tissue or other obstacles is now described in further detail. The surgical access device 600 can be assembled prior to insertion into the patient's body or before penetrating to the patient's surgical target area, or can be assembled in situ. In an assembled configuration of the surgical access device, the distal end of the shield 604 or shield portion 604-3 can be inserted into the opening formed at the proximal end of the access tube 602. In turn, or prior to the insertion of the shield 604 or its distal advancement through the opening of the access tube 602, the wedge 606 can be inserted through the longitudinal slot 604-3s of the shield portion 604-3. To do so, the wedging tip 606-1 at the distal end of the wedge 606 can be first inserted through the longitudinal slot, starting from a position interior to the shield portion 604-3, penetrating through the longitudinal slot 604-3s, and exiting at a position exterior to the shield portion 604-3. In this way, the proximal end of the wedge 606 can be positioned internal to the inner surface of the shield portion 604-3, and the distal end of the wedge 606 can be positioned external to the shield portion 604-3. Because the wedging tip 606-1 can be wider than the longitudinal slot 604-3s, to insert the wedge 606 through the longitudinal slot 604-3s, the wedge 606 can be positioned such that the wedging tip 606-1 penetrates the longitudinal slot at an angle.

Figure 7E:
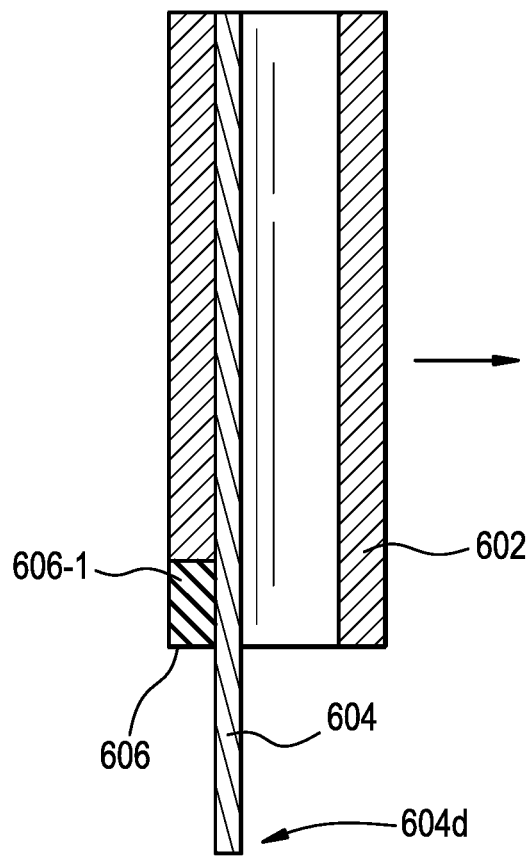
FIG. 7E and FIG. 7F are diagrams illustrating moving the access device of FIG. 7A between a radially outward configuration and a radially inward configuration.
Figure 7F:
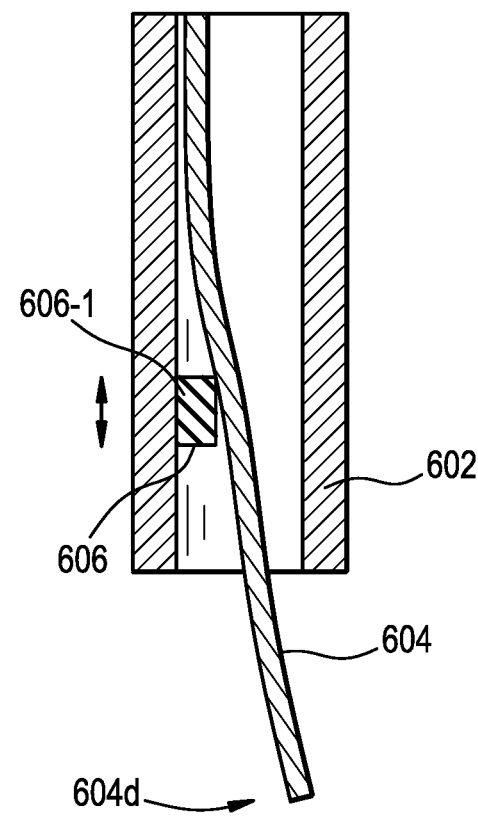

The wedge 606 can be retracted or pulled proximally relative to the access tube 602 and the shield 604, as shown in FIG. 7F. This can be done, for example, using the handle 606-3 of the wedge 606. As the wedge 606 is distally retracted, the inner surface of the access tube 602 can cause the inner surface of the wedging tip 606-1 to apply force against the outer surface of the shield portion 604-3. This force from the wedging tip 606-1 can cause the distal end of the shield portion 604-3 to deflect or move radially inward, away from the inner surface of the access tube 602 toward and/or across a central longitudinal axis of the surgical access device 600. The shield portion 604-3 can be positioned in this way prior to insertion into the patient's body or at a time prior to distally advancing the access tube to a depth at which the nerve tissue 608 or other obstacle to be moved is located.

When the distal end of the shield portion 604-3 is in its radially inward position (e.g., as shown in FIG. 7F), the surgical access device 600 can be advanced distally to a depth at or deeper than that of the nerve tissue 608 or other obstacle to be retracted. At this position, the nerve tissue 608 can be positioned adjacent to the outer surface of the shield portion 604-3. The wedge 606 can be moved distally and/or pushed, as shown in FIG. 7E, such that the force applied on the outer surface of the shield portion 604-3 by the wedging tip 606-1 is reduced or removed. As the wedging tip 606-1 is slid distally, the distal end of the shield portion 604-3 can retract or otherwise move in a radially outward direction towards its resting position, e.g., as illustrated in FIG. 7E. As the shield portion 604-3 retracts, the outer side of the shield portion 604-3 can push against and/or move the nerve tissue 608 or other obstacle in a radially outward direction. As a result, the nerve tissue 608 or other obstacle can be moved further away from the central longitudinal axis of the surgical access device 600.

Fifth Embodiment

FIGS. 8A to 8M illustrate another example embodiment of a surgical access device 700. The surgical access device 700 can include an access tube 702, a shield 704, and a cam mechanism 706. The cam mechanism 706 can be configured to cause radial movement of the shield 704 within the access tube 702. For example, the cam mechanism 706 can include a ring having a spiral-shaped slot, e.g., a slot having a radius of curvature that progressively increases along its circumference. A pin extending from the shield 704 can be received within the slot. The shield 704 can be pivotally coupled to the access tube 702. Rotation of the ring in a first direction can cause the pin to move towards a larger radius portion of the slot, pivoting the proximal end of the shield 704 radially outward and moving the distal end of the shield radially inward. Rotation of the ring in a second, opposite direction can cause the pin to move towards a smaller radius portion of the slot, pivoting the proximal end of the shield 704 radially inward and moving the distal end of the shield radially outward. Outward movement of the distal end of the shield 704 can be effective to retract nerve tissue or other obstacles disposed adjacent thereto.

The access tube 702 can be a cylinder having an opening formed therethrough, from a distal end 702d to a proximal end 702p. The access tube 702 can have any length, shape, diameter of opening, and other characteristics, as deemed optimal or necessary to perform various surgical procedures. The length of the access tube 702 can be less than the length of the shield 704, such that the distal end of the shield 704 can protrude through the opening formed at the distal end 702d of the access tube 702.

The access tube 702 can include a longitudinal slot 702s extending from the proximal end 702p of the access tube 702 to a point along the length of the access tube 702. The longitudinal slot can form a hole through the body of the access tube, from the inner surface through the outer surface. The longitudinal slot 702s can have a width around the circumference of the access tube 702 that is at least as wide as the width of the shield 704, such that the shield 704 can penetrate therethrough. In some embodiments, the longitudinal slot 702s can have varying widths that are enabled to prevent the further distal movement of the shield 704, e.g., by engaging with a part of the shield 704. For instance, the longitudinal slot can have a first narrower width along its most distal region, and a second wider width along its most proximal region.

The shield 704 can be a long blade that is used to move or retract tissue at its distal end. The shield 704 can have the same or varying lengths along its body. The shield 704 can be longer than the access tube 702. The shield 704 can have a flat body or a body that is curved with a same or similar degree of curvature as that of the inner surface of the access tube 702. The shield 704 can include two widths: a first, larger width starting at its proximal end, and a second, smaller width ending at the distal end. The portion of the shield 704 having the larger width can be at least larger than the width of the smallest-width portion of the longitudinal slot 702s of the access tube 702. In some embodiments, the portion of the shield 704 having the smaller width can be at least smaller than the width of the largest-width portion of the longitudinal slot 702s of the access tube 702. Such a configuration can allow the portion of the shield 704 having the larger width to be retained outside of the access tube 702, since its distal or inward movement is prevented by the larger width relative to that of the longitudinal slot 702s, while the portion of the shield 704 having the smaller width can penetrate the longitudinal slot, moving distally and proximally therethrough, while remaining within the opening and/or inner surfaces of the access tube 702. In some embodiments, when the distal end of the shield 704 is moved radially as explained in further detail below, it can pivot about access tube 702, for instance, at the point where the width of the shield 704 changes from the larger width to the smaller width.

The proximal end of the shield 704 can include a pin 704-1 or similar extension formed thereon, extending in a proximal direction from the proximal end of the rest of the body of the shield 704. The pin 704-1 can be configured to fit within and slide within a slot formed in the cam mechanism 706. Thus, the shape and/or dimensions of the pin 704-1 can vary as needed to engage with the cam mechanism 706.

The cam mechanism 706 can include a cylinder or ring having an opening formed therethrough. The circumference of the opening of the cam mechanism 706 can be at least as large as the circumference of the outer surface of the access tube 702, such that the access tube 702 can be inserted through the opening of the cam mechanism 706. The cam mechanism 706 can include a body having inner and outer surfaces, a proximal-facing surface, and a distal-facing surface. The inner surface of the cam mechanism 706 can define the opening of the cam mechanism.

The cam mechanism 706 can include a circumferential slot 706s formed through the body of the cam mechanism, penetrating through the distal-facing surface and/or the proximal-facing surface. The slot 706s can be configured to guide the pin 704-1 of the shield 704. The slot 706s can be sufficiently wide to receive the pin 704-1 of the shield 704. The slot 706s can be of any circumferential length deemed optimal or necessary to cause or allow sufficient radial movement of the shield 704. The slot 706s can be formed around 25% or more of the circumference of the cam mechanism 706. The slot 706s can have an increasing and/or decreasing radius from one of its ends to the other, such that the slot 706s forms part of a spiral rather than a circle. In other words, one end of the slot 706s can be located a further distance from the center of the opening formed through the cam mechanism 706 than the other end of the slot 706s. This way, as the cam mechanism 706 is rotated clockwise or counterclockwise relative to the access tube 702, the pin 704-1 of the shield 704 can slide within the slot 706s, forcing the proximal end of the shield 704 to pivot or move in a radially inward or outward direction relative to the opening of the cam mechanism 706, as described in further detail below.

The outer surface of the distal end of the cam mechanism 706 can have a smaller diameter than that of the rest of the cam mechanism 706 (e.g., its proximal end). This smaller diameter portion of the cam mechanism 706 can be used to capture or prevent undesired movement of the cam mechanism 706, by engaging with a ring 708 that is slidably connected to the access tube 702. That is, the ring 708 can include an opening large enough to receive the distal end of the cam mechanism 706, but small enough to stop the larger, proximal end of the cam mechanism 706 from passing therethrough. The ring 708 can thus prevent further distal movement of the cam mechanism 706, to ensure that the cam mechanism remains at a sufficiently proximal area of the access tube 702.

Figure 8A:
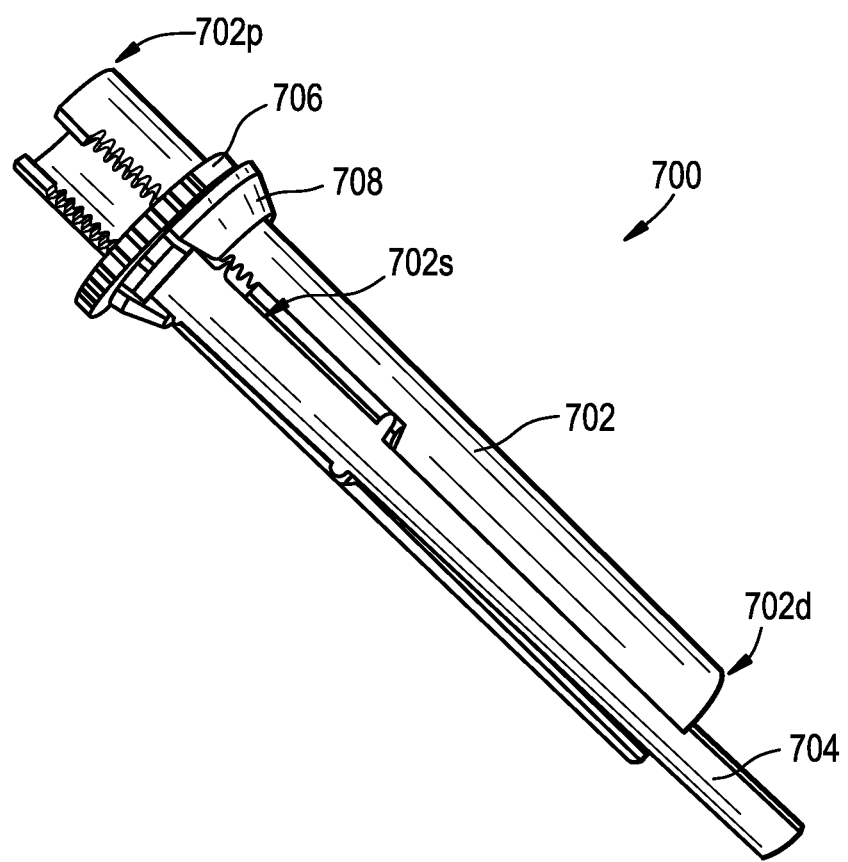
FIG. 8A is a perspective view of another exemplary embodiment of an obstacle retracting access device.
Figure 8B:
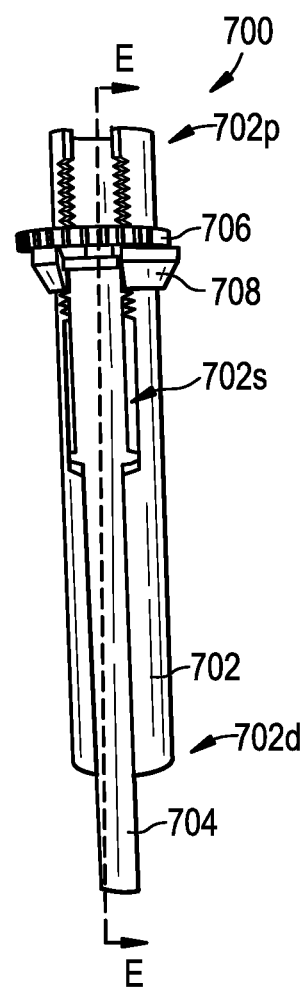
FIG. 8B is a side view of the access device of FIG. 8A.
Figure 8C:
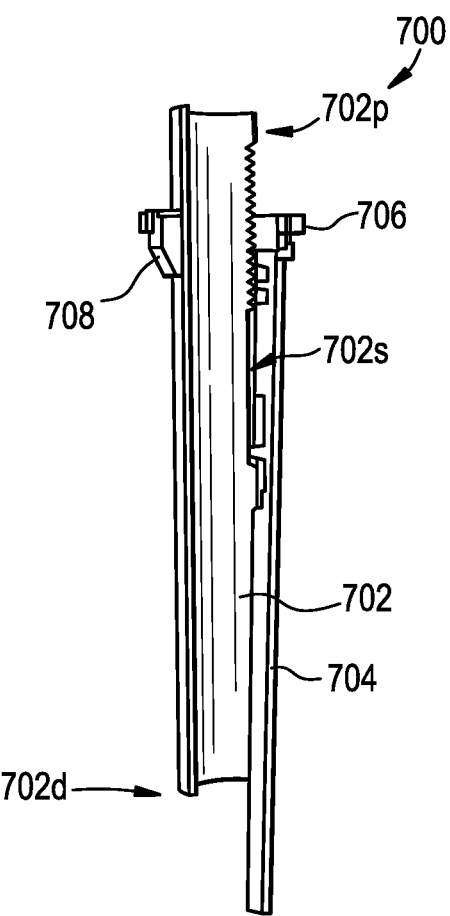
FIG. 8C is a sectional side view of the access device of FIG. 8B taken along the line E-E.
Figure 8F:
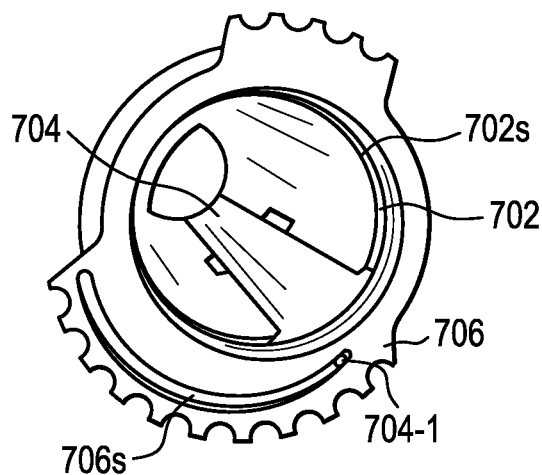
FIG. 8F is a diagram illustrating a top view of the access device of FIG. 8A in a radially-outward configuration.
Figure 8G:
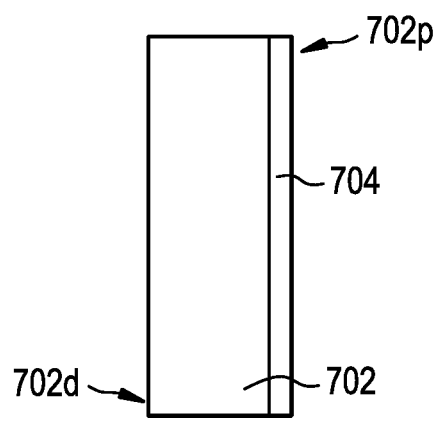
FIG. 8G is a diagram illustrating a side view of an access tube and shield of the access device of FIG. 8F.
Figure 8H:
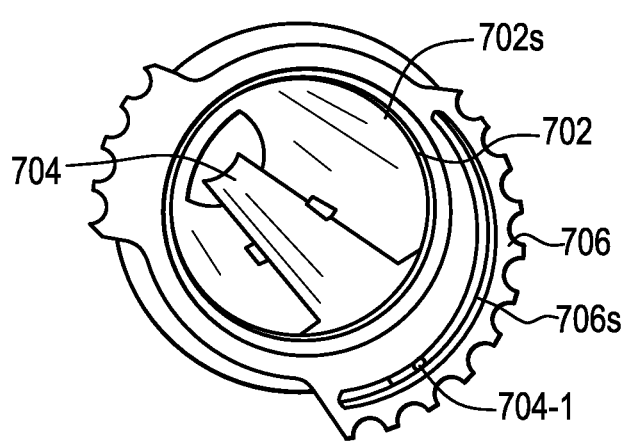
FIG. 8H is a diagram illustrating a top view of the access device of FIG. 8A in a radially-inward configuration.
Figure 8I:
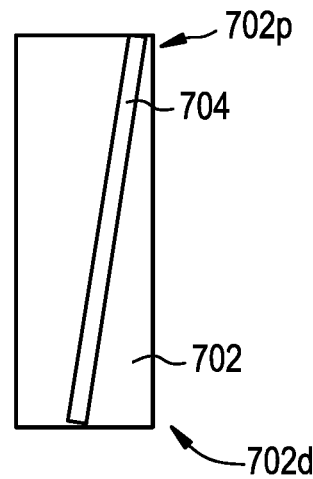
FIG. 8I is a diagram illustrating a side view of an access tube and shield of the access device of FIG. 8H.

Operation of the surgical access device 700 to radially move (e.g., retract) nerve tissue or other obstacles during a surgical procedure is now described in further detail. As shown in FIGS. 8F and 8G, the surgical access device 700 can be set to a retracted position in which: the pin 704-1 of the shield 704 is positioned at the end of the slot 706s having the shortest distance to the center of the opening of the cam mechanism 706 (e.g., the most radially inward point of the slot 706s) and the radially inward position of the pin 704-1 causes the distal end of the shield 704 to remain in a radially outward position adjacent to and/or in contact with the inner wall of the access tube 702, e.g., by not forcing the shield 704 to pivot, move, or deform. As shown in FIGS. 8H and 8I, the surgical access device 700 can be set to a non-retracted position in which: the pin 704-1 of the shield 704 is positioned at the end of the slot 706s having the greatest distance to the center of the opening of the cam mechanism 706 (e.g., the most radially outward point of the slot 706s) and the radially outward position of the pin 704-1 causes the distal end of the shield 704 to remain in a radially inward position such that it approaches or crosses the central longitudinal axis of the access tube 702. The device 700 can be positioned in any of an infinite number of positions intermediate the retracted and non-retracted positions, allowing the degree of retraction to be precisely controlled by rotation of the cam mechanism, The surgical access device 700 can be inserted into the patient's body and/or advanced toward a target surgical area having a nerve tissue therein. As shown in FIGS. 8H and 8I, the cam mechanism 706 can be rotated counterclockwise relative to the access tube 702. As the cam mechanism 706 is rotated counterclockwise: (1) the pin 704-2 of the shield 704 slides along the slot 706s toward the end of the slot 706s having the furthest distance to the center of the opening of the cam mechanism 706 (e.g., the most radially outward point of the slot 706s); (2) the gradual radially outward movement of the pin 704-1 causes the proximal end of the shield 704 to move radially outward relative to the opening of the cam mechanism 706, and the distal end of the shield 704 to pivot in a radially inward direction, toward the central longitudinal axis of the access tube 702 and away from the inner surface of the access tube 702. The gradual radial outward configuration of the slot 706s allows for the gradual radial movement of the distal end of the shield 704. The cam mechanism 706 can thus be partially rotated (e.g., to a position between its ends (e.g., 50% rotated)) until the desired amount of radial movement of the distal end of the shield 704 or retraction of the nerve tissue is achieved.

Figure 8J:
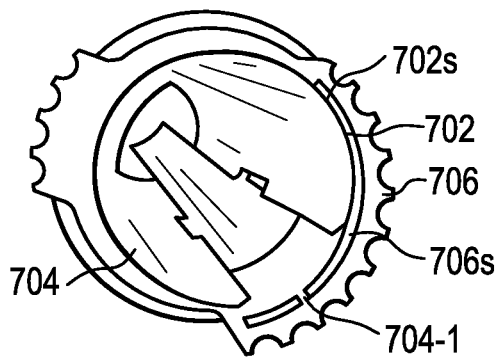
FIG. 8J is a diagram illustrating a top view of the access device of FIG. 8A in a radially-inward and longitudinally-advanced configuration.
Figure 8K:
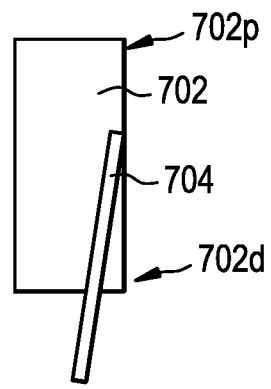
FIG. 8K is a diagram illustrating a side view of an access tube and shield of the access device of FIG. 8J.

As shown in FIGS. 8J and 8K, with the distal end of the shield 704 moved to a desired radial inward position, the blade can be distally advanced relative to the access tube, toward the nerve tissue or other obstacle to be moved, to a position at or beyond the depth of the nerve tissue or other obstacle. The shield 704 can be positioned such that the nerve tissue or other obstacle to be moved is disposed radially outward from an outer surface of the distal end of the shield 704. This position can enable the shield 704 to move the nerve tissue in a radially outward direction as the shield 704 itself moves radially outward. To advance the shield 704 to a desired longitudinal position and/or control the depth of the position of the distal end the shield 704, the cam mechanism 706 can be distally and proximally retracted to a desired position relative to the access tube 702 by pulling and pushing the cam mechanism 706.

Figure 8L:
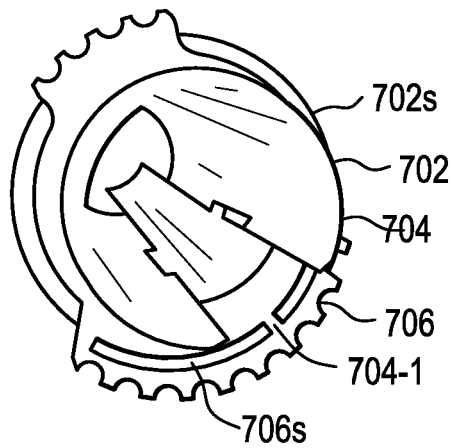
FIG. 8L is a diagram illustrating a top view of the access device of FIG. 8A in a radially-outward and longitudinally-advanced configuration.
Figure 8M:
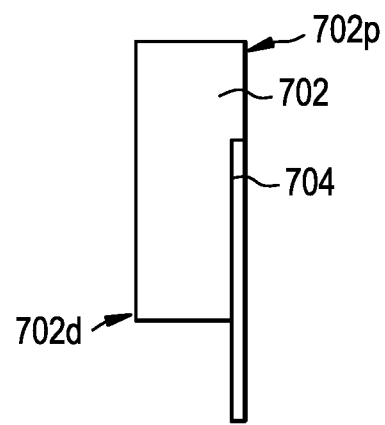
FIG. 8M is a diagram illustrating a side view of an access tube and shield of the access device of FIG. 8L.

As shown in FIGS. 8L and 8M, the cam mechanism 706 can be rotated in a clockwise direction, in the opposite manner as described above in connection with FIGS. 8H and 8I, causing the distal end of the shield 704 to move radially outward and the nerve tissue to retract. That is, as the cam mechanism 706 is rotated in a clockwise direction, the pin 704-1 of the shield 704 can slide along the slot 706s toward the end of the slot 706s positioned closest to the center of the opening of the cam mechanism. This radially inward movement of the pin 704-1 can cause the proximal end of the shield 704 to also move radially inward relative to the opening of the cam mechanism 706. The radially inward movement of the proximal end of the shield 704 can cause the shield 704 to pivot about the access tube such that its opposite, distal end moves in the radially outward direction relative to the opening of the access tube 702, to a position adjacent to or more parallel with the inner surface of the access tube 702. The radially outward movement of the distal end of the shield 704 can cause a radially outward force to be applied on the nerve tissue or other obstacle positioned adjacent to the shield 704, by the outer surface of the distal end of the shield 704. The nerve tissue or other obstacle can thus be driven radially outward. The cam mechanism 706 can be partially or fully rotated in the clockwise direction, until the desired amount of retraction of the nerve tissue or other obstacle is achieved.

Sixth Embodiment

FIGS. 9A to 9C illustrate another example embodiment of a surgical access device 800. The surgical access device 800 can include an access tube 802 and a blade 804. The blade 804 can include a finger portion 804-1 attached thereto that is configured to cause the inner blade 804 to move radially inward and outward within the access tube 802, in order to facilitate the retraction of nerve tissue or other obstacles during a surgical procedure. In use, the access tube 802 can slide between the finger portion 804-1 and the blade 804. When the user pushes distally on a handle portion of the blade, the finger can be deflected and the distal end of the blade can move radially inward towards the center of the access tube. The user can hold the device in this state during initial insertion and while positioning the distal end of the blade at the depth of the nerve tissue or other obstacle to be retracted. The user can then release the distal pressure on the blade, allowing resilient properties of the spring finger to cause the blade to pivot back to the starting point, moving the distal end of the blade radially-outward to retract the nerve tissue or other obstacle.

As illustrated, the access tube 802 can be a cylinder having a distal end 802d and a proximal end 802p. The access tube 802 can include an opening or hole formed through its body, extending through the distal and proximal ends 802d and 802p, respectively. The opening of the access tube 802 can be defined by the inner surface of the access tube. The length, shape and other characteristics of the access tube 802 can vary as deemed optimal or needed to perform various surgical procedures.

The access tube 802 can be configured to receive the inner blade 804 through its proximal end 802p. The inner blade 804 can be a long structure having a handle region 804h, and a body 804b. As described in further detail below, the inner blade 804 can include a finger portion 804-1. When assembled, the body of the access tube 802 can be disposed between the finger 804-1 and the body 804b of the blade 804. The handle region 804h and the body 804b can connect and/or meet along a curved or angled region. As shown in FIGS. 9A and 9B, the inner blade 804 can have a curved or angled tip 804t at its distal end, to engage with and/or facilitate movement of the nerve tissue or other obstacle to be retracted. The inner blade 804 can be of any length, width, and/or shape as deemed optimal or necessary to function with the access tube 802.

The length of the inner blade 804 can be at least long enough such that its distal end can protrude through the distal end of the access tube 802 in order to engage with the nerve tissue or other obstacle. In other words, the body 804b of the inner blade 804 can be longer than the access tube 802, and in some cases, as least sufficiently longer such that the amount of length of the body 804b of the inner blade 804 that protrudes through the distal end of the access tube 802 is sufficient to optimally engage with the nerve tissue or other obstacle. The inner blade 804 can have varying widths and shapes throughout its length. For instance, the body 804b can have a different width and shape than the handle 804b of the inner blade 804. The body 804b of the inner blade 804 can be curved in the same or substantially the same manner as the inner surface of the access tube 802, while the handle 804h can be flat. Areas of a portion or region of the inner blade 804 can vary in shape and/or dimensions. For instance, a proximal end of the handle 804h can be curved and wide enough to provide optimal engagement with a user's thumb, e.g., while the distal end of the handle 804h can be flat and narrower.

The handle 804h can be a portion of the inner blade 804 that extends outwardly relative to the body 804b and/or the access tube 802. The handle 804h can be of any length (e.g., protrude or extend from the body 804b) deemed optimal or necessary to be manipulated by a user. The tip 804t can also have any size, shape or dimension deemed optimal or necessary to engage with and/or retract nerve tissue.

As shown in FIGS. 9A to 9C, the inner blade 804 can include a finger 804-1 that is configured to engage with the access tube 802 and cause the body 804b of the inner blade 804 to move radially within the opening of the access tube 802. The finger portion 804-1 can have a form substantially mirroring that of the handle and body portions 804h and 804b, respectively of the inner blade 804. The finger portion 804-1 can have a length that is less than those two portions. A proximal-facing surface of the proximal end of the finger portion 804-1 of the inner blade 804 can be connected to a distal-facing surface of the handle 804h, e.g., at a single point or at a portion thereof. The finger portion 804-1 can curve or angle similarly to the inner blade 804, and its distal end can extend distally toward the tip 804t. In some embodiments, the portion of the finger 804-1 adjacent to its distal end can be parallel to the body 804*b*. The finger 804-1 can be curved or angled such that its distal end extends away from the body 804*b*. The distal end of the finger 804-1 can be positioned sufficiently close to the body 804*b* and/or the access tube 802 such that its inner surface can make contact with the outer surface of the access tube 802 when assembled thereto.

Operation of the surgical access device 800 is now described in further detail. As shown in FIG. 9A (in solid lines), in its default position, the access tube 802 can be disposed such that its body is positioned between the body 804*b* of the inner blade 804 and the finger portion 804-1. That is, the outer surface of the blade 804*b* can face the inner surface of the access tube 802, and the inner surface of the finger portion 804-1 can face the outer surface of the access tube 802. When the inner blade 804 is inserted into the access tube 802, the inner blade 804 can make contact with the access tube 802, e.g., at a portion of the body at the proximal end of the access tube 802 and at a distal-facing side of the inner blade 804 (e.g., at or approximately at the curved or angled area where the body 804*b* meets the handle 804*h*). In this default position, the distal end and/or tip 804*t* of the inner blade 804 can be disposed radially outward within the opening of the access tube 802.

Prior to advancing the surgical access device within the patient to a depth where the tip 804*t* or the distal end of the inner blade 804 is at or beyond the depth of the nerve tissue or other obstacle to be retracted, the inner blade 804*t* can be activated to properly position the nerve tissue relative to the inner blade 804 for retraction. To activate the inner blade 804, the handle 804*h* can be pressed in a downward or distal direction. Due to the position of the proximal end of the finger portion 804-1 below the handle 804*h*, the pressure or force applied to the handle 804*h* can also, in part, be applied to the finger 804-1. The downward force on the handle 804*h* can cause the body 804*b* and the distal end of the finger portion to rotate inwardly towards the access tube in the direction D illustrated in FIG. 9A.

The close proximity of the finger portion 804-1 to the outer surface of the access tube 802 can cause the finger portion to make contact therewith, as it pivots due to the force on the handle 804*h*. This contact with the access tube can prevent any further pivoting of the finger portion 804-1. However, due to the flexibility of the finger portion, movement of the body 804*b* can continue in the direction of the illustrated arrow. Accordingly, the force being applied on the handle 804*h* can cause the deflection of the distal end or tip 804*t* of the inner blade 804 radially inward, while the finger 804-1 remains statically in contact with the access tube 802. As a result, the distal end and/or tip 804*t* of the inner blade 804 can move radially inward.

The surgical access device 800 can be advanced distally, while the force applied on the handle 804*h* is maintained, such that the distal end or tip 804*t* of the inner blade 804 is at or beyond the depth of the nerve tissue or other obstacle to be moved. The surgical access device 800 can be positioned such that the outer surface of the distal end of the inner blade 804 is adjacent to and/or in contact with the nerve tissue to be retracted.

Once the nerve tissue has been positioned radially outward relative to the inner blade 804, the pressure applied on the handle 804*h* can be removed or released. Because of the material properties and configuration of the inner blade 804 and its finger portion 804-1, the inner blade 804 can bias the blade towards its default position described above, by moving radially outward toward and/or adjacent to the inner surface of the access tube 802. The biasing of the distal end of the inner blade 804 can cause an outward pressure to be applied on the nerve tissue. This pressure can cause the nerve tissue or other obstacle to retract in the same, outward direction.

Any of the devices described herein can include blade or shield portions that are configured or designed to create offsets, such that nerve tissue or other obstacles (collectively or interchangeably referred to in some embodiments as "nerve tissue") can be partially retracted. For instance, partial retraction can include retraction of the nerve tissue such that it is not radially moved to or beyond the external or outward circumference of the access tube or a working area formed thereby.

FIGS. 10A and 10B illustrate example embodiments of surgical access devices 900A and 900B, respectively, having respective inner blades with offsets that enable partial retraction of nerve tissue. In FIG. 10A, the access device 900A includes an access tube 902A and an inner blade 904A that can be used to move or retract nerve tissue 906A. The access tube 902A forms a working area 910A at and extending distally from the distal end of the access tube 902A. Likewise, in FIG. 10B, the access device 900B includes an access tube 902B and an inner blade 904B that can be used to move or retract nerve tissue 906B. The access tube 902B forms a working area 910B at and extending distally from the distal end of the access tube 902B. As described in further detail below, the access devices 900A and 900B are configured such that the distal ends of the inner blades 904A and 904B are offset or form respective offsets 912A and 912B relative to the outer perimeter of the working areas 910A and 910B. The working areas can have the same or substantially the same circumference or perimeter and central longitudinal axis as the distal end of the access tubes. As a result of the offsets 912A and 912B, the distal ends of the inner blades do not fully retract to or beyond the outer circumference of the working areas 912A and 912B, thereby likewise reducing or preventing the nerve tissue's full retraction to or beyond the outer circumference of the working areas.

Although not illustrated in FIGS. 10A and 10B, the inner blades 904A and 904B can be moved or actuated (e.g., moved radially inward and outward) in various ways and using various configurations as described herein, including rotating, pushing, pulling, pivoting and the like.

As shown in FIG. 10A, the inner blade 904A can have a longitudinal body extending from a proximal end 904A-p to a distal end 904A-d. The distal end 904A-d of the inner blade 904A can be disposed at a position that is further radially inward than that of the proximal end 904A-p. Although in FIG. 10A the distal end 904A-d is staggered further radially inward by way of a perpendicular portion of the inner shield 904A, it should be understood that the distal end 904A-d can be so disposed in any of a number of ways, including a portion of the inner shield 904A having an inward curve or angle.

In FIG. 10A, the inner blade 904A is shown in a radially outward position, in which the tissue 906A is retracted away from the central longitudinal axis of the access tube 902. Nonetheless, even in such a radially outward position of the inner blade 904A shown in FIG. 10A, the distal end 904A-d is disposed radially inward as compared to the radially inward-outward position of the proximal end 904A-p. As a result, the obstacle 906A is retracted or moved in the radially outward direction, but only to a position that is not at or beyond the circumference of the working area 910A, and/or not at or beyond the radial position of the proximal end 904A-p.

As shown in FIG. 10B, the inner blade 904B can have a longitudinal body extending from a proximal end 904B-p to a distal end 904B-d. The inner blade 904B can be disposed at an angled position such that the distal end 904B-d of the inner blade 904B is disposed further radially inward than that of the proximal end 904B. This angled configuration of the inner blade 904B can be achieved using a block 908 or similar offset portion that extends radially inward, away from the inner wall of the access tube 902 and toward the central longitudinal axis of the access tube 902. The block 908 can be positioned at or along various lengths of the inner wall of the access tube 902. The block 908 can interfere with radially-outward movement of the distal end of the blade, thereby limiting the amount of retraction. By virtue of the block 908, the distal end 904B-d of the inner blade 904B can be controlled such that it does not outwardly retract to or past the circumference of the working area 910B.

In FIGS. 10A and 10B, the disposition of the distal ends of the inner blades 904A and 904B away from the outer circumference of the working areas 910A and 910B when in their retracted positions therefore creates offsets 912A and 912B relative to the outer circumference of the respective working areas. The nerve tissues 906A and 906B can therefore be partially retracted to a position that is less than to or beyond the outer circumference of the working areas. Such partial retraction of the nerve tissues 906A and 906B can prevent the nerve tissues from being overly retracted or retracted beyond their respective preferable or optimal positions, thereby preventing rupturing or otherwise negatively impacting the nerve tissues 906A and 906B.

Any of the devices described herein can be configured to limit or minimize the force applied to retracted nerve tissues or other obstacles (collectively or interchangeably referred to in some embodiments as "nerve tissue" or "nerve tissues"). As described herein, access devices can include inner blades or shields (collectively or interchangeably referred to in some embodiments as "inner blade" or "inner blades") that are configured to retract nerve tissue by applying a radially outward force thereon. For example, such outward force can be applied upon the retracted nerve tissue by a distal end of an inner blade by actuating the inner blade through a manipulation (e.g., pull, push, rotate, pivot, etc.) on a proximal end or portion of the inner blade. The inner blade can be configured in various ways to limit the amount of force that is caused by the manipulation, transferred to the distal end of the inner blade, and applied on the nerve tissue.

For example, the inner blade (or a portion thereof) can be formed of a flexible or malleable material that allows the inner blade to bend, deform, spring or the like by opposite (e.g., radially inward) force applied thereto by the resistance of the nerve tissue being retracted. Similarly, the inner blade can have a wall thickness that is sufficiently small to also allow for its deformation or the like as a result of opposite force caused by the resistance of the nerve tissue being retracted. In some embodiments, the wall thickness can vary along the length of the inner blade, such that at least a portion of the inner blade is sufficiently thin to enable its deformation. For instance, the distal end or a mid-section of the inner blade can have a smaller wall thickness than other portions thereof such as the proximal end.

Another example of an inner blade configured to minimize or limit the amount of force applied on a nerve tissue includes an inner blade that has one or more gaps or cutouts. Such gaps or cut-outs can be of different lengths and/or widths and can extend in various directions. The gaps or cut-outs can form a multi-finger (or finger-like) distal end or distal portion of the inner blade. When a radially outward force is applied by the distal end of the inner blade on the nerve tissue, an opposite radially inward force caused by the resistance of the nerve tissue is applied back on the distal end of the inner blade, which can cause the blade to flex at the cut-outs to limit the radially outward force applied to the nerve tissue.

By virtue of the cut-outs formed on the inner blade, the force applied on the nerve tissue can be reduced and thus, unwanted or excessive force on the nerve tissue can be reduced or avoided to prevent tearing or other negative impacts thereon.

Any of the devices described herein can include access tubes that vary in structure or operation from what is shown. Any of the devices herein can include an access tube in the form of a closed tubular body. Any of the devices herein can include an access tube in the form of a multi-bladed retractor. The retractor can be configured to radially expand and/or contract. The retractor can include blades that can be toed inward or outward. Exemplary access devices that can be used with any of the devices herein are described in U.S. Pat. No. 7,491,168, titled "Surgical Retractor Systems and Illuminated Cannulae," issued on Feb. 17, 2009 which is incorporated herein by reference in its entirety. Any of the devices herein can include an access tube that forms less than a full/closed circle, or that has a non-circular transverse cross-section.

The devices herein can be used to retract any type of tissue, implant, or other object or obstacle. For example, the devices herein can be used to retract nerves, blood vessels, ductile structures, dura, brain tissue, nerve roots, arteries, veins, pulmonary veins, ligaments, tendons, lymphatic vessels, organs, hollow structures, and the like.

The outer tube of the device can be held rigidly and the inner member can be inserted and manipulated to retract the obstacle. An instrument can be inserted through the working channel of the device. The instrument can be a drill guide, suction instrument, needle, screw, laser, or the like.

The devices herein can be used to retract tissue during surgery to repair a craniofacial fracture, e.g., during drilling or tapping of screws. The craniofacial fracture can be to the mandible or maxillary skeleton.

The devices herein can be used in airway surgery, such as direct laryngoscopy. The outer tube can be inserted into a patient's mouth to the base of the tongue, and the inner member can be inserted through the outer tube to protrude from a distal end thereof to retract tissue or other obstacles distal to the outer tube. A laser, needle, cautery device, scope, or other instrument can be inserted through the outer tube to perform a desired procedure on the larynx, airway, or other surgical site. The inner member can be used to retract a vocal cord, mucosa, tonsillar pillar, tongue base, larynx, or other obstacles. The devices herein can be used in robotic surgery.

The devices herein can be used to facilitate vascular access. For example, the devices herein can be used to hold a vessel while placing a catheter or other instrument into the vessel. In a patient who is in trauma with heavy blood loss, it can be very difficult to find a vein and get a line inserted. In these cases, it may be necessary to form a skin incision to expose a major vessel such as the subclavian or jugular veins. The devices herein can be used to hold structures in these critical areas to make catheter placement easier. For example, the inner member can be actuated to hold a vessel in a desired location, while a catheter is introduced into the vessel. By way of further example, the devices herein can be used for vascular access in oncology/chemotherapy, dialysis, or other applications.

The devices herein can be used in parotid surgery to retract the facial nerve. The devices herein can be used in mediastinoscopy to retract pulmonary vessels. The devices herein can be used in thyroid surgery to retract the recurrent laryngeal nerve.

The devices herein can be used in transrectal surgery, e.g., to maintain the desired plane when performing dissection. The inner member can be used to perform circumferential coring (e.g., by rotating or sweeping it within the outer tube) while the outer tube maintains the rectal lumen. The lateral and/or distal edges of the inner member can be sharpened or blade-like to facilitate such coring. This technique can be used to remove mucosa or other growth once aligned with the desired plane of the rectum.

The devices herein can include a radially-expandable outer tube or access device. The access device can be expanded to enhance retraction.

The devices herein can be used when applying plates or screws to repair a mandibular fracture or other maxillofacial fracture. The inner member can retract a nerve while a screw, drill, or other object is inserted through the outer tube. The nerve can be a facial nerve, a nerve of the upper neck, a hypoglossal nerve, a lingual nerve, and various other motor or sensory nerves that may be encountered.

The devices herein can be used to retract and protect nerves when applying external distracters for patients with small hypoplastic mandibles, repairing congenital craniofacial abnormalities, clefts, etc.

The devices herein can include a rigid inner member that is selectively deployed distally from the outer tube and can radially rotate around the working channel following the diameter of the outer tube. In other arrangements, the inner member can be flexible and/or resilient, e.g., having a known spring value based on the specific anatomical structure being swept/stretched out of the way. In this manner, the spring force can be selected to be just enough to move the structure aside, without necessarily stretching it all the way to the outer diameter of the outer tube.

The devices herein can include an inner member in the form of a deployable hollow cylinder balloon or inflatable tube. The balloon can be inflated to deploy the balloon from the distal end of the outer tube, or to diametrically expand the balloon, to retract or protect obstacles distal to the outer tube. In some embodiments, the device can include a rigid outer tube with a softer semi-flexible inner balloon tube selectively deployable from a distal end of the outer tube.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

While various example embodiments have been described above, it should be understood that they have been presented by way of example, and not limitation. It is apparent to persons skilled in the relevant art(s) that various changes in form and detail can be made therein. Thus, the disclosure should not be limited by any of the above described example embodiments.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

One skilled in the art will appreciate further features and advantages of the disclosure based on the above-described embodiments. Accordingly, the disclosure is not to be limited by what has been particularly shown and described. All publications and references cited herein are expressly incorporated herein by reference in their entirety.

The invention claimed is:

1. An access device, comprising:
an outer tube having a distal end, a proximal end, and a working channel formed therethrough; and
an inner shield disposed through the outer tube such that a distal end of the inner shield protrudes from the distal end of the outer tube,
wherein the inner shield is movable relative to the outer tube between a first position, in which a distal end of a blade of the inner shield is disposed in a radially inward position, and a second position, in which the distal end of the blade of the inner shield is disposed in a radially outward position, and
wherein the inner shield is movable between the first position and the second position based on an amount of force applied upon a cylinder of the inner shield by an inner surface of the outer tube, the force being configured to control the compression of the cylinder about its circumference.

2. An access device, comprising:
an outer tube having a distal end, a proximal end, and a working channel formed therethrough; and
an inner shield disposed through the outer tube such that a distal end of the inner shield protrudes from the distal end of the outer tube, wherein the inner shield is movable relative to the outer tube between a first position, in which a distal end of a blade of the inner shield is disposed in a radially inward position, and a second position, in which the distal end of the blade of the inner shield is disposed in a radially outward position, and wherein the inner shield is movable between the first position and the second position based on an amount of force applied upon a cylinder of the inner shield by an inner surface of the outer tube, the force being configured to control the compression of the cylinder about its circumference, wherein the blade of the inner shield has a length larger than a length of the outer tube, the blade having at least a distal portion adjacent to the distal end of the blade, the distal portion of the blade being configured to retract an obstacle in a radially outward direction, and wherein the cylinder:
(i) is attached to the blade,
(ii) is a cylindrical structure having a cylinder opening formed therethrough,
(iii) has an angled distal-facing surface such that a portion of the distal-facing surface of the cylinder that contacts the blade forms an angle larger than 90 degrees with the blade, and
(iv) is formed of a resilient material that allows for its circumferential compression by the inner surface of the outer tube.

3. The access device of claim 2, wherein, in the first position, the distal end of the blade of the inner shield extends at an oblique angle with respect to a central longitudinal axis of the working channel of the outer tube.

4. The access device of claim 2, wherein, in the first position, a portion of the inner shield extends proximal to the proximal end of the outer tube.

5. The access device of claim 2, wherein the length of a portion of the blade that extends distally from the distal-facing surface of the cylinder is larger than the length of the outer tube, such that the distal end of the blade protrudes through the outer tube opening at the distal end of the outer tube.

6. The access device of claim 2,
wherein a circumference of the cylinder in the first position is larger than the circumference of the opening of the outer tube at the proximal end of the outer tube, and
wherein the circumference of the cylinder in the second position is smaller than the circumference of the opening of the outer tube.

7. The access device of claim 2, where the blade is made of a malleable material, such that the length of the handle portion can be adjusted to a desired size.

8. A surgical method, comprising:
inserting an access tube of an access device into a patient;
positioning an inner shield through a working channel of the access tube in a first position in which a distal portion of a cylinder of the inner shield is inserted through the working channel of the access tube at a proximal end of the access tube, such that an outer surface of the cylinder is not parallel to an inner surface of the access tube, thereby causing a distal end of the inner shield to be disposed radially inward toward a central longitudinal axis of the working channel and an outer surface of the inner shield to be disposed adjacent to tissue of the patient to be retracted; and
moving the inner shield from the first position to the second position by distally sliding the inner shield through the working channel such that the cylinder is inserted within the working channel, thereby causing:
(i) the inner surface of the access tube to compress the cylinder about its circumference,
(ii) the distal end of the inner shield to retract radially outward away from the central longitudinal axis of the working channel, and
(iii) the tissue of the patient to be retracted radially outward.

9. The surgical method of claim 8,
wherein the compressing of the cylinder about its circumference causes (i) the outer surface of the cylinder to contact the inner surface of the access tube and to be parallel thereto, and (ii) the distal end of the inner shield to retract radially outward.

10. The method of claim 8, further comprising rotating the inner shield relative to the access tube while the inner shield is in the second position, such that a different portion of the tissue is retracted radially outward.

11. The device of claim 1, wherein the cylinder is a slotted cylinder.

12. The method of claim 8, wherein the cylinder is a slotted cylinder.

13. The access device of claim 1, wherein, in the first position, the distal end of the blade of the inner shield extends at an oblique angle with respect to a central longitudinal axis of the working channel of the outer tube.

14. The access device of claim 1, wherein, in the first position, a portion of the inner shield extends proximal to the proximal end of the outer tube.

* * * * *